United States Patent
Vavvas et al.

(10) Patent No.: US 10,022,419 B2
(45) Date of Patent: Jul. 17, 2018

(54) METHODS FOR TREATING SPINAL CORD INJURY

(71) Applicants: Massachusetts Eye and Ear Infirmary, Boston, MA (US); Children's Medical Center Corporation, Boston, MA (US)

(72) Inventors: Demetrios G. Vavvas, Boston, MA (US); Joan W. Miller, Winchester, MA (US); Larry Benowitz, Newton, MA (US)

(73) Assignees: MASSACHUSETTS EYE AND EAR INFIRMARY, Boston, MA (US); CHILDREN'S MEDICAL CENTER CORPORATION, Boston, MA (US)

( * ) Notice: Subject to any disclaimer, the term of this patent is extended or adjusted under 35 U.S.C. 154(b) by 0 days.

(21) Appl. No.: 14/930,501

(22) Filed: Nov. 2, 2015

(65) Prior Publication Data
US 2016/0151442 A1 Jun. 2, 2016

Related U.S. Application Data

(63) Continuation of application No. 14/352,960, filed as application No. PCT/US2012/061324 on Oct. 22, 2012, now abandoned.

(60) Provisional application No. 61/550,191, filed on Oct. 21, 2011.

(51) Int. Cl.
| A61K 38/05 | (2006.01) |
| A61K 45/06 | (2006.01) |
| A61K 31/27 | (2006.01) |
| A61K 31/4178 | (2006.01) |
| A61K 38/00 | (2006.01) |

(52) U.S. Cl.
CPC ............. *A61K 38/05* (2013.01); *A61K 31/27* (2013.01); *A61K 31/4178* (2013.01); *A61K 38/005* (2013.01); *A61K 45/06* (2013.01)

(58) Field of Classification Search
None
See application file for complete search history.

(56) References Cited

U.S. PATENT DOCUMENTS

| 5,443,505 A | 8/1995 | Wong et al. |
| 5,766,242 A | 6/1998 | Wong et al. |
| 6,245,523 B1 | 6/2001 | Altieri |
| 6,251,090 B1 | 6/2001 | Avery et al. |
| 6,299,895 B1 | 10/2001 | Hammang et al. |
| 6,375,972 B1 | 4/2002 | Guo et al. |
| 6,413,540 B1 | 7/2002 | Yaacobi |
| 6,416,777 B1 | 7/2002 | Yaacobi |
| 7,622,106 B1 | 11/2009 | Wang et al. |
| 9,492,432 B2 | 11/2016 | Vavvas et al. |
| 2007/0049565 A1 | 3/2007 | Gwag et al. |
| 2007/0298129 A1 | 12/2007 | Gwag et al. |
| 2009/0099242 A1 | 4/2009 | Cuny et al. |
| 2011/0071088 A1 | 3/2011 | Benowitz |
| 2013/0137642 A1 | 5/2013 | Vavvas et al. |
| 2014/0024598 A1 | 1/2014 | Vavvas et al. |
| 2014/0357570 A1 | 12/2014 | Vavvas |
| 2016/0367619 A1 | 12/2016 | Vavvas et al. |

FOREIGN PATENT DOCUMENTS

| WO | WO-2000/040089 A1 | 7/2000 | |
| WO | WO-2001/028474 A1 | 4/2001 | |
| WO | WO-2001/028493 A2 | 4/2001 | |
| WO | WO-2001/039792 A2 | 6/2001 | |
| WO | WO-2002/089767 A1 | 11/2002 | |
| WO | WO-2003/061519 A2 | 7/2003 | |
| WO | WO-2005/077344 A2 | 8/2005 | |
| WO | WO-2007/071448 A2 | 6/2007 | |
| WO | WO2007/075772 | * 7/2007 | ......... A61K 31/4178 |
| WO | WO-2008/045406 A2 | 4/2008 | |
| WO | WO-2009/023272 A1 | 2/2009 | |
| WO | WO-2010/022140 A1 | 2/2010 | |
| WO | WO-2010/075290 A1 | 7/2010 | |
| WO | WO-2011/071088 A1 | 6/2011 | |
| WO | WO-2011/133964 A2 | 10/2011 | |
| WO | WO-2012/061045 A2 | 5/2012 | |
| WO | WO-2013/059791 A2 | 4/2013 | |

OTHER PUBLICATIONS

Xu et al., Synergistic protective effects of humanin and necrostatin-1 on hypoxia and ischemia/reperfusion injury. Brain Research 1355 ( 2010) 189-194.*
Côté et al., Peripheral Nerve Grafts Support Regeneration after Spinal Cord Injury, Apr. 2011, Neurotherapeutics: The Journal of the American Society for Experimental NeuroTherapeutics 8:294-303.*
Beate et al., Review of Current Evidence for Apoptosis After Spinal Cord Injury, 2000, Journal of Neurotrauma 17(10):915-925.*
Schwartz, M., Optic nerve crush: protection and regeneration, 2004, Brain Research Bulletin 62:467-471.*
Ambati, et al. (2000) "Diffusion of High Molecular Weight Compounds through Sclera," Investgative Ophthamology & Visual Science, 41:1181-1185.
Ambati, et al. (2000) "Transscleral Delivery of Bioactive Protein to the Choroid and Retina," Investigative Opthalmology & Visual Science, 41:1186-1191.
Arimura N. et al., (2009) 'Intraocular Expression and Release of High-Mobility Group Box 1 Protein in Retinal Detachment,' Lab Invest, 89(3):278-89.
Arroyo, et al. (2005) "Photoreceptor Apoptosis in Human Retinal Detachment," American Journal of Opthalmology,139: 605-610.

(Continued)

*Primary Examiner* — John D Ulm
(74) *Attorney, Agent, or Firm* — Goodwin Procter LLP

(57) ABSTRACT

Provided are methods for promoting axon regeneration of a Central Nervous System (CNS) neuron and promoting nerve function following injury to a CNS neuron, for example, brain and/or spinal cord injury. Axon regeneration in a CNS neuron or nerve function following injury to a CNS neuron can be promoted by administering a necrosis inhibitor either alone or in combination with an apoptosis inhibitor to a subject suffering from a CNS disorder, wherein a symptom of the CNS disorder is axon degeneration.

12 Claims, 4 Drawing Sheets

(56) References Cited

OTHER PUBLICATIONS

Balkwill F, (2009) 'Tumor Necrosis Factor and Cancer,' Nat Rev Cancer, 9(5):361-71.
Barber AJ et al., (1998) 'Neural Apoptosis in the Retina During Experimental and Human Diabetes. Early Onset and Effect of Insulin,' J Clin Invest, 102(4):783-91.
Campo, et al. (1999) "Pars Plana Vitrectomy Without Scleral Buckle for Pseudophakic Retinal Detachments," Opthalmology, 106:1811-1815.
Candé, et al. (2004) "Apoptosis-Inducing Factor (AIF): Caspase-Independent After All," Cell Death and Differentiation, 11:591-595.
Cavassani, et al. (2008) "TLR3 is an Endogenous Sensor of Tissue Necrosis During Acute Inflammatory Events," The Journal of Experimental Medicine, 205:2609-2621.
Chan, et al., (2011) "Rescue of Cybids Containing Leber Hereditary Optic Neuropathy (Ihon) Mutation Using Neorostatin-1 and-Pancaspase Inhibitor Combination," Annual Meeting of the Association-for-Researoh-in-Vision-and-Ophthalmology (ARVO), May 1, 2011, (ABSTRACT).
Chang, et al. (2002) "Retinal Degeneration Mutants in the Mouse," Vision Research, 42:517-525.
Chaudhary, et al. (1999) "Caspase Inhibitors Block the Retinal Ganglion Cell Death Following Optic Nerve Transection," Molecular Brain Research, 67:36-45.
Chauvier (2007) "Broad-Spectrum Caspase Inhibitors: From Myth to Reality?," Cell Death and Differentiation, 14,387-391.
Cho YS et al., (2009), 'Phosphorylation-Driven Assembly of the RIP1-RIP3 Complex Regulates Programmed Necrosis and Virus-Induced Inflammation,' Cell, 137(6):1112-23 (HHS Public Access version of author manuscript).
Chua, et al. (2006) "Necrostatin-1 is a Novel Protector of Myocardial Infarction," 79th Annual Scientific Session of the American Heart Association, Chicago, IL, 114(18):212. (Abstract).
Chua, et al. (2010) "Neuroprotective Agents in Glaucoma Therapy: Recent Developments and Future Directions," Expert Reviews Ophthalmology, 5(5):627-636.
Cook, et al. (1995) "Apoptotic Photoreceptor Degeneration in Experimental Retinal Detachment," Investigative Ophthamology & Visual Science, 36: 990-996.
Cuervo, et al. (1996) "A Receptor for the Selective Uptake and Degradation of Proteins by Lysosomes," Science, 273:501-503.
Cuny, et al. (2008) "Necroptosis—A Novel Cell Death Mechanism," Drugs of the Future, 33(3):225-233.
D'Onofrio, et al. (2011) "Involvement of Caspase-6 and Caspase-8 in Neuronal Apoptosis and the Regenerative Failure of Injured Retinal Ganglion Cells," Investigative Ophthalmology & Visual Science, p. 5448. Abstract only.
Degterev A et al., (2005) 'Chemical Inhibitor of Nonapoptotic Cell Death with Therapeutic Potential for Ischemic Brain Injury,' Nat Chem Biol, 1(2):112-9.
Degterev A et al., (2008) 'Identification of RIP1 Kinase as a Specific Cellular Target of Necrostatins,' Nat Chem Biol, 4(5):313-21.
Deveraux QL et al., (1998) 'IAPs Block Apoptotic Events Induces by Capase-8 and Cytochrome C by Direct Inhibition of Distinct Caspases,' EMBO J, 17(8):2215-23.
Dice (2007) "Chaperone-Mediated Autophagy," Autophagy, 3:295-299.
Donovan, et al. (2009) "Caspase-Independent Photoreceptor Apoptosis in vivo and Differential Expression of Apoptotic Protease Activating Factor-1 and Caspase-3 During Retinal Development," Cell Death and Differentiation, 9:1220-1231.
Dreyer, et al. (1996) "Elevated Glutamate Levels in the Vitreous Body of Humans and Monkeys with Glaucoma," Arch Ophthalmology, 114(3):299-305.
Dunaief, et al. (2002) "The Role of Apoptosis in Age-Related Macular Degeneration," Arch Ophthalmology, 120:1435-1442.
Ekert, et al. (1999) "Caspase Inhibitors," Cell Death and Differentiation, 6:1081-1086.
Erickson, et al. (1983) "Retinal Detchment in the Cat: The Outer Nuclear and Outer Plexiform Layers," Investigative Ophthalmology & Visual Science, 24: 927-942.
Festjens N et al., (2006) 'Necrosis, a Well-Orchestrated Form of Cell Demise: Signalling Cascades, Important Mediators and Concomitant Immune Response,' Biochim Biophys Acta, 1757(9-10):1371-87.
Festjens N et al., (2007) 'RIP1, a Kinase on the Crossroads of a Cell's Decision to Live or Die,' Cell Death Differ, 14(3):400-10.
Fulton, et al. (2001) "The Rod Photoreceptors in Retinopathy of Prematurity, An Electroretinographic Study," Arch Ophthalmology, 119:499-505.
Galluzzi, et al. (2008) "Necroptosis: A Specialized Pathway of Programmed Necrosis," Cell, 135:1161-1163.
Galluzzi, et al. (2009) "RIP Kinases Initiate Programmed Necrosis," Journal of Molecular Cell Biology, 1:8-10.
Golstein P and Kroemer G, (2006) 'Cell Death by Necrosis: Towards a Molecular Definition,' Trends Biochem Sci, 32(1):37-43.
Grasl-Kraupp, et al. (1995) "In Situ Detection of Fragmented DNA (TUNEL Assay) Fails to Discriminate Among Apoptosis, Necrosis, and Autolytic Cell Ceath: A Cationary Note," Hepatology, 21:1465-1468.
Hagimura, et al. (2002) "Persistent Foveal Retinal Detachment After Successful Rhegmatogenous Retinal Detachment Surgery," American Journal of Ophthalmology, 133:516-520.
He S et al., (2009) 'Receptor Interacting Protein Kinase-3 Determines Cellular Necrotic Response to TNF-α,' Cell 137(6):1100-11.
Hisatomi, et al. (2001) "Relocalization of Apoptosis-Inducing Factor in Photoreceptor Apoptosis Induced by Retinal Detachment In Vivo," American Journal of Pathology, 158:1271-1278.
Hisatomi, et al. (2003) "Clearance of Apoptotic Photoreceptors: Elimination of Apoptotic Debris into the Subretinal Space and Macrophage-Mediated Phagocytosis via Phosphatidylserine Receptor and Integrin αvβ3," Am J Pathol, 162:1869-1879.
Histatomi, et al. (2008) "HIV Protease Inhibitors Provide Neuroprotection Through Inhibition of Mitochondrial Apoptosis in Mice," Journal of Clinical Investigation, 118:2025-2038.
Hoglen, et al. (2004) "Characterization of IDN-6556 (3-{2-(2-tert-Butyl-Phenylaminooxalyl)-Amino]-Propionylamino}-4-oxo-5-(2,3,5,6-Tetrafluoro-Phenoxy-Pentanoic Acid): A Liver-Targeted Caspase Inhibitor," J Pharmacol Exp Therapeut, 309:634-640.
Holler N et al., (2000) 'Fas Triggers an Alternative, Caspase-8-Independent Cell Death Pathway Using the Kinase RIP as Effector Molecule,' Nat Immunol, 1(6):489-95.
Ichimura, et al. (2000) "A Ubiquitin-Like System Mediates Protein Lipidation," Nature, 408:488-492.
International Search Report and Written Opinion for PCT/US2011/033704, dated Jun. 22, 2012, (14 pages.)
International Search Report and Written Opinion for PCT/US2011/057327, dated May 21, 2013, (14 pages).
International Search Report for PCT/US2012/061324 dated May 16, 2013 (6 pages).
Jones (2005) "Neurodegenerative Disorders: Blocking a Path to Cell Death," [online] [retrieved on Mar. 12, 2015] Retrieved from 22.signaling-gateway.org/Update/Updates/200508/nrn1732.html. (2 pages.)
Kabeya, et al. (2000) "LC3, a Mammalian Homologue of Yeast Apg8p, is Localized in Autophagosome Membranes After Processing," EMBO Journal, 19(21):5720-5728.
Kaiser WJ et al., (2008) 'Receptor-Interacting Protein Homotypic Interaction Motif-Dependent Control of NF-κB activation via the DNA-Dependent Activator of IFN Regulatory Factors,' J Immunol, 181(9):6427-34.
Karl, et al. (2008) "Stimulation of Neural Regeneration in the Mouse Retina," Proceedings of the National Academy of Science U.S.A. 105(49):19508-19513.
Kayama, et al. (2010) "Transfection with pax6 Gene of Mouse Embryonic Stem Cells and Subsequent Cell Cloning Induced Retinal Neuron Progenitors, including Retinal Ganglion Cell-Like Cells, In Vitro," Opthalmic Research, 43(2):79-91.
Kelliher, et al. (1998) "The Death Domain Kinase RIP Mediates the TNF-Induced NF-κbeta Signal," Immunity, 8:297-303.

(56) References Cited

OTHER PUBLICATIONS

Kermer, et al. (2000) "Caspase-9: Involvement in Secondary Death of Axotomized Rat Retinal Ganglion Cells In Vivo," Molecular Brain Research, 85:144-150.
Kermer, et al., (1998) "Inhibition of CPP32-Like Proteases Rescues Axotomized Retinal Ganglion Cells from Secondary Cell Death in vivo," Journal of Neuroscience, 18:4656-4662.
Kerrigan, et al. (1997) "TUNEL-Positive Ganglion Cells in Human Primary Open-Angle Glaucoma," Arch Ophthalmology, 115:1031-1035.
Kim, et al. (2007) "TNF-Induced Activation of the Nox1 NADPH Oxidase and Its Role in the Induction of Necrotic Cell Death," Molecular Cell, 26:675-687.
Knöferle, et al. (2010) "Mechanisms of Acute Oxonal Degeneration in the Optic Nerve In Vivo," Proceedings of the National Academy of Science U.S.A., 107(13):6064-6069.
Kong J et al., (2009), 'Rescue of Motor Neurons in ALS by Targeting the BNIP3 Cell Death Pathway,' The 20th International Symposium on ALS/MND, Dec. 8-10, 2009, Berlin, Germany, Poster P25, *Poster Communications: Therapeutic Strategies*, 10(Supp 1):78-9 (Poster).
Kourtis, et al. (2009) "Autophagy and Cell Death in Model Organisms," Cell Death and Differentiation, 16:21-30.
Krantic, et al. (2007) "Apoptosis-Inducing Factor: A Matter of Neuron Life and Death," Progress in Neurobiology, 81:179-196.
Kroemer G et al., (2009) 'Classification of Cell Death: Recommendations of the Nomenclature Committee on Cell Death 2009,' Cell Death Differ, 16(1):3-11 (HHS Public Access version of author manuscript).
Kubay, et al. (2005) "Retinal Detachment Neuropathology and Potential Strategies for Neuroprotection," Survey of Opthalmology, 50:463-475.
Lee, et al. (2004) "The Kinase Activity of Rip1 is Not Required for Tumor Necrosis Factor-α-Induced Iκbeta Kinase or p38 MAP Kinase Activation or for the Ubiquitination of Rip1 by Traf2," The Journal of Biological Chemistry, 279(32):33185-33191.
Leon S et al., (2000) 'Lens Injury Stimulates Axon Regeneration in the Mature Rat Optic Nerve,' J Neurosci, 20(12):4615-26.
Levine B and Klionsky DJ, (2004) 'Development by Self-Digestion: Molecular Mechanisms and Biological Functions of Autophagy,' Dev Cell, 6(4):463-77.
Levine, et al. (2005) "Autophagy in Cell Death: An Innocent Convict?," The Journal of Clinical Investigation, 115(10):2679-2688.
Levkovitch-Verbin H, (2004) 'Animal Models of Optic Nerve Disease,' Eye (Lond), 18(11):1066-74.
Li, et al.(2006) "Ubiquitination of RIP is Required for Tumor Necrosis Factor α-induced NF-κbeta Activation," The Journal of Biological Chemistry, 281(19):13636-13643.
Libby, et al. (2005) "Susceptibility to Neurodegeneration in a Glaucoma is Modified by Bax Gene Dosage," PLos Genetics, 1(1):0017-0026.
Lin Y et al., (1999) 'Cleavage of the Death Domain Kinase RIP by Caspase-8 Prompts TNF-Induced Apoptosis,' Genes Dev, 13(19):2514-26.
Lin, et al. (2004) "Tumor Necrosis Factor-Induced Nonapoptotic Cell Death Requires Receptor-Interacting Protein-Mediated Cellular Reactive Oxygen Species Accumulation," The Journal of Biological Chemistry, 279(11):10822-10828.
Linton SD, (2005) 'Caspase Inhibitors: A Pharmaceutical Industry Perspective,' Curr Top Med Chem, 5(16):1697-717.
Mahoney, et al. (2008) "Both cIAP1 and cIAP2 Regulate TNFα-Mediated NF-κβ Activation," Proc Natl Acad Sci USA.,105:11778-83.
Mann, et al. (1948) "The Perception of the Vertical: I. Visual and Non-Labyrinthine Cues," Investigation conducted jointly with the School of Aviation Medicine and Research with the Office of Naval Research, Journal of Experimental Psychology, 39(4):538-547.
Merfeld (2011) "Signal Detection Theory and Vestibular Thresholds: I. Basic Theory and Practical Considerations," Experimental Brain Research, 210:389-405.
Moubarak, et al. (2007) "Sequential Activation of Poly(ADP-Ribose) Polymerase 1, Calpains, and Bax is Essential in Apoptosis-Inducing Factor-Mediated Programmed Necrosis," Molecular Cell Biology, 27(13):4844-4862.
Murakami, et al. (2008) "Cell Injury, Repair, Aging and Apoptosis, Inhibition of Nuclear Translocation of Apoptosis-Inducing Factor is an Essential Mechanism of the Neuroprotective Activity of Pigment Epithelium-Derived Factor in a Rat Model of Retinal Degeneration," American Journal of Pathology, 173(5):1326-1338.
Murakami, et al. (2010) "Receptor Interacting Protein 1 Kinase is an Essential Mediator of Programmed Photoreceptor Necrosis After Retinal Detachment," Association for Research in Vision and Ophthalmology (ARVO) 2010 Annual Meeting, Ft. Lauderdal, FL May 2-6, 2010, Program #/Poster #:4034/A427, (2 pages) (Abstract available online Apr. 23, 2010).
Nakazawa, et al. (2006) "Characterization of Cytokine Responses to Retinal Detachment in Rats," Molecular Vision, 12:867-878.
Nakazawa, et al. (2006) "Tumor Necrosis Factor-α Mediates Oligodendrocyte Death and Delayed Retinal Ganglion Cell Loss in a Mouse Model of Glaucoma," Journal of Neuroscience, 26(49):12633-12641.
Nakazawa, et al., (2006), 'Monocyte Chemoattractant Protein 1 Mediates Retinal Detachment-Induced Photoreceptor Apoptosis,' Proc Natl Acad Sci USA, 104(7):2425-30.
Newton, et al. (2004) "Kinase RIP3 Is Dispensable for Normal NF-1βs, Signaling by the β-Cell and T-Cell Receptors, Tumor Necrosis Factor Receptor 1, and Toll-Like Receptors 2 and 4," Molecular Cellular Biology, 24:1464-1469.
Papapetropoulos A et al., (2000) 'Angiopoietin-1 Inhibits Endothelial Cell Apoptosis via the Akt/surviving Pathway,' J Biol Chem, 275(13):9102-5.
Rosenbaum, et al. (2009) "Necroptosis, a Novel Form of Caspase-Independent Cell Death, Contributes to Neuronal Damage in a Retinal Ischemia-Reperfusion Injury Model," Journal of Neuroscience Research, 88:1569-1576.
Saggu Sk et al., (2010) 'Wallerian-like Axonal Degeneration in the Optic Nerve after Excitotoxic Retinal Insult: An Ultrastructural Study,' BMC Neurosci, 11:97 (14 pages).
Sanges, et al. (2006) "Apoptosis in Retinal Degeneration Involves Cross-Talk Between Apoptosis-Inducing Factor (AIF) and Caspase-12 and is Blocked by Calpain Inhibitors," Proceedings of National Academy of Science, U.S.A., 103:17366-17371.
Scaffidi, et al. (2002) "Release of Chromatin Protein HMGB1 by Necrotic Cells Triggers Inflammation," Nature, 418:191-195.
Seglen, et al. (1982) "3-Methyladenine: Specific Inhibitor of Autophagic/Lysosomal Protein Degradation in Isolated Rat Hepatocytes," Proceedings of National Academy of Science, U.S. A., Cell Biology, 79:1889-1892.
Sintzel, et al. (1996) "Biomaterials in Ophthalmic Drug Delivery," European Journal of Pharmaceutics and Biopharmaceutics, 42:358-374.
Susin (2000) "Two Distinct Pathways Leading to Nuclear Apoptosis," Journal of Experimental Medicine, 192(4): 571-580.
Susin, et al. (1999) "Molecular Characterizationof Mitochondrial Apoptosis-Inducing Factor," Nature, 397:441-446.
Tatton, et al. (2001) "Maintaining Mitochondrial Membrane Impermeability: An Opportunity for New Therapy in Glaucoma?," Survey of Ophthalmology, 45(3):S277-S283.
Teng X et al., (2007) 'Structure-Activity Relationship Study of [1,2,3]thiadiazole Necroptosis Inhibitors,' Bioorg Med Chem Lett, 17(24):6836-40.
Teng X et al., (2008) 'Structural-Activity Relationship and Liver Microsome Stability Studies of Pyrrole Necroptosis Inhibitors,' Bioorg Med Chem Lett, 18(11):3219-23 (HHS Public Access version of author manuscript).
Tezel, et al. (2001) "TNF-α and TNF-α Receptor-1 in the Retina of Normal and Glaucomatous Eyes," Investigative Ophthalmology & Visual Science, 42(8):1787-1794.
Trichonas G et al., (2009) 'Identification of Necroptosis as a Mechanism of Photoreceptor Damage After Retinal Detachment

(56) References Cited

OTHER PUBLICATIONS and Nec-1 as a Potential Treatment,' Invest Ophthalmol Vis Sci 2009, 50:E-Abstract #5187 (2 pages) (Abstract).
Trichonas, et al. (2010) "Receptor Interacting Protein Kinases Mediate Retinal Detachment-Induced Photoreceptor Necrosis and Compensate for Inhibition of Apoptosis," Proceedings of National Academy of Science, U.S.A., 107:21695-21700.
Tuo, et al. (2007) "Murine Ccl2/Cx3cr1 Deficiency Results in Retinal Lesions Mimicking Human Age-Related Macular Degeneration," Investigative Ophthalmology & Visual Science, 48(8):3827-3836.
Vandenabeele, et al. (2010) "The Role of the Kinases RIP1 and RIP3 in TNF-Induced Necrosis," Sci Signaling, 3:re4.
Vanlangenakker, et al., (2011), 'cIAP1 and TAK1 Protect Cells from TNF-Induced Necrosis by Preventing RIP1/RIP3-Dependent Reactive Oxygen Species Production,' Cell Death Differ,18(4):656-65.
Vavvas, et al., (2008) "Identification of Necroptosis as a Mechanism of Photoreceptor Damage after Retinal Detachment and Nec-1 as a Potential Treatment," 41st Annual Meeting of the Retina Society, Sep. 25-28, 2008, Scottsdate, AZ (1 page). (Abstract first available online Jun. 1, 2008).
Vercammen, et al. (1998) "Dual Signaling of the Fas Receptor: Initiation of Both Apoptotic and Necrotic Cell Death Pathways," Journal of Experimental Medicine, 188:919-930.
Wang, et al. (2008) "TNF-α Induces Two Distinct Caspase-8 Activation Pathways," Cell, 133:693-703.
Written Opinion of the International Searching Authority for PCT/US2012/061324 dated May 16, 2013 (11 pages).
Xu X et al., (2010) 'Synergistic Protective Effects of Humanin and Necrostatin-1 on Hypoxia and Ischemia/Reperfusion Injury,' Brain Res, 1355:189-94 (HHS Public Access version of author manuscript).
Yan, et al. (2000) "Matrix Metalloproteinases and Tumor Necrosis Factor-α in Glaucomatous Optic Nerve Head," Arch Ophthalmology, 118:666-673.
Yang, et al. (2008) "Toll-Like Receptor 3 and Geographic Atrophy in Age-Related Macular Degeneration," New England Journal of Medicine, 359:1456-1463.
Yu, L. et al. (2004) "Regulation of an ATG7-Beclin 1 Program of Autophagic Cell Death by Caspase-8," Science, 304(5676):1500-1502.
Yuan, et al. (2000) "Tumor Necrosis Factor-α: A Potentially Neurodestructive Cytokine Produced by Glia in the Human Glaucomatous Optic Nerve Head,", Glia, 32:42-50.
Zacks, et al. (2003) "Caspase Activation in an Experimental Model of Retinal Detachment," Investigative Ophthalmology & Visual Science, 44:1262-1267.
Zacks, et al. (2004) "FAS-Mediated Apoptosis and Its Relation to Intrinsic Pathway Activation in an Experimental Model of Retinal Detachment," Investigative Ophthalmology & Visual Science, 45:4563-4569.
Zacks, et al. (2007) "Role of the Fas-Signaling Pathway in Photoreceptor Neuroprotection," Arch Ophthamology, 125:1389-1395.
Zhang DW et al., (2009) 'RIP3, an Energy Metabolism Regulator that Switches TNF-Induced Cell Death from Apoptosis to Necrosis,' Science, 325(5938):332-6.
Zheng W et al., (2008), 'Structure-Activity Relationship Study of a Novel Necroptosis Inhibitor, Necrostatin-7,' Bioorg Med Chem Lett, 18(18):4932-5.
Zhu S et al., (2011) 'Necrostatin-1 Ameliorates Symptoms in R6/2 Transgenic Mouse Model of Huntington's Disease,' Cell Death Dis, 2:e115.
Zhu, et al. (2000) "Stabilization of Proteins Encapsulated in Injectable Poly (Lactide-co-glycolide)," Nature Biotechnology, 18:52-57.
Zitvogel, et al. (2010) "Decoding Cell Death Signals in Inflammation and Immunity," Cell, 140:798-804.
Cui et al., (1999), 'CNTF, not Other Trophic Factors, Promotes Axonal Regeneration of Axotomized Retinal Ganglion Cells in Adult Hamsters,' Invest Ophthalmol Vis Sci, 40(3):760-6.
Duan et al., (2015), 'Subtype-Specific Regeneration of Retinal Ganglion Cells Following Axotomy: Effects of Osteopontin and mTOR Signaling,' Neuron, 85(6):1244-56.
Finn et al., (2000), 'Evidence that Wallerian Degeneration and Localized Axon Degeneration Induced by Local Neutrophin Deprivation do not Involve Caspases,' J Neurosci, 20(4):1333-41.
Hu et al., (2012), 'Differential Effects of Unfolded Protein Response Pathways on Axon Injury-Induced Death of Ganglion Cells,' Neuron, 73(3):445-52.
Murakami et al., (2011), 'RIP Kinase-Mediated Necrosis as an Alternative Mechanism of Photoreceptor Death,' Oncotarget, 2(6):497-509.
Norsworthy et al., (2017), 'Sox11 Expression Promotes Regeneration of Some Retinal Ganglion Cell Types but Kills Others,' Neuron, 94(6):1112-20.
Park et al., (2009), 'Cytokine-Induced SOCS Expression is Inhibited by cAMP Analogue: Impact on Regeneration in Injured Retina,' Mol Cell Neurosci, 41(3):313-24.

* cited by examiner

ONC

ONC Nec1  x3(D0,D3,D7)

ONC ZVAD  x3(D0,D3,D7)

METHODS FOR TREATING SPINAL CORD INJURY

CROSS REFERENCE TO RELATED APPLICATIONS

This application is a continuation of U.S. patent application Ser. No. 14/352,960, filed Apr. 18, 2014, which is the U.S. national stage of International (PCT) Patent Application No. PCT/US2012/061324, filed Oct. 22, 2012, which claims the benefit of and priority to U.S. Provisional Patent Application No. 61/550,191, filed Oct. 21, 2011, the contents of each of which are hereby incorporated by reference in their entirety.

GOVERNMENT FUNDING

The work described in this application was sponsored, in part, by the National Eye Institute under Grant No. EY14104. The United States Government has certain rights in the invention.

FIELD OF THE INVENTION

The field of the invention relates generally to methods for promoting axon regeneration. More particularly, the invention relates to the use of a necrosis inhibitor, e.g., a RIP kinase inhibitor, e.g., a necrostatin, either alone or in combination with an apoptosis inhibitor, e.g., a pan-caspase inhibitor, for preserving neuron viability, promoting nerve function, and enhancing axon outgrowth.

BACKGROUND OF THE INVENTION

The nervous system is divided into two parts: the central nervous system (CNS), which includes the brain and the spinal cord, and the peripheral nervous system, which includes nerves and ganglions outside of the brain and the spinal cord. While the peripheral nervous system is capable of repair and regeneration, the central nervous system is unable to self-repair and regenerate.

In the United States, traumatic injuries to the CNS such as traumatic brain injury and spinal cord injury affect over 90,000 people each year. Furthermore, neurodegenerative diseases such as dementia, stroke, Alzheimer's disease, Parkinson's disease, and Huntington's disease affect millions of people worldwide. These traumatic and age-related insults to the CNS cause axonal loss, disrupt neuronal connections, and ultimately result in permanent blindness, paralysis, and other losses in cognitive, motor, and sensory functions. There is currently no effective treatment for recovering human nerve functions after CNS injury.

Apoptosis and necrosis represent two different mechanisms of cell death. Apoptosis is a highly regulated process involving the caspase family of cysteine proteases, and characterized by cellular shrinkage, chromatin condensation, and DNA degradation. In contrast, necrosis is associated with cellular and organelle swelling and plasma membrane rupture with ensuing release of intracellular contents and secondary inflammation (Kroemer et al., (2009) CELL DEATH DIFFER 16:3-11). Necrosis has been considered a passive, unregulated form of cell death; however, recent evidence indicates that some necrosis can be induced by regulated signal transduction pathways such as those mediated by receptor interacting protein (RIP) kinases, especially in conditions where caspases are inhibited or cannot be activated efficiently (Golstein P & Kroemer G (2007) TRENDS BIOCHEM. SCI. 32:37-43; Festjens et al. (2006) BIOCHIM. BIOPHYS. ACTA 1757:1371-1387). Stimulation of the Fas and TNFR family of death domain receptors (DRs) is known to mediate apoptosis in most cell types through the activation of the extrinsic caspase pathway. In addition, in certain cells deficient for caspase-8 or treated with pan-caspase inhibitor ZVAD, stimulation of death domain receptors (DR) causes a RIP-1 kinase dependent programmed necrotic cell death instead of apoptosis (Holler et al. (2000) NAT. IMMUNOL. 1:489-495; Degterev et al. (2008) NAT. CHEM. BIOL. 4:313-321). This novel mechanism of cell death is termed "programmed necrosis" or "necroptosis" (Degterev et al., (2005) NAT CHEM BIOL 1:112-119).

Receptor Interacting Protein kinase 1 (RIP-1) is a serine/threonine kinase that contains a death domain and forms a death signaling complex with the Fas-associated death domain and caspase-8 in response to death receptor (DR) stimulation (Festjens et al. (2007) CELL DEATH DIFFER. 14:400-410). During death domain receptor-induced apoptosis, RIP-1 is cleaved and inactivated by caspase-8, the process of which is prevented by caspase inhibition (Lin et al. (1999) GENES. DEV. 13:2514-2526). It has been unclear how RIP-1 kinase mediates programmed necrosis, but recent studies revealed that the expression of RIP-3 and the RIP-1-RIP-3 binding through the RIP homotypic interaction motif is a prerequisite for RIP-1 kinase activation, leading to reactive oxygen species (ROS) production and necrotic cell death (He et al., (2009) CELL 137:1100-1111; Cho et. al., (2009) CELL 137:1112-1123; Zhang et al., (2009) SCIENCE 325:332-336).

There is still an ongoing need to minimize or eliminate neuronal cell death and promote neuronal regeneration and axonal growth in patients affected with a CNS disorder such as, for example, traumatic CNS injuries and neurodegenerative diseases.

SUMMARY OF THE INVENTION

The invention is based, in part, on the discovery that a necrosis inhibitor, e.g., RIP kinase inhibitor, e.g., a necrostatin, e.g., necrostatin-1, can be used to preserve neuron viability and promote axon growth and nerve functions. The studies described herein indicate that programmed necrosis may be a critical mechanism for CNS disorders wherein symptoms of the disorder include neuronal cell death, axon degeneration, and/or impaired axon growth. As a result, it may be possible to reduce or even reverse the loss of cognitive, motor, and sensory functions associated with a CNS disorder, by preserving neuron viability and/or promoting axon regeneration and/or nerve functions.

In one aspect, the invention provides a method for promoting axon regeneration in a CNS neuron by exposing the CNS neuron to an effective amount of a necrosis inhibitor and an effective amount of an apoptosis inhibitor thereby to promote the regeneration of the axon. The CNS neuron may be ex vivo or in vivo. The CNS neuron may include, but is not limited to, a CNS sensory neuron, a motor neuron, a cortical neuron, a cerebellar neuron, a hippocampal neuron, and a midbrain neuron.

In another aspect, the invention provides a method for promoting nerve function following injury to a CNS neuron. The method comprises administering to a subject an effective amount of a necrosis inhibitor and an effective amount of an apoptosis inhibitor thereby to promote CNS neuron function. In a further aspect, the invention provides a method for preserving the viability of a CNS neuron, wherein the method comprises administering to a subject an effective amount of a necrosis inhibitor and an effective amount of an apoptosis inhibitor thereby to preserve the viability of the CNS neuron. After administration of the necrosis inhibitor and the apoptosis inhibitor, the CNS neuron may be capable of supporting axonal regeneration.

In another aspect, the invention provides a method of treating a CNS disorder in a subject in need thereof, wherein a symptom of the CNS disorder is axon degeneration within a CNS neuron. The method comprises administering to the subject an effective amount of a necrosis inhibitor and an effective amount of an apoptosis inhibitor thereby to promote regeneration of an axon in a CNS neuron affected by the CNS disorder. Following administration of the necrosis inhibitor and the apoptosis inhibitor, neural functions may be measured, for example, as an indication of axon regeneration. It is also contemplated that, following administration of the necrosis inhibitor and the apoptosis inhibitor, the neuron function of the CNS neuron is preserved or improved relative to the neuron function prior to administration of the necrosis inhibitor and the apoptosis inhibitor. The CNS disorder includes, but is not limited to, brain injury, spinal cord injury, Alzheimer's disease, amyotropic lateral sclerosis (ALS/Lou Gehrig's Disease), Parkinson's disease, multiple sclerosis, diabetic neuropathy, polyglutamine (polyQ) diseases, stroke, Fahr disease, Menke's disease, Wilson's disease, cerebral ischemia, and a prion disorder. In exemplary embodiments, the CNS disorder is brain injury or spinal cord injury.

In another aspect, the invention provides a method of promoting neuron function following injury to a CNS neuron. The method comprises reducing the production and/or activity of a RIP-1 kinase and/or RIP-3 kinase in the CNS neuron thereby to promote CNS neuron function. In certain embodiments, the reduction in the production or activity of the RIP-1 kinase and/or the RIP-3 kinase can achieved by administering an effective amount of RIP kinase (RIPK) inhibitor, e.g., a necrostatin. After treatment with the RIP kinase inhibitor, the CNS neuron may be capable of supporting axonal regeneration.

In another aspect, the invention provides a method of promoting axon regeneration in a CNS neuron, wherein the method comprises reducing the production and/or activity of a RIP-1 kinase and/or a RIP-3 kinase in the CNS neuron thereby promoting axon regeneration in a CNS neuron. In certain embodiments, the reduction in the production or activity of the RIP-1 kinase and/or the RIP-3 kinase can achieved by administering an effective amount of RIP kinase (RIPK) inhibitor, e.g., a necrostatin.

In another aspect, the invention provides a composition for use in promoting axon regeneration in a CNS neuron. The composition comprises a pharmaceutically acceptable carrier, a necrosis inhibitor and an apoptosis inhibitor.

In each of the foregoing methods and compositions, the necrosis inhibitor can be a RIP kinase inhibitor, for example, a necrostatin. In certain embodiments of the foregoing methods, the necrostatin is necrostatin-1, necrostatin-2, necrostatin-3, necrostatin-4, necreostatin-5, necrostatin-7, or a combination thereof. In certain embodiments when a necrostatin is administered, from about 0.05 mg to about 2 mg, 0.1 mg to about 1 mg, from about 0.2 mg to about 1 mg, or from about 0.2 mg to about 0.8 mg, of necrostatin can be administered.

In certain embodiments when a pan-caspase inhibitor is administered, from about 0.05 mg to about 1.5 mg, from about 0.15 mg to about 1.5 mg, from about 0.2 mg to about 1 mg, from about 0.2 mg to about 0.8 mg, from about 0.4 mg to about 1 mg, or from about 0.5 mg to about 0.8 mg, of the pan-caspase inhibitor can be administered. Exemplary pan-caspase inhibitors include zVAD, IDN-6556 or a combination thereof.

The necrosis inhibitor, e.g., a necrostatin, and/or the apoptosis inhibitor may be administered locally. In other embodiments, the necrosis inhibitor, e.g., a necrostatin, and/or the apoptosis inhibitor may be administered systemically.

It is understood that the necrosis inhibitor, e.g., a necrostatin, and/or the apoptosis inhibitor may be administered sequentially or simultaneously. The necrosis inhibitor, e.g., a necrostatin, and the apoptosis inhibitor may be administered in the same or different carriers.

In each of the foregoing methods and compositions, the necrostatin can be selected from one or more of the following necrostatins. For example, in certain embodiments, the necrostatin is a Nec-1 related compound of Formula I:

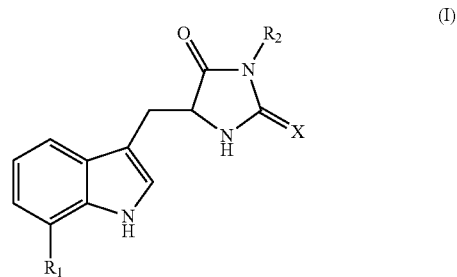

or a pharmaceutically acceptable salt, ester, or prodrug thereof, wherein

X is O or S;

$R_1$ is hydrogen, $C_1$-$C_6$alkyl, $C_1$-$C_6$alkoxyl, or halogen; and $R_2$ is hydrogen or $C_1$-$C_6$alkyl.

In each of the foregoing methods and compositions, the necrostatin can be a Nec-1 related compound of Formula I-A:

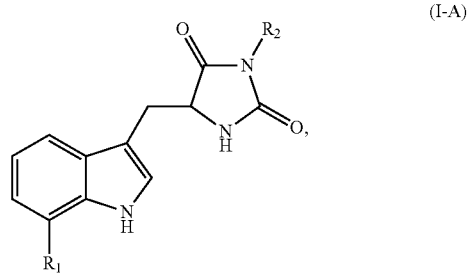

or a pharmaceutically acceptable salt, ester, or prodrug thereof, or optical isomers or racemic mixtures thereof, wherein $R_1$ is H, alkyl, alkoxyl, or a halogen and $R_2$ is H or an alkyl.

In each of the foregoing methods and compositions, the necrostatin can be a Nec-1 related compound of Formula I-B:

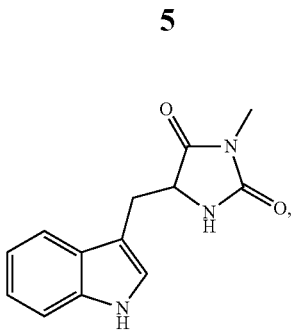

(I-B)

or a pharmaceutically acceptable salt, ester, or prodrug thereof.

In each of the foregoing methods and compositions, the necrostatin can be a Nec-1 related compound of Formula I-C:

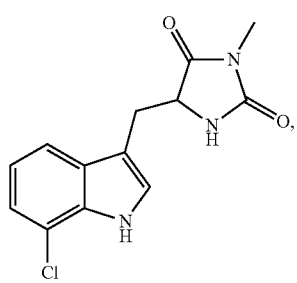

(I-C)

or a pharmaceutically acceptable salt, ester, or prodrug thereof.

In each of the foregoing methods and compositions, the necrostatin can be a Nec-1 related compound of Formula I-D:

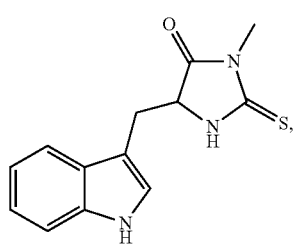

(I-D)

or a pharmaceutically acceptable salt, ester, or prodrug thereof.

In each of the foregoing methods and compositions, the necrostatin can be a Nec-1 related compound of Formula I-E:

(I-E)

or a pharmaceutically acceptable salt, ester, or prodrug thereof, wherein $R_1$ is H, alkyl, alkoxyl, or a halogen (for example, F, Cl, Br or I) and $R_2$ is H or an alkyl.

In each of the foregoing methods and compositions, the necrostatin can be a Nec-1 related compound of Formula I-F:

(I-F)

or a pharmaceutically acceptable salt, ester, or prodrug thereof.

In each of the foregoing methods and compositions, the necrostatin can be a Nec-1 related compound of Formula I-G:

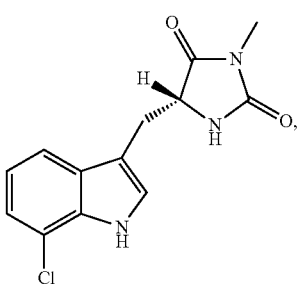

(I-G)

or a pharmaceutically acceptable salt, ester, or prodrug thereof.

In each of the foregoing methods and compositions, the necrostatin can be a Nec-2 related compound of Formula II:

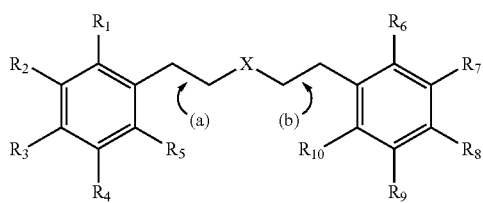

(II)

or a pharmaceutically acceptable salt, ester, or prodrug thereof, wherein:

X is —CH$_2$—, —C(H)(R$_{14}$)—, —C(=S)—, —C(=NH)—, or —C(O)—;

R$_1$, R$_2$, R$_3$, R$_4$, R$_5$, R$_6$, R$_7$, R$_8$, R$_9$, and R$_{10}$ each represent independently hydrogen, acyl, acetyl, alkyl, halogen, amino, C$_1$-C$_6$alkoxyl, nitro, —C(O)R$_{12}$; —C(S)R$_{12}$; —C(O)OR$_{12}$; —C(O)NR$_{12}$R$_{13}$, —C(S)NR$_{12}$R$_{13}$, or —S(O$_2$)R$_{12}$;

R$_{11}$ is hydrogen, acyl, acetyl, alkyl, or acylamino;

R$_{12}$ and R$_{13}$ each represent independently hydrogen, an optionally substituted alkyl, an optionally substituted aryl, an optionally substituted heteroaryl, an optionally substituted aralkyl, or an optionally substituted heteroaralkyl;

R$_{14}$ is acyl, acetyl, alkyl, halogen, amino, acylamino, nitro, —SR$_{11}$, —N(R$_{11}$)$_2$, or —OR$_{11}$;

the bond indicated by (a) can be a single or double bond; and the bond indicated by (b) can be a single or double bond.

In each of the foregoing methods and compositions, the necrostatin can be a Nec-2 related compound of Formula IIA:

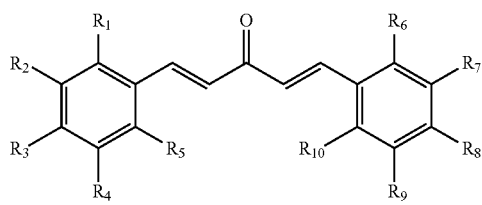

(II-A)

or a pharmaceutically acceptable salt thereof, wherein:

R$_1$, R$_2$, R$_5$, R$_6$, R$_7$, and R$_{10}$ each represent independently hydrogen, alkyl, halogen, amino, or methoxyl; and R$_3$, R$_4$, R$_8$, and R$_9$ are C$_1$-C$_6$alkoxyl.

In each of the foregoing methods and compositions, the necrostatin can be a Nec-3 related compound of Formula III:

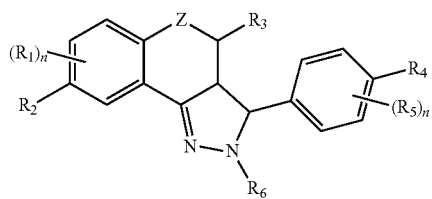

(III)

or a pharmaceutically acceptable salt, ester, or prodrug thereof, wherein:

Z is —CH$_2$—, —CH$_2$CH$_2$—, —O—, —S—, —S(O)—, —S(O$_2$)—, or —N(R$_7$)—;

R$_1$, R$_3$, and R$_5$ each represent independently for each occurrence hydrogen, halogen, hydroxyl, amino, C$_1$-C$_6$alkyl, C$_1$-C$_6$alkoxy, C$_1$-C$_6$alkoxy-C$_1$-C$_6$alkyl, C$_1$-C$_6$alkanoyl, C$_1$-C$_6$alkylsulfinyl, C$_1$-C$_6$alkylsulfinyl-C$_1$-C$_6$alkyl, C$_1$-C$_6$alkylsulfonyl, C$_1$-C$_6$alkylsulfonyl-C$_1$-C$_6$alkyl, aryl, aralkyl, heterocycloalkyl, heteroaryl, or heteroaralkyl;

R$_2$ and R$_4$ are C$_1$-C$_6$alkoxy;

R$_6$ is —C(O)R$_8$, —C(S)R$_8$, —C(O)OR$_8$, —C(O)NR$_8$R$_9$, —C(S)NR$_8$R$_9$, —C(NH)R$_8$, or —S(O$_2$)R$_8$;

R$_7$ is alkyl, aralkyl, or heteroaralkyl;

R$_8$ and R$_9$ each represent independently hydrogen, C$_1$-C$_6$alkyl, heteroalkyl, aryl, heteroaryl, aralkyl, or heteroaralkyl; and n represents independently for each occurrence 0, 1, or 2.

In each of the foregoing methods and compositions, the necrostatin can be a Nec-4 related compound of Formula IV:

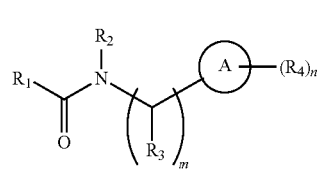

(IV)

or a pharmaceutically acceptable salt, ester, or prodrug thereof, wherein:

R$_1$ is

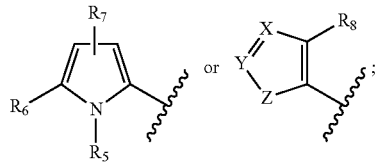

R$_2$ and R$_3$ each represent independently for each occurrence hydrogen or methyl;

R$_4$ represents independently for each occurrence halogen, hydrogen, C$_1$-C$_6$alkyl, C$_2$-C$_6$alkenyl, or C$_2$-C$_4$alkynyl;

R$_5$ is C$_1$-C$_4$alkyl;

R$_6$ is hydrogen, halogen, or —CN;

R$_7$ is hydrogen or C$_1$-C$_4$alkyl;

R$_8$ is C$_1$-C$_6$alkyl, or R$_8$ taken together with R$_9$, when present, forms a carbocyclic ring;

R$_9$ is hydrogen or C$_1$-C$_6$alkyl, or R$_9$ taken together with R$_8$ forms a carbocyclic ring;

R$_{10}$ is hydrogen or C$_1$-C$_6$alkyl;

A is phenylene or a 5-6 membered heteroarylene;

X is N or —C(R$_9$)—;

Y is N or —C(R$_{10}$)—;

Z is S or O; and m and n each represent independently 1, 2, or 3.

In each of the foregoing methods and compositions, the necrostatin can be a Nec-4 related compound of Formula IV-A:

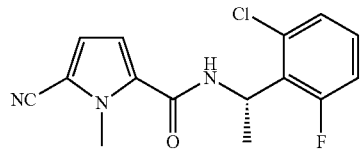 [SMILES: C[C@H](NC(=O)c1ccc(C#N)n1C)c1c(F)cccc1Cl]

or a pharmaceutically acceptable salt thereof.

In each of the foregoing methods and compositions, the necrostatin can be a Nec-5 related compound of Formula V:

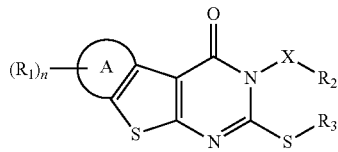

or a pharmaceutically acceptable salt, ester, or prodrug thereof, wherein:

A is a saturated or unsaturated 5-6 membered carbocyclic ring;

X is a bond or $C_1$-$C_4$alkylene;

$R_1$ is $C_1$-$C_6$ alkyl, halogen, hydroxyl, $C_1$-$C_6$alkoxyl, —N($R_4$)$_2$, —C(O)$R_4$, CO$_2$$R_4$, or C(O)N($R_4$)$_2$;

$R_2$ is

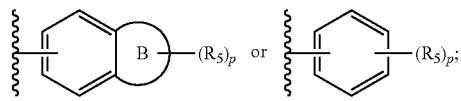

$R_3$ is —$C_1$-$C_6$alkylene-CN, —CN, $C_1$-$C_6$alkyl, or $C_2$-$C_6$alkenyl;

$R_4$ represents independently for each occurrence hydrogen, $C_1$-$C_6$alkyl, aryl, or aralkyl;

$R_5$ represents independently for each occurrence $C_1$-$C_6$alkyl, halogen, hydroxyl, $C_1$-$C_6$alkoxyl, —N($R_4$)$_2$, —C(O)$R_4$, CO$_2$$R_4$, or C(O)N($R_4$)$_2$;

B is a 5-6 membered heterocyclic or carbocylic ring; and n and p each represent independently 0, 1, or 2.

In each of the foregoing methods and compositions, the necrostatin can be a Nec-5 related compound of Formula V-A:

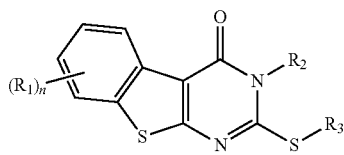

or a pharmaceutically acceptable salt, ester, or prodrug thereof, wherein:

$R_1$ is $C_1$-$C_6$alkyl, halogen, hydroxyl, $C_1$-$C_6$alkoxyl, or —N($R_4$)$_2$;

$R_2$ is

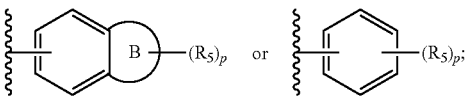

$R_3$ is —$C_1$-$C_6$alkylene-CN;

$R_4$ represents independently for each occurrence hydrogen, $C_1$-$C_6$alkyl, aryl, or aralkyl;

$R_5$ represents independently for each occurrence $C_1$-$C_6$alkyl, halogen, hydroxyl, $C_1$-$C_6$alkoxyl, —N($R_4$)$_2$, —C(O)$R_4$, CO$_2$$R_4$, or C(O)N($R_4$)$_2$;

B is a 5-6 membered heterocyclic or carbocylic ring; and n and p each represent independently 0, 1, or 2.

In each of the foregoing methods and compositions, the necrostatin can be a Nec-7 related compound of Formula VII:

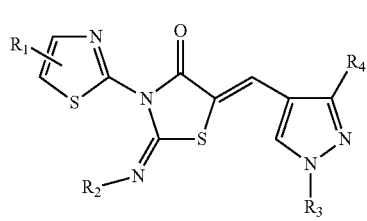

or a pharmaceutically acceptable salt, ester, or prodrug thereof, wherein:

$R_1$, $R_2$, and $R_3$ each represent independently hydrogen or $C_1$-$C_4$alkyl;

$R_4$ is

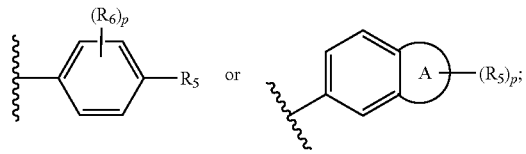

$R_5$ and $R_6$ each represent independently for each occurrence halogen, $C_1$-$C_6$alkyl, hydroxyl, $C_1$-$C_6$alkoxyl, —N($R_7$)$_2$, —NO$_2$, —S—$C_1$-$C_6$alkyl, —S-aryl, —SO$_2$—$C_1$-$C_6$alkyl, —SO$_2$-aryl, —C(O)$R_7$, —CO$_2$$R_7$, —C(O)N($R_7$)$_2$, heterocycloalkyl, aryl, or heteroaryl;

$R_7$ represents independently for each occurrence hydrogen, $C_1$-$C_6$alkyl, aryl, or aralkyl; or two occurrences of $R_7$ attached to the same nitrogen atom are taken together with the nitrogen atom to which they are attached to form a 3-7 membered heterocyclic ring;

A is a 5-6 membered heterocyclic ring; and p is 0, 1, or 2.

In each of the foregoing methods and compositions, the necrostatin can be a Nec-7 related compound of Formula VIII:

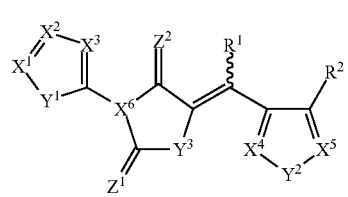

or a pharmaceutically acceptable salt, ester, or prodrug thereof, wherein:

each $X^1$, $X^2$, $X^3$, $X^4$, $X^5$, and $X^6$ is selected, independently, from N or CR$^{X1}$;

each $Y^1$, $Y^2$, and $Y^3$ is selected, independently, from O, S, NR$^{Y1}$, or CR$^{Y2}$R$^{Y3}$;

each $Z^1$ and $Z^2$ is selected, independently, from O, S, or NR$^{Z1}$;

each R$^{Y1}$ and R$^{Z1}$ is selected, independently, from H, optionally substituted $C_{1-6}$alkyl, optionally substituted $C_{2-6}$alkenyl, optionally substituted $C_{2-6}$alkynyl, optionally substituted cycloalkyl, optionally substituted heterocyclyl, optionally substituted aryl, optionally substituted heteroaryl, —C(=O)$R^{5A}$, —C(=O)O$R^{5A}$, or —C(=O)N$R^{5A}R^{6A}$;

each $R^{X1}$, $R^{Y2}$, and $R^{Y3}$ is selected, independently, from H, halogen, CN, NC, $NO_2$, $N_3$, $OR^3$, $SR^3$, $NR^3R^4$, —C(=O)$R^{5A}$, —C(=O)O$R^{5A}$, —C(=O)N$R^{5A}R^{6A}$, —S(=O)$R^{5A}$, —S(O)$_2R^{5A}$, —S(=O)$_2OR^{5A}$, —S(=O)$_2NR^{5A}R^{6A}$, optionally substituted $C_{1-6}$alkyl, optionally substituted $C_{2-6}$alkenyl, optionally substituted $C_{2-6}$alkynyl, optionally substituted cycloalkyl, optionally substituted heterocyclyl, optionally substituted aryl, or optionally substituted heteroaryl;

each $R^1$, $R^2$, $R^{5A}$, $R^{5B}$, $R^{6A}$, and $R^{6B}$ is selected from H, optionally substituted $C_{1-6}$ alkyl, optionally substituted $C_{2-6}$alkenyl, optionally substituted $C_{2-6}$alkynyl, optionally substituted cycloalkyl, optionally substituted heterocyclyl, optionally substituted aryl, or optionally substituted heteroaryl; or $R^{5A}$ and $R^{6A}$, or $R^{5B}$ and $R^{6B}$ combine to form a heterocyclyl; and each $R^3$ and $R^4$ is selected from H, optionally substituted $C_{1-6}$ alkyl, optionally substituted cycloalkyl, optionally substituted heterocyclyl, optionally substituted aryl, optionally substituted heteroaryl, —C(=O)$R^{5B}$, —C(=S)$R^{5B}$, —C(=N$R^{6B}$)$R^{5B}$, —C(=O)O$R^{5B}$, —C(=O)N$R^{5B}R^{6B}$, —S(=O)$R^{5B}$, —S(=O)$_2R^{5B}$, —S(=O)$_2OR^{5B}$ or —S(=O)$_2$N$R^{5B}R^{6B}$. In certain embodiments when $R^1$ is H, $X^1$, $X^2$, and $X^4$ are each CH, $X^3$, $X^5$, and $X^6$ are each N, $Y^1$ and $Y^3$ are each S, $Y^2$ is NH, $Z^1$ is NH, and $Z^2$ is O, then $R^2$ is not 4-fluorophenyl.

In each of the foregoing methods and compositions, the necrostatin can be a Nec-4 related compound of Formula IX:

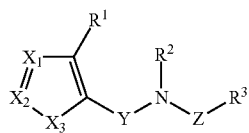

(IX)

or a pharmaceutically acceptable salt, ester, or prodrug thereof, wherein:

$X_1$ and $X_2$ are, independently, N or $CR^4$;

$X_3$ is selected from O, S, $NR^5$, or —$(CR^5)_2$;

Y is selected from C(O) or $CH_2$; and

Z is $(CR^6R^7)$—;

$R^1$ is selected from H, halogen, optionally substituted $C_{1-6}$alkyl, or optionally substituted $C_{1-6}$cycloalkyl, or optionally substituted aryl;

$R^2$ is selected from H or optionally substituted $C_{1-6}$alkyl;

$R^3$ is optionally substituted aryl;

each $R^4$ is selected from H, halogen, carboxamido, nitro, cyano, optionally substituted $C_{1-6}$alkyl, or optionally substituted aryl;

$R^5$ is selected from H, halogen, optionally substituted $C_{1-6}$alkyl, or optionally substituted aryl;

each $R^6$ and $R^7$ is, independently, selected from H, optionally substituted $C_{1-6}$alkyl, or aryl; and n is 0, 1, 2, or 3. In certain embodiments, when $X_1$ and $X_2$ are N, $X_3$ is S, Y is C(O), Z is $CH_2$, $R^2$ is H, and $R^3$ is 2-chloro-6-fluoro-phenyl, then $R^1$ is not methyl.

The foregoing aspects and embodiments of the invention may be more fully understood by reference to the following figures, detailed description and claims.

BRIEF DESCRIPTION OF THE DRAWINGS

The objects and features of the invention may be more fully understood by reference to the drawings described herein.

FIGS. 3A-E show longitudinal sections of the optic nerve stained with an antibody against βIII-tubulin, following optic nerve crush injury. The vertical arrows denote the locations of the injury sites, and the horizontal reference lines denote regions where axon regeneration were detected following treatment with Nec-1 and ZVAD (FIGS. 3D-E versus FIGS. 3A-C).

DETAILED DESCRIPTION

The invention relates to methods for preserving neuron viability and/or promoting axon regeneration and nerve function in a subject affected with a CNS disorder such as a traumatic CNS injury (e.g., traumatic brain injury or spinal cord injury) or a neurodegenerative disease (e.g., dementia, stroke, Alzheimer's disease, Parkinson's disease, and Huntington's disease). Using the methods described herein, it may be possible, for example, to reduce the loss of cognitive, sensory, and motor functions associated with the CNS disorder.

Figure 1:
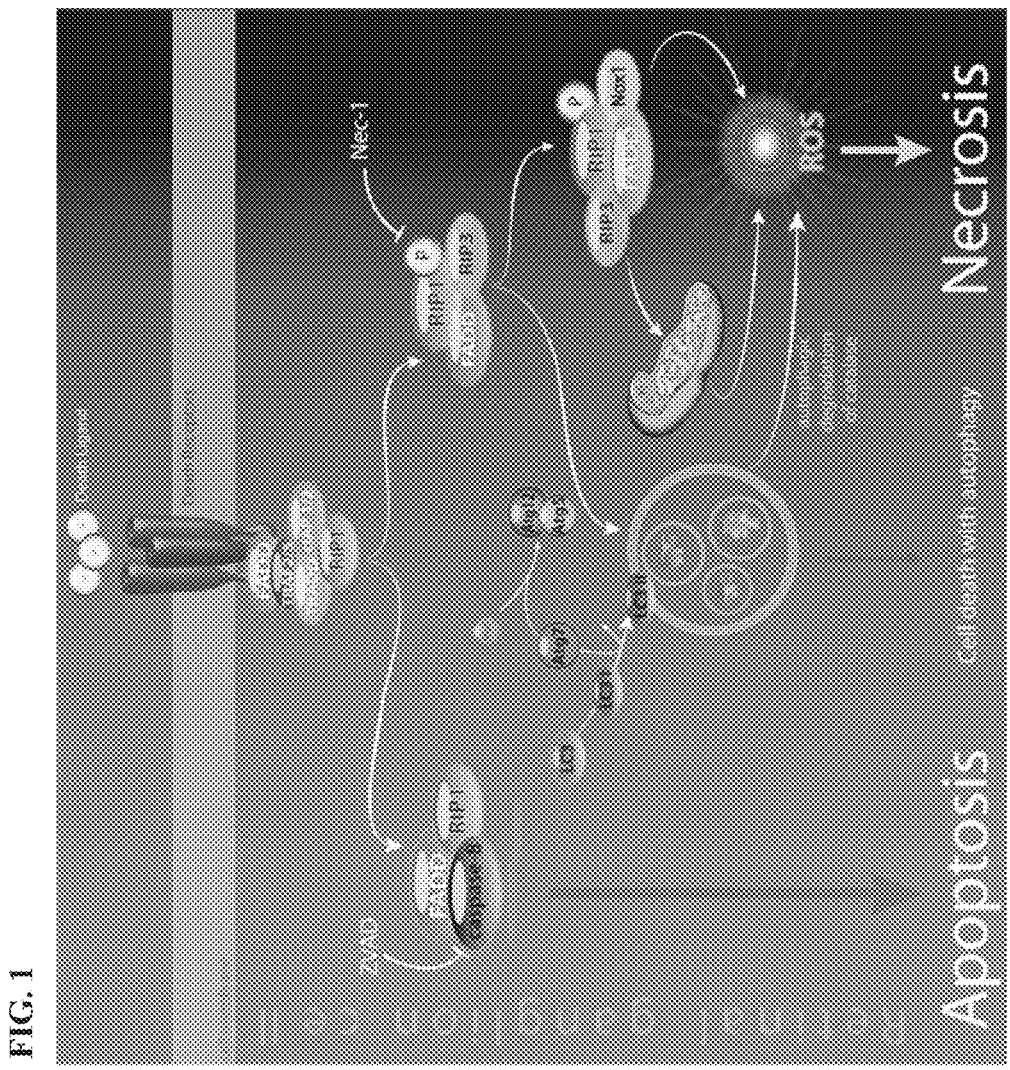
FIG. 1 provides a schematic diagram showing proposed mechanisms of retinal ganglion cell death.

The invention is based, in part, on the discovery that a combination of a necrosis inhibitor (e.g., a RIPK inhibitor, e.g., a necrostatin) and an apoptosis inhibitor (e.g., a pan-caspase inhibitor, e.g., ZVAD or IDN-6556) induced axon regeneration in retinal ganglion cells (RGCs). Retinal ganglion cells (RGCs) are CNS neurons whose cell bodies reside in the retina and whose axons constitute the sole neuronal component of the optic nerve. It is thus contemplated that programmed necrosis may be a critical mechanism of neuronal cell death and axon degeneration in CNS disorders such as, for example, brain injury (e.g., traumatic brain injury), spinal cord injury, dementia, stroke, Alzheimer's disease, Parkinson's disease, and Huntington's disease. Without wishing to be bound by theory, but as depicted in FIG. 1, there are two proposed pathways for cell death (apoptosis and necrosis), in a retinal ganglion cell, which appear to be mediated by RIP-1, a serine/threonine kinase. RIP1 forms a death inducing signaling complex with Fas-associated domain (FADD) and caspase-8, thereby activating caspase-8 and the downstream cascade leading to apoptosis. On the other hand, when caspase pathway is blocked (for example, with a caspase inhibitor such as ZVAD), RIP1 kinase is activated in a RIP1-RIP3 complex and promotes RGC necrosis. Thus, RIP Kinases act as common intermediaries for various upstream death signals, and their blockade in addition to caspase inhibition provides effective neuroprotection.

The methods described herein are directed to therapies that target both the necrotic and apoptotic pathways of programmed cell death. In particular, the methods disclosed herein facilitate a combination therapy where a necrosis inhibitor, e.g., a necrostatin (e.g., necrostatin-1 or necrostatin-4), can be administered either alone or in combination (either sequentially or simultaneously) with an apoptosis inhibitor e.g., a pan-caspase inhibitor (e.g., ZVAD or IDN- 6556). In certain embodiments, the disclosed methods surprisingly use necrostatins at concentrations higher than those previously thought to be clinically tolerable. It is contemplated that the combination of a necrostatin, e.g., necrostatin-1 or necrostatin-4, and a pan-caspase inhibitor, e.g., ZVAD or IDN-6556, produces a superior effect in promoting axon regeneration in a CNS neuron. It is further contemplated that the combination treatment of a necrostatin and a pan-caspase inhibitor preserves neuron viability and promotes nerve function in a CNS neuron following CNS injury.

Provided herein are methods for promoting neuron survival and axon regeneration in the CNS. CNS disorders characterized by impaired or failing axon growth or axon degeneration may arise from CNS neuron injury (e.g., trauma, surgery, nerve compression, nerve contusion, nerve transection, neurotoxicity, or other physical injury to the brain or spinal cord) or neurodegenerative CNS disease, wherein a symptom of the disorder is axon degeneration (e.g., Alzheimer's disease, amyotropic lateral sclerosis (ALS/Lou Gehrig's Disease), Parkinson's disease, multiple sclerosis, diabetic neuropathy, polyglutamine (polyQ) diseases, and stroke, Fahr disease, Menke's disease, Wilson's disease, cerebral ischemia, prion disorder (e.g., Creutzfeldt-Jakob disease). In an exemplary embodiment, the CNS disorder is brain injury (e.g., traumatic brain injury) or spinal cord injury (e.g., chronic, acute, or traumatic spinal cord injury). In another embodiment, the CNS disorder affects a subject's basic vital life functions such as breathing, heart beat and blood pressure, e.g., an injury to or aneurysm in the brain stem.

For convenience, certain terms in the specification, examples, and appended claims are collected in this section.

As used herein, "neuron," "neuronal cell" or "neural cell" refer to nerve cells, i.e., cells that are responsible for conducting nerve impulses from one part of the body to another. Most neurons consist of three distinct portions: a cell body, soma or perikaryon, which contains a nucleus and two kinds of cytoplasmic processes: dendrites and axons. Dendrites are usually highly branched, thick extensions of the cytoplasm of the cell body. An axon is usually a single long, thin process that is highly specialized and conducts nerve impulses away from the cell body to another neuron or muscular or glandular tissue. Along the length of an axon, there may be side branches called "axon collaterals." Axon collaterals and axons may terminate by branching into many fine filaments called "axon terminals." The distal ends of axon terminals are called "synaptic end bulbs," which contain synaptic vesicles that store neurotransmitters. Axons may be surrounded by a multilayered, white, phospholipid, segmented covering called the myelin sheath. Axons containing such a covering are "myelinated."

As used herein, the term "cell death" is understood to mean the death of a cell, for example, by apoptosis or necrosis.

As used herein, the term "apoptosis" is understood to mean caspase-dependent cell death, which is characterized by any of the following properties: cell shrinkage, nuclear condensation, DNA fragmentation or membrane blebbing.

As used herein, the term "apoptosis inhibitor" is understood to mean any agent that, when administered to a mammal, reduces apoptotic cell death in a cell. For example, it is understood that certain useful apoptosis inhibitors act by reducing or eliminating the activity of one or more members of the intrinsic or extrinsic or common apoptotic pathways. Furthermore, it is understood that an agent that either directly or indirectly affects the activity of one or more caspases (e.g., a pan-caspase inhibitor) is considered to be an apoptosis inhibitor. It is understood that a caspase inhibitor can affect the activity of a caspase either directly by modulating a specific caspase in the apoptotic pathway or indirectly by modulating a downstream caspase present in the apoptotic pathway.

As used herein, the term "pan-caspase inhibitor" is understood to mean a broad-spectrum caspase inhibitor that inhibits at least two, preferably at least three different caspases (e.g., caspase-1, caspase-2, caspase-3, caspase-4, caspase-5, caspase-6, caspase-7, caspase-8, caspase-9, caspase-10, caspase-11, caspase-12, caspase-13, and/or caspase-14. ZVAD (also known as Z-VAD, Benzyloxycarbonyl-Val-Ala-Asp(OMe)-fluoromethylketone and carbobenzoxy-valyl-alanyl-aspartyl-[O-methyl]-fluoromethylketone) is an exemplary pan-caspase inhibitor and is available from R&D Systems (Cat. No. FMK001) and Promega (Cat. No. G7231). Other exemplary pan-caspase inhibitors that may be used include IDN-6556 (also known as "PF-3,491,390") available from Conatus Pharmaceuticals, Inc. (formerly Idun Pharmaceuticals, Inc.), VX-799 available from Vertex Pharmaceuticals, Inc., MX1013 available Maxim Pharmaceuticals, Inc., Xyz033mp available from LG Chemical, Inc., all of which are described, for example, in Linton, S. D. (2005) CURRENT TOPICS IN MEDICAL CHEM. 5:1697-1717. It is understood that a "pan-caspase inhibitor" may also be a cocktail (e.g., a combination) of caspase inhibitors including two or more of specific caspase inhibitors (e.g., synthetic or endogenous caspase inhibitors).

As used herein, the term "necrosis" is understood to mean caspase-independent cell death characterized by any of the following properties: cellular and/or organelle swelling, plasma membrane rupture, or discontinuity in plasma, nuclear and/or organelle membranes. As used herein, the terms "necroptosis" and "programmed necrosis" refer to a form of necrosis and is understood to mean one form of programmed or regulated necrosis, and in certain embodiments, necroptosis is mediated by the serine/threonine kinase activity of receptor interacting protein (RIP) kinases, for example, RIP-1 kinase and/or RIP-3 kinase.

As used herein, the term "necrosis inhibitor" is understood to mean an agent, which, when administered to a mammal, reduces necrotic cell death in a cell. For example, it is understood that certain necrosis inhibitors act by reducing or inhibiting necroptosis or programmed necrosis. A necrosis inhibitor can be an agent that modulates the production and/or activity of one or more RIP kinases (e.g., RIP-1 kinase and/or RIP-3 kinase). For example, an inhibitor of RIP-1 kinase is understood to modulate the activity of RIP-1 kinase as well as downstream RIP kinases, e.g., RIP-3 kinase, in the necrosis cascade. Accordingly, a RIP-1 kinase inhibitor is also understood to modulate RIP-3 kinase activity.

As used herein, the term "necrostatin" or "nec" is understood to mean an inhibitor of caspase-independent cell death or necroptosis. Exemplary necrostatins include necrostatin-1 ("Nec-1"), necrostatin-2 ("Nec-2"), necrostatin-3 ("Nec-3"), necrostatin-4 ("Nec-4"), necrostatin-5 ("Nec-5") and necrostatin-7 ("Nec-7").

In certain embodiments, the necrostatin is a Nec-1 related compound of Formula I:

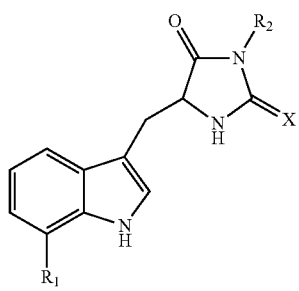

(I)

or a pharmaceutically acceptable salt, ester, or prodrug thereof, wherein

X is O or S;

$R_1$ is hydrogen, $C_1$-$C_6$alkyl, $C_1$-$C_6$alkoxyl, or halogen; and $R_2$ is hydrogen or $C_1$-$C_6$alkyl.

In certain embodiments, X is O. In certain embodiments, $R_1$ is hydrogen or halogen (such as chlorine). In certain embodiments, $R_2$ is a methyl or ethyl. In certain other embodiments, $R_1$ is hydrogen or Cl, and $R_2$ is a methyl.

In certain embodiments, the necrostatin is a Nec-1 related compound of Formula I-A, shown below:

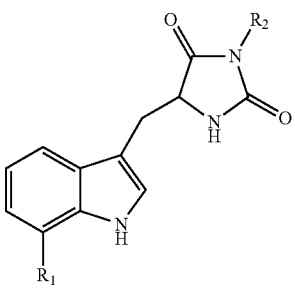

(I-A)

or a pharmaceutically acceptable salt, ester, or prodrug thereof, or optical isomers or racemic mixtures thereof, wherein $R_1$ is H, alkyl, alkoxyl, or a halogen (for example, F, Cl, Br or I) and $R_2$ is H or an alkyl. In certain embodiments, $R_1$ is H or Cl. In certain other embodiments, $R_2$ is a methyl or ethyl. In certain other embodiments, $R_1$ is H or Cl, and $R_2$ is a methyl.

In certain other embodiments, the necrostatin is a Nec-1 related compound of Formula I-B, shown below:

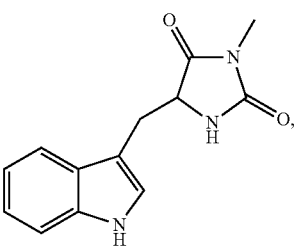

(I-B)

or a pharmaceutically acceptable salt, ester, or prodrug thereof.

In certain other embodiments, the necrostatin is a Nec-1 related compound of Formula I-C, shown below:

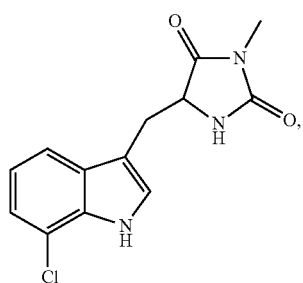

(I-C)

or a pharmaceutically acceptable salt, ester, or prodrug thereof.

In certain other embodiments, the necrostatin is a Nec-1 related compound of Formula I-D, shown below:

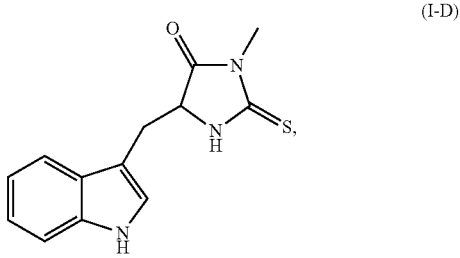 [SMILES: CN1C(=O)C(Cc2c[nH]c3ccccc23)NC1=S]

(I-D)

or a pharmaceutically acceptable salt, ester, or prodrug thereof.

In certain other embodiments, the necrostatin is a Nec-1 related compound of Formula I-E, shown below:

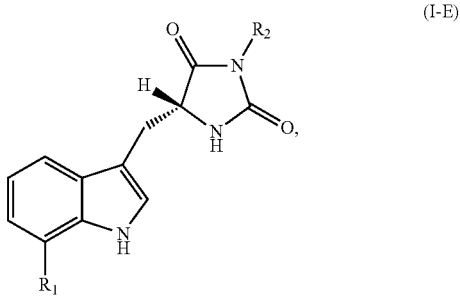

(I-E)

or a pharmaceutically acceptable salt, ester, or prodrug thereof, wherein $R_1$ is H, alkyl, alkoxyl, or a halogen (for example, F, Cl, Br or I) and $R_2$ is H or an alkyl. In certain embodiments, $R_1$ is H or Cl. In certain other embodiments, $R_2$ is a methyl or ethyl. In certain other embodiments, $R_1$ is H or Cl, and $R_2$ is a methyl.

In certain other embodiments, the necrostatin is a Nec-1 related compound of Formula I-F, shown below:

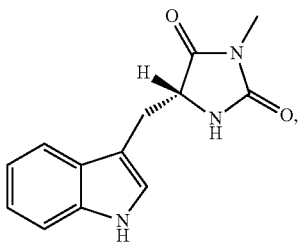

(I-F)

or a pharmaceutically acceptable salt, ester, or prodrug thereof. In certain other embodiments, the necrostatin is a Nec-1 related compound of Formula I-G, shown below:

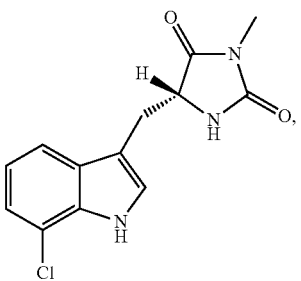

(I-G)

or a pharmaceutically acceptable salt, ester, or prodrug thereof.

The Nec-1 related compounds described above can be prepared based on synthetic procedures described in the literature, such as in Degterev et al., in *Nature Chemical Biology*, (2005), vol. 1, 112-119; Degterev et al., in *Nature Chemical Biology*, (2008), vol. 4, 313-321; and International Patent Application Publication No. WO 2007/075772, all of which are hereby incorporated by reference.

In certain embodiments, the necrostatin is a Nec-2 related compound of Formula II:

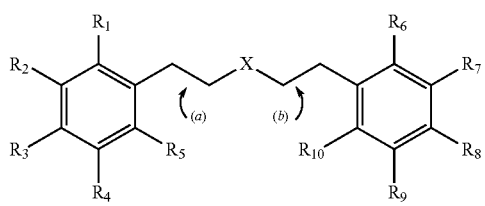

(II)

or a pharmaceutically acceptable salt, ester, or prodrug thereof, wherein:

X is —$CH_2$—, —C(H)($R_{14}$)—, —C(=S)—, —C(=NH)—, or —C(O)—;

$R_1$, $R_2$, $R_3$, $R_4$, $R_5$, $R_6$, $R_7$, $R_8$, $R_9$, and $R_{10}$ each represent independently hydrogen, acyl, acetyl, alkyl, halogen, amino, $C_1$-$C_6$alkoxyl, nitro, —C(O)$R_{12}$, —C(S)$R_{12}$, —C(O)O$R_{12}$, —C(O)N$R_{12}R_{13}$, —C(S)N$R_{12}R_{13}$, or —S($O_2$)$R_{12}$;

$R_{11}$ is hydrogen, acyl, acetyl, alkyl, or acylamino;

$R_{12}$ and $R_{13}$ each represent independently hydrogen, an optionally substituted alkyl, an optionally substituted aryl, an optionally substituted heteroaryl, an optionally substituted aralkyl, or an optionally substituted heteroaralkyl;

$R_{14}$ is acyl, acetyl, alkyl, halogen, amino, acylamino, nitro, —S$R_{11}$, —N($R_{11}$)$_2$, or —O$R_{11}$;

the bond indicated by (a) can be a single or double bond; and the bond indicated by (b) can be a single or double bond.

In certain embodiments, X is —C(O)—. In certain embodiments, $R_1$, $R_2$, $R_5$, $R_6$, $R_7$, and $R_{10}$ each represent independently hydrogen, acyl, alkyl, halogen, or amino. In certain embodiments, $R_3$, $R_4$, $R_8$, and $R_9$ are $C_1$-$C_6$alkoxyl. In certain embodiments, the bond indicated by (a) is a double bond; and the bond indicated by (b) is a double bond. In certain embodiments, when each of $R_1$, $R_4$, $R_5$, $R_6$, $R_9$ and $R_{10}$ is hydrogen and each of $R_2$, $R_3$, $R_7$, and $R_8$ is methoxyl, then X is not —C(O)—, —$CH_2$—, or —CH(OH)—.

In certain other embodiments, the necrostatin is a Nec-2 related compound of Formula II-A:

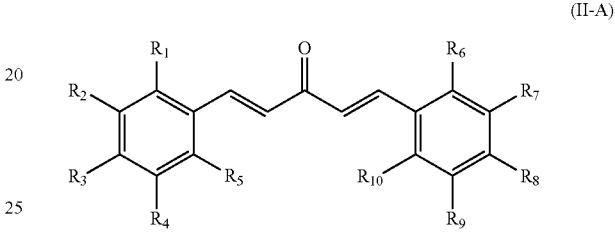

(II-A)

or a pharmaceutically acceptable salt thereof, wherein:

$R_1$, $R_2$, $R_5$, $R_6$, $R_7$, and $R_{10}$ each represent independently hydrogen, alkyl, halogen, amino, or methoxyl; and $R_3$, $R_4$, $R_8$, and $R_9$ are $C_1$-$C_6$alkoxyl.

In certain other embodiments, the Nec-2 related compound is

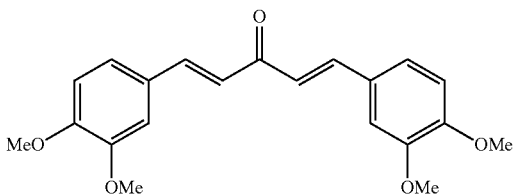 [SMILES: COc1ccc(/C=C/C(=O)/C=C/c2ccc(OC)c(OC)c2)cc1OC]

or a pharmaceutically acceptable salt thereof.

The Nec-2 related compounds described above can be prepared based on synthetic procedures described in the literature, such as in International Patent Application Publication No. WO 2007/075772, which is hereby incorporated by reference.

In certain embodiments, the necrostatin is a Nec-3 related compound of Formula III:

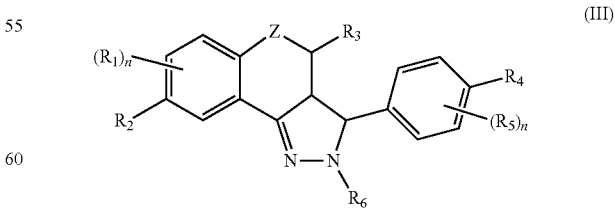

(III)

or a pharmaceutically acceptable salt, ester, or prodrug thereof, wherein:

Z is —$CH_2$—, —$CH_2CH_2$—, —O—, —S—, —S(O)—, —S($O_2$)—, or —N($R_7$)—;

$R_1$, $R_3$, and $R_5$ each represent independently for each occurrence hydrogen, halogen, hydroxyl, amino, $C_1$-$C_6$alkyl, $C_1$-$C_6$alkoxy, $C_1$-$C_6$alkoxy-$C_1$-$C_6$alkyl, $C_1$-$C_6$alkanoyl, $C_1$-$C_6$alkylsulfinyl, $C_1$-$C_6$alkylsulfinyl-$C_1$-$C_6$alkyl, $C_1$-$C_6$alkylsulfonyl, $C_1$-$C_6$alkylsulfonyl-$C_1$-$C_6$alkyl, aryl, aralkyl, heterocycloalkyl, heteroaryl, or heteroaralkyl;

$R_2$ and $R_4$ are $C_1$-$C_6$alkoxy;

$R_6$ is —C(O)$R_8$, —C(S)$R_8$, —C(O)O$R_8$, —C(O)N$R_8R_9$, —C(S)N$R_8R_9$, —C(NH)$R_8$, or —S(O$_2$)$R_8$;

$R_7$ is alkyl, aralkyl, or heteroaralkyl;

$R_8$ and $R_9$ each represent independently hydrogen, $C_1$-$C_6$alkyl, heteroalkyl, aryl, heteroaryl, aralkyl, or heteroaralkyl; and n represents independently for each occurrence 0, 1, or 2.

In certain embodiments, Z is —CH$_2$—. In certain embodiments, $R_1$, $R_3$, and $R_5$ each represent independently for each occurrence hydrogen, halogen, hydroxyl, amino, or $C_1$-$C_6$alkyl. In certain embodiments, $R_2$ and $R_4$ are methoxy. In certain embodiments, $R_6$ is C(O)$R_8$, and $R_8$ is $C_1$-$C_6$alkyl. In certain embodiments, $R_7$ is alkyl. In certain embodiments, $R_8$ and $R_9$ each represent independently hydrogen or $C_1$-$C_6$alkyl. In certain embodiments, n is 0.

In certain embodiments, the Nec-3 related compound is

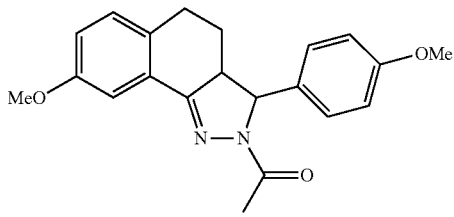 [SMILES: COc1ccc(C2C3CCc4ccc(OC)cc4C3=NN2C(C)=O)cc1]

or a pharmaceutically acceptable salt thereof.

In certain other embodiments, the Nec-3 related compound is

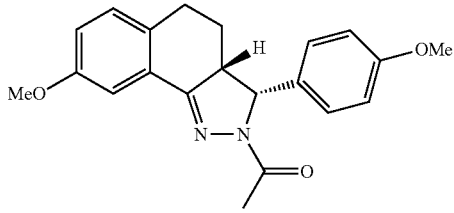 [SMILES: COc1ccc([C@H]2[C@H]3CCc4ccc(OC)cc4C3=NN2C(C)=O)cc1]

or a pharmaceutically acceptable salt thereof.

The Nec-3 related compounds described above can be prepared based on synthetic procedures described in the literature, such as in Degterev et al., in *Nature Chemical Biology*, (2008), vol. 4, 313-321; and International Patent Application Publication No. WO 2007/075772, both of which is hereby incorporated by reference.

In certain embodiments, the necrostatin is a Nec-4 related compound of Formula IV:

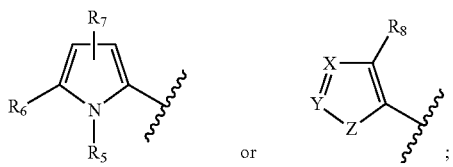

or a pharmaceutically acceptable salt, ester, or prodrug thereof, wherein:

$R_1$ is

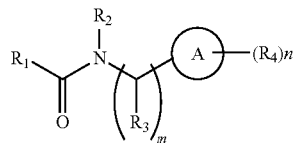

$R_2$ and $R_3$ each represent independently for each occurrence hydrogen or methyl;

$R_4$ represents independently for each occurrence halogen, hydrogen, $C_1$-$C_6$alkyl, $C_2$-$C_6$alkenyl, or $C_2$-$C_4$alkynyl;

$R_5$ is $C_1$-$C_4$alkyl;

$R_6$ is hydrogen, halogen, or —CN;

$R_7$ is hydrogen or $C_1$-$C_4$alkyl;

$R_8$ is $C_1$-$C_6$alkyl, or $R_8$ taken together with $R_9$, when present, forms a carbocyclic ring;

$R_9$ is hydrogen or $C_1$-$C_6$alkyl, or $R_9$ taken together with $R_8$ forms a carbocyclic ring;

$R_{10}$ is hydrogen or $C_1$-$C_6$alkyl;

A is phenylene or a 5-6 membered heteroarylene;

X is N or —C($R_9$)—;

Y is N or —C($R_{10}$)—;

Z is S or O; and m and n each represent independently 1, 2, or 3.

In certain embodiments, $R_1$ is

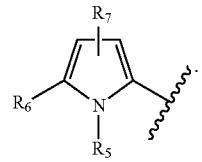

In certain other embodiments, $R_1$ is

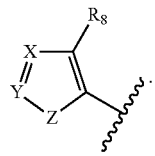

In certain embodiments, $R_2$ is hydrogen. In certain embodiments, $R_3$ is methyl. In certain other embodiments, $R_3$ is hydrogen. In certain embodiments, $R_4$ is halogen, such as fluorine or chlorine. In certain embodiments, $R_4$ is halogen. In certain embodiments, $R_5$ is methyl or ethyl. In certain embodiments, $R_6$ is —CN. In certain embodiments, A is phenylene. In certain embodiments, X is N. In certain embodiments, Y is N. In certain embodiments, Z is S. In certain embodiments, A is phenylene. In certain embodiments, $R_1$ is $C_1$-$C_6$alkyl, such as methyl. In certain embodiments, m is 1. In certain embodiments, n is 2.

In certain embodiments, the necrostatin is a Nec-4 related compound of Formula IV-A:

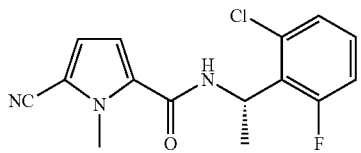 [SMILES: C[C@H](NC(=O)c1ccc(C#N)n1C)c1c(F)cccc1Cl]

or a pharmaceutically acceptable salt thereof.

In certain embodiments, the necrostatin is a Nec-4 related compound of Formula IV-B:

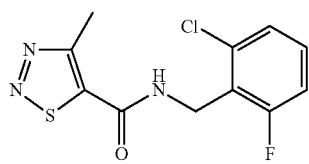 [SMILES: Cc1nnsc1C(=O)NCc1c(F)cccc1Cl]

or a pharmaceutically acceptable salt thereof.

The Nec-4 related compounds described above can be prepared based on synthetic procedures described in the literature, such as in Teng et al., (2007) BIOORG MED CHEM LETT, 17: 6836-6840; and Teng et al., (2008) BIOORG MED CHEM LETT, 18: 3219-3223, both of which are incorporated herein by reference.

In certain embodiments, the necrostatin is a Nec-5 related compound of Formula V:

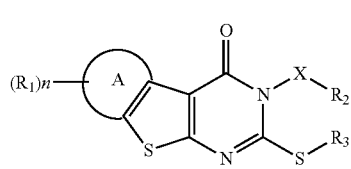

or a pharmaceutically acceptable salt, ester, or prodrug thereof, wherein:

A is a saturated or unsaturated 5-6 membered carbocyclic ring;

X is a bond or $C_1$-$C_4$alkylene;

$R_1$ is $C_1$-$C_6$alkyl, halogen, hydroxyl, $C_1$-$C_6$alkoxyl, —$N(R_4)_2$, —$C(O)R_4$, $CO_2R_4$, or $C(O)N(R_4)_2$;

$R_2$ is

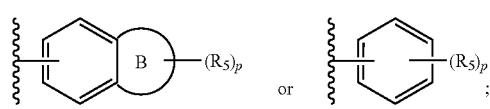

$R_3$ is —$C_1$-$C_6$alkylene-CN, —CN, $C_1$-$C_6$alkyl, or $C_2$-$C_6$alkenyl;

$R_4$ represents independently for each occurrence hydrogen, $C_1$-$C_6$alkyl, aryl, or aralkyl;

$R_5$ represents independently for each occurrence $C_1$-$C_6$alkyl, halogen, hydroxyl, $C_1$-$C_6$alkoxyl, —$N(R_4)_2$, —$C(O)R_4$, $CO_2R_4$, or $C(O)N(R_4)_2$;

B is a 5-6 membered heterocyclic or carbocyclic ring; and n and p each represent independently 0, 1, or 2.

In certain embodiments, X is a bond. In certain embodiments, A is an unsaturated 6-membered carbocyclic ring. In certain embodiments, $R_1$ is $C_1$-$C_6$alkyl, halogen, hydroxyl, or $C_1$-$C_6$alkoxyl. In certain embodiments, $R_2$ is

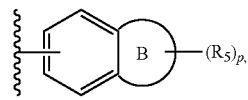

such as

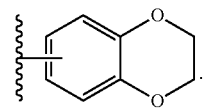

In certain embodiments, $R_3$ is —$C_1$-$C_6$alkylene-CN, such as —$CH_2$—CN. In certain embodiments, $R_4$ represents independently for each occurrence hydrogen or $C_1$-$C_6$alkyl. In certain embodiments, $R_5$ represents independently for each occurrence $C_1$-$C_6$alkyl, halogen, hydroxyl, or $C_1$-$C_6$alkoxyl. In certain embodiments, B is a 5-6 membered heterocyclic ring. In certain embodiments, n is 0. In certain embodiments, p is 0.

In certain embodiments, the necrostatin is a Nec-5 related compound of Formula V-A:

(V-A)

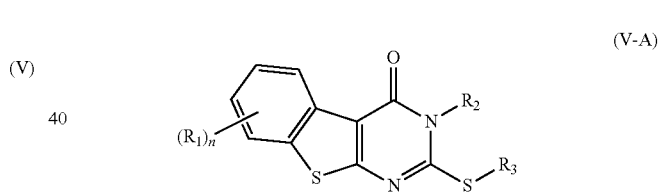

or a pharmaceutically acceptable salt, ester, or prodrug thereof, wherein:

$R_1$ is $C_1$-$C_6$alkyl, halogen, hydroxyl, $C_1$-$C_6$alkoxyl, or —$N(R_4)_2$;

$R_2$ is

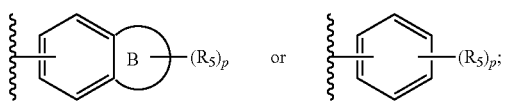

$R_3$ is —$C_1$-$C_6$alkylene-CN;

$R_4$ represents independently for each occurrence hydrogen, $C_1$-$C_6$alkyl, aryl, or aralkyl;

$R_5$ represents independently for each occurrence $C_1$-$C_6$alkyl, halogen, hydroxyl, $C_1$-$C_6$alkoxyl, —$N(R_4)_2$, —$C(O)R_4$, $CO_2R_4$, or $C(O)N(R_4)_2$;

B is a 5-6 membered heterocyclic or carbocyclic ring; and n and p each represent independently 0, 1, or 2.

In certain embodiments, the Nec-5 compound is

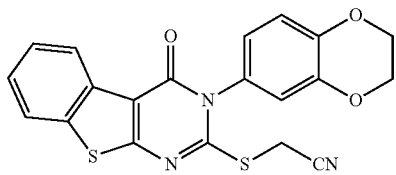 [SMILES: N#CCSc1nc2sc3ccccc3c2c(=O)n1-c1ccc2c(c1)OCCO2]

or a pharmaceutically acceptable salt thereof.

The Nec-5 related compounds described above can be prepared based on synthetic procedures described in the literature, such as in Degterev et al., in *Nature Chemical Biology*, (2008), vol. 4, 313-321; and International Patent Application Publication No. WO 2008/045406, both of which is hereby incorporated by reference.

In certain embodiments, the necrostatin is a Nec-7 related compound of Formula VII:

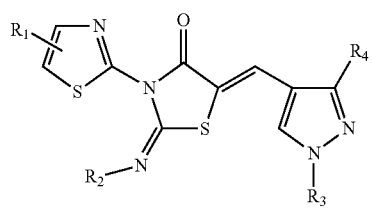

(VII)

or a pharmaceutically acceptable salt, ester, or prodrug thereof, wherein:

$R_1$, $R_2$, and $R_3$ each represent independently hydrogen or $C_1$-$C_4$alkyl;

$R_4$ is

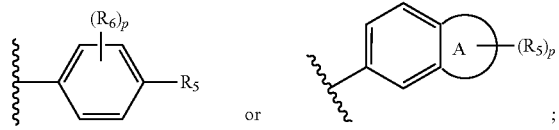

or ;

$R_5$ and $R_6$ each represent independently for each occurrence halogen, $C_1$-$C_6$alkyl, hydroxyl, $C_1$-$C_6$alkoxyl, —N($R_7$)$_2$, —NO$_2$, —S—$C_1$-$C_6$alkyl, —S-aryl, —SO$_2$—$C_1$-$C_6$alkyl, —SO$_2$-aryl, —C(O)$R_7$, —CO$_2$$R_7$, —C(O)N($R_7$)$_2$, heterocycloalkyl, aryl, or heteroaryl;

$R_7$ represents independently for each occurrence hydrogen, $C_1$-$C_6$alkyl, aryl, or aralkyl; or two occurrences of $R_7$ attached to the same nitrogen atom are taken together with the nitrogen atom to which they are attached to form a 3-7 membered heterocyclic ring;

A is a 5-6 membered heterocyclic ring; and p is 0, 1, or 2.

In certain embodiments, $R_1$ is hydrogen. In certain embodiments, $R_2$ is hydrogen. In certain embodiments, $R_3$ is hydrogen. In certain embodiments, $R_4$ is

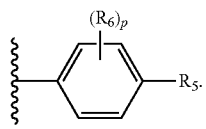

In certain embodiments, $R_5$ is halogen, $C_1$-$C_6$alkyl, hydroxyl, $C_1$-$C_6$alkoxyl, or —N($R_7$)$_2$. In certain other embodiments, $R_5$ is halogen, such as fluorine or chlorine. In certain embodiments, p is 0. In certain embodiments, $R_4$ is

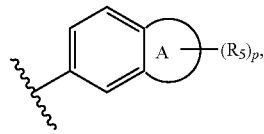

such as

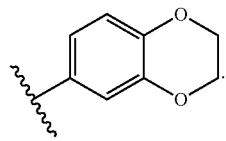 [SMILES: *c1ccc2c(c1)OCCO2]

In certain embodiments, the Nec-7 related compound is

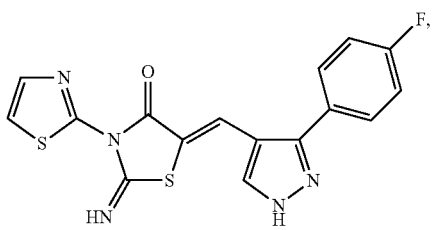 [SMILES: N=C1S/C(=C\c2c[nH]nc2-c2ccc(F)cc2)C(=O)N1c1nccs1]

or a pharmaceutically acceptable salt thereof.

The Nec-7 related compounds described above can be prepared based on synthetic procedures described in the literature, such as in Zheng et al., in BIOORG MED CHEM LETT, 2008, vol. 18, 4932-4935, which is incorporated herein by reference.

In certain embodiments, the necrostatin is a Nec-7 related compound of Formula VIII:

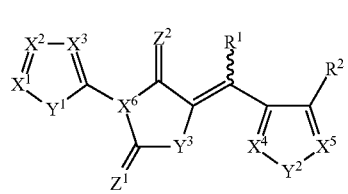

(VIII)

or a pharmaceutically acceptable salt, ester, or prodrug thereof, wherein:

each $X^1$, $X^2$, $X^3$, $X^4$, $X^5$, and $X^6$ is selected, independently, from N or $CR^{X1}$;

each $Y^1$, $Y^2$, and $Y^3$ is selected, independently, from O, S, $NR^{Y1}$, or $CR^{Y2}R^{Y3}$;

each $Z^1$ and $Z^2$ is selected, independently, from O, S, or $NR^{Z1}$;

each $R^{Y1}$ and $R^{Z1}$ is selected, independently, from H, optionally substituted $C_{1-6}$alkyl, optionally substituted $C_{2-6}$alkenyl, optionally substituted $C_{2-6}$alkynyl, optionally substituted cycloalkyl, optionally substituted heterocyclyl, optionally substituted aryl, optionally substituted heteroaryl, —C(=O)$R^{5A}$, —C(=O)O$R^{5A}$, or —C(=O)N$R^{5A}R^{6A}$;

each $R^{X1}$, $R^{Y2}$, and $R^{Y3}$ is selected, independently, from H, halogen, CN, NC, $NO_2$, $N_3$, $OR^3$, $SR^3$, $NR^3R^4$, —C(=O)$R^{5A}$, —C(=O)$OR^{5A}$, —C(=O)$NR^{5A}R^{6A}$, —S(=O)$R^{5A}$, —S(O)$_2R^{5A}$, —S(=O)$_2OR^{5A}$, —S(=O)$_2NR^{5A}R^{6A}$, optionally substituted $C_{1-6}$alkyl, optionally substituted $C_{2-6}$alkenyl, optionally substituted $C_{2-6}$alkynyl, optionally substituted cycloalkyl, optionally substituted heterocyclyl, optionally substituted aryl, or optionally substituted heteroaryl;

each $R^1$, $R^2R^{5A}$, $R^{5B}$, $R^{6A}$, and $R^{6B}$ is selected from H, optionally substituted $C_{1-6}$ alkyl, optionally substituted $C_{2-6}$alkenyl, optionally substituted $C_{2-6}$alkynyl, optionally substituted cycloalkyl, optionally substituted heterocyclyl, optionally substituted aryl, or optionally substituted heteroaryl; or $R^{5A}$ and $R^{6A}$, or $R^{5B}$ and $R^{6B}$ combine to form a heterocyclyl; and each $R^3$ and $R^4$ is selected from H, optionally substituted $C_{1-6}$ alkyl, optionally substituted cycloalkyl, optionally substituted heterocyclyl, optionally substituted aryl, optionally substituted heteroaryl, —C(=O)$R^{5B}$, —C(=S)$R^{5B}$, —C(=$NR^{6B}$)$R^{5B}$, —C(=O)$OR^{5B}$, —C(=O)$NR^{5B}R^{6B}$, —S(=O)$R^{5B}$, —S(=O)$_2R^{5B}$, —S(=O)$_2OR^{5B}$ or —S(=O)$_2 NR^{5B}R^{6B}$. In certain embodiments, when $R^1$ is H, $X^1$, $X^2$, and $X^4$ are each CH, $X^3$, $X^5$, and $X^6$ are each N, $Y^1$ and $Y^3$ are each S, $Y^2$ is NH, $Z^1$ is NH, and $Z^2$ is O, then $R^2$ is not 4-fluorophenyl.

In certain embodiments, the necrostatin is a Nec-7 related compound of Formula VIII-A:

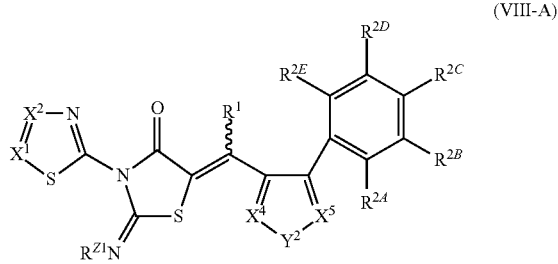

(VIII-A)

or a pharmaceutically acceptable salt, ester, or prodrug thereof, wherein:

$X^1$, $X^2$, $X^4$, $X^5$, $R^1$, $Y^2$, and $R^{Z1}$ are as defined for Formula (VIII);

each $R^{2A}$, $R^{2B}$, $R^{2C}$, $R^{2D}$, and $R^{2E}$ is selected, independently, from H, halogen, optionally substituted $C_{1-6}$ alkyl, optionally substituted $C_{2-6}$ alkenyl, optionally substituted $C_{2-6}$ alkynyl, optionally substituted cycloalkyl, optionally substituted heterocyclyl, optionally substituted aryl, optionally substituted heteroaryl, CN, NC, $NO_2$, $N_3$, $OR^7$, $SR^7$, S(=O)$R^{12}$, S(=O)$_2R^{12}$, S(=O)$OR^{12}$, S(=O)$_2OR^{12}$, $NR^7R^8$, C(=O)$R^{12}$, C(=O)$OR^{12}$, C(=O)$NR^{12}R^{13}$, C(=S)$R^{12}$, C(=S)$OR^{12}$, C(=S)$NR^{12}R^{13}$, C(=$NR^9$)$R^{12}$, C(=$NR^9$)$OR^{12}$, or C(=$NR^9$)$NR^{12}R^{13}$, or $R^{2A}$ and $R^{2B}$, $R^{2B}$ and $R^{2C}$, $R^{2C}$ and $R^{2D}$, or $R^{2D}$ and $R^{2E}$ combine to form an optionally substituted cycloalkyl or an optionally substituted heterocyclyl;

each $R^7$, $R^8$, and $R^9$ is selected, independently, from H, optionally substituted $C_{1-6}$ alkyl, optionally substituted cycloalkyl, optionally substituted heterocyclyl, optionally substituted aryl, optionally substituted heteroaryl, S(=O)$R^{10}$, S(=O)$_2R^{10}$, C(=O)$R^{10}$, C(=O)$OR^{10}$, C(=O)$NR^{10}R^{11}$, C(=S)$R^{10}$, C(S)$OR^{10}$, C(S)$NR^{10}R^{11}$, C(=$NR^{14}$)$R^{10}$, C(=$NR^{14}$)$OR^{10}$, or C(=$NR^{14}$)$NR^{10}R^{11}$, or $R^7$ and $R^8$ combine to form an optionally substituted heterocyclyl; and each $R^{10}$, $R^{11}$, $R^{12}$, $R^{13}$, and $R^{14}$ is selected, independently, from H, optionally substituted $C_{1-6}$alkyl, optionally substituted $C_{2-6}$alkenyl, optionally substituted $C_{2-6}$alkynyl, optionally substituted cycloalkyl, optionally substituted heterocyclyl, optionally substituted aryl, or optionally substituted heteroaryl, or $R^{10}$ and $R^{11}$ or $R^{12}$ and $R^{13}$ combine to form an optionally substituted heterocyclyl.

In certain embodiments, each $R^{2A}$, $R^{2B}$, $R^{2C}$, $R^{2D}$, and $R^{2E}$ is selected, independently, from H, halogen, $C_{1-6}$ alkyl, $C_{2-6}$ alkenyl, $C_{2-6}$ alkynyl, cycloalkyl, heterocyclyl, aryl, or heteroaryl.

In certain embodiments, the necrostatin is a Nec-7 related compound selected from:

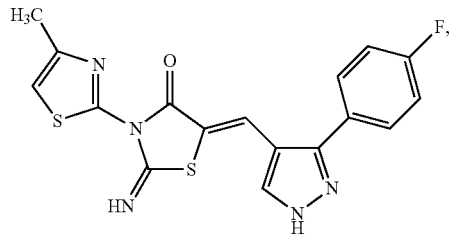

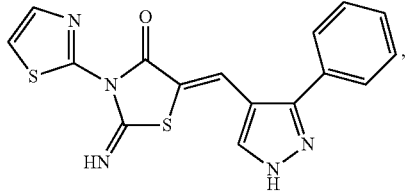

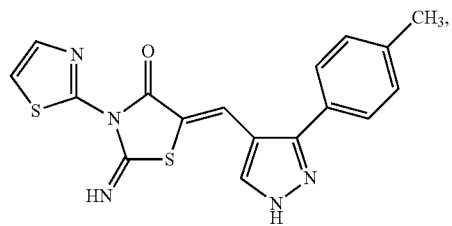

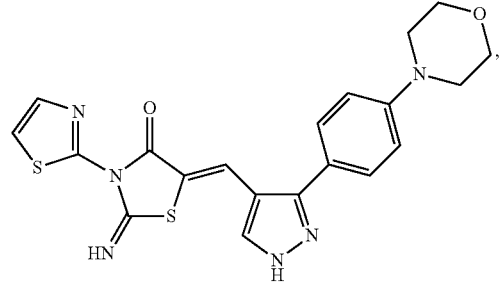

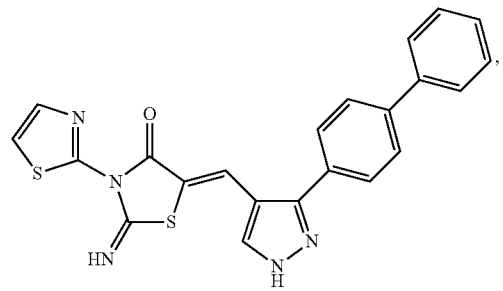

27

-continued

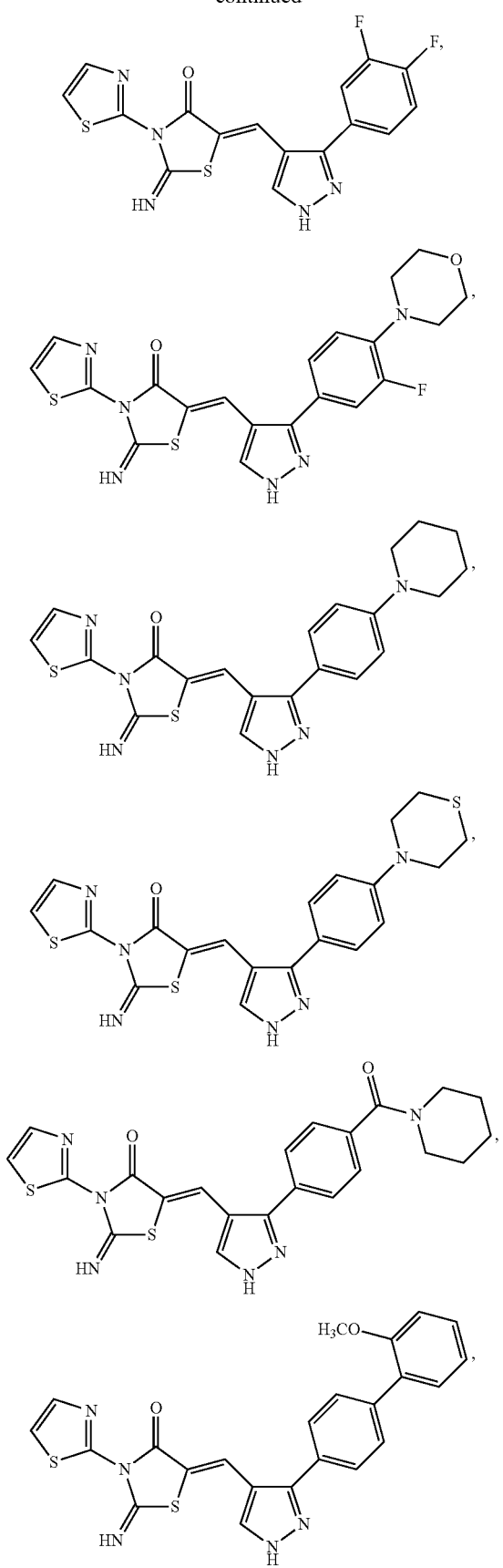

28

-continued

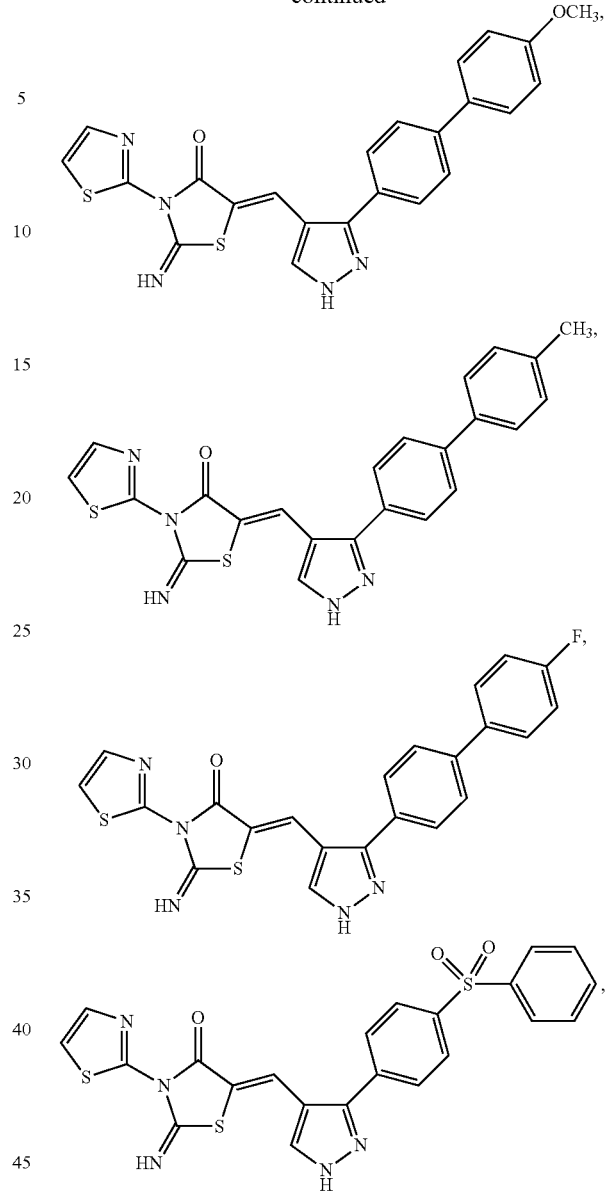

and pharmaceutically acceptable salts thereof.

The Nec-7 related compounds described above can be prepared based on synthetic procedures described in the literature, such as International Patent Application Publication No. WO 2010/075290, which is hereby incorporated by reference.

In certain embodiments, the necrostatin is a Nec-4 related compound of Formula IX:

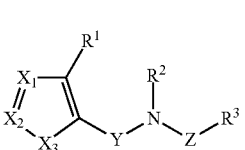

(IX)

or a pharmaceutically acceptable salt, ester, or prodrug thereof, wherein:

$X_1$ and $X_2$ are, independently, N or $CR^4$;

$X_3$ is selected from O, S, $NR^5$, or $-(CR^5)_2$;

Y is selected from C(O) or $CH_2$; and

Z is $(CR^6R^7)_n$;

$R^1$ is selected from H, halogen, optionally substituted $C_{1-6}$alkyl, or optionally substituted $C_{1-6}$cycloalkyl, or optionally substituted aryl;

$R^2$ is selected from H or optionally substituted $C_{1-6}$alkyl;

$R^3$ is optionally substituted aryl;

each $R^4$ is selected from H, halogen, carboxamido, nitro, cyano, optionally substituted $C_{1-6}$alkyl, or optionally substituted aryl;

$R^5$ is selected from H, halogen, optionally substituted $C_{1-6}$alkyl, or optionally substituted aryl;

each $R^6$ and $R^7$ is, independently, selected from H, optionally substituted $C_{1-6}$alkyl, or aryl; and n is 0, 1, 2, or 3. In certain embodiments, when $X_1$ and $X_2$ are N, $X_3$ is S, Y is C(O), Z is $CH_2$, $R^2$ is H, and $R^3$ is 2-chloro-6-fluoro-phenyl, then $R^1$ is not methyl.

In certain embodiments, the necrostatin is a Nec-4 related compound of Formula IX-A:

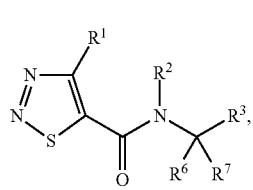

(IX-A)

or a pharmaceutically acceptable salt, ester, or prodrug thereof, wherein:

$R^1$, $R^2$, $R^3$, $R^6$ and $R^7$ are as defined in Formula (IX).

In certain embodiments, the necrostatin is a Nec-4 related compound selected from:

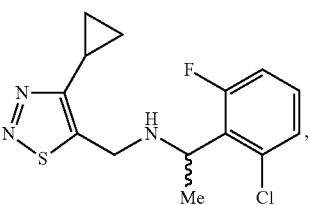

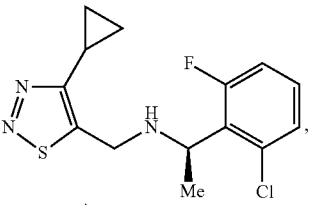

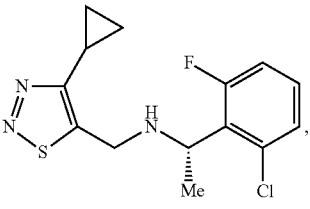

-continued

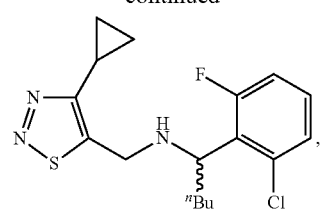

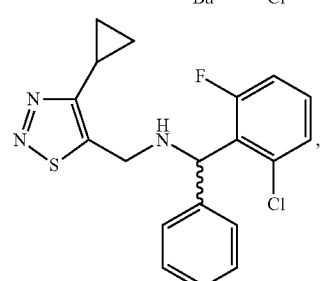

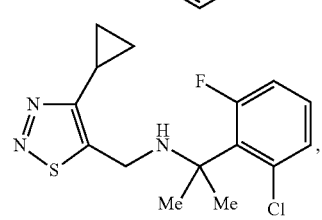

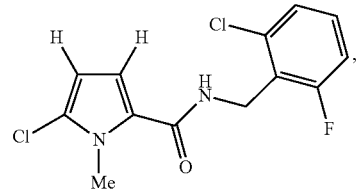

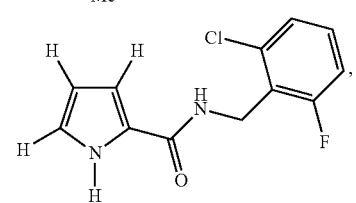

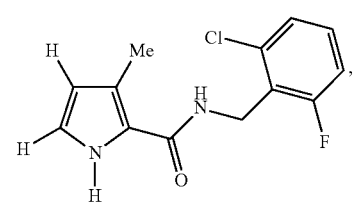

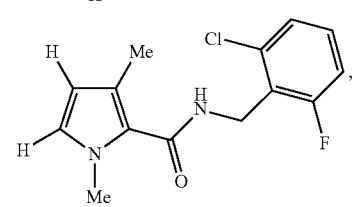

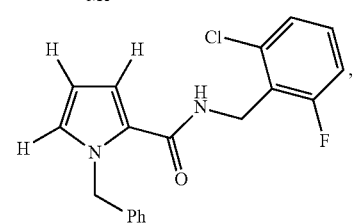

-continued

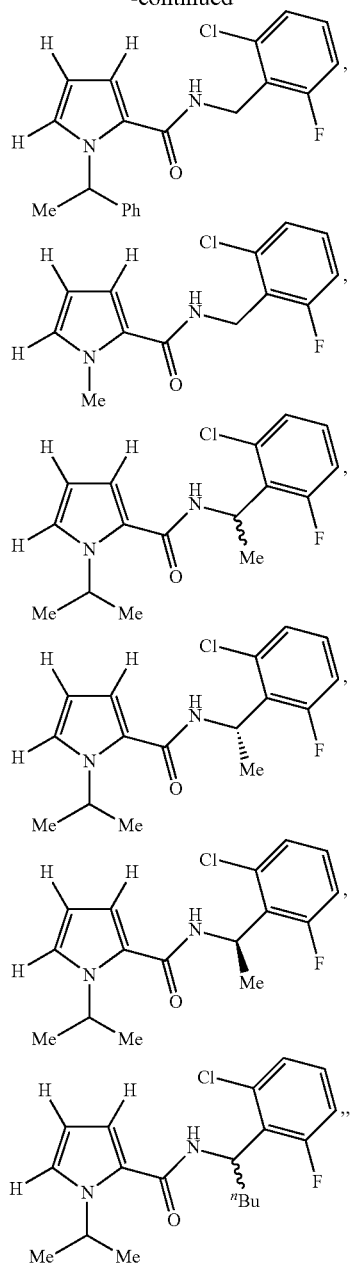

and pharmaceutically acceptable salts thereof.

The Nec-4 related compounds described above can be prepared based on synthetic procedures described in the literature, such as U.S. Patent Application Publication No. 2009/0099242, which is hereby incorporated by reference.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 10 or fewer carbon atoms in its backbone (e.g., $C_1$-$C_{10}$ for straight chain, $C_3$-$C_{10}$ for branched chain), and alternatively, 5, 4, 3, 2 or 1 carbon atoms in its backbone. Likewise, cycloalkyls have from about 3 to about 10 carbon atoms in their ring structure, and alternatively about 5, 6 or 7 carbons in the ring structure.

Exemplary alkyl groups include methyl, ethyl, n-propyl, isopropyl, n-butyl, sec-butyl, isobutyl, tert-butyl, cyclopropyl, and cyclobutyl.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, or —O-alkynyl. The term "alkylene" refers to a diradical of an alkyl group. An exemplary alkylene group is —$CH_2CH_2$—.

The term "aralkyl" refers to an alkyl group substituted with an aryl group.

The term "heteroaralkyl" refers to an alkyl group substituted with a heteroaryl group.

The term "alkenyl" refers to an unsaturated straight or branched hydrocarbon having at least one carbon-carbon double bond, such as a straight or branched group of 2-12, 2-10, or 2-6 carbon atoms, referred to herein as $C_2$-$C_{12}$alkenyl, $C_2$-$C_{10}$alkenyl, and $C_2$-$C_6$alkenyl, respectively. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, etc.

The term "alkynyl" as used herein refers to an unsaturated straight or branched hydrocarbon having at least one carbon-carbon triple bond, such as a straight or branched group of 2-12, 2-8, or 2-6 carbon atoms, referred to herein as $C_2$-$C_{12}$alkynyl, $C_2$-$C_8$alkynyl, and $C_2$-$C_6$alkynyl, respectively. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl, etc.

The term "aryl" is art-recognized and refers to a carbocyclic aromatic group. Representative aryl groups include phenyl, naphthyl, anthracenyl, and the like. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —$CO_2$alkyl, carbonyl, carboxyl, alkylthio, sulfonyl, sulfonamido, sulfonamide, ketone, aldehyde, ester, heterocyclyl, heteroaryl, —$CF_3$, —CN, or the like. The term "aryl" also includes polycyclic ring systems having two or more carbocyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, and/or aryls.

In certain embodiments, the aromatic group is not substituted, i.e., it is unsubstituted.

The term "phenylene" refers to a multivalent radical (e.g., a divalent or trivalent radical) of benzene. To illustrate, a divalent valent radical of benzene is illustrated by the formula

The terms "heterocyclyl" or "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. Heterocycles may also be mono-, bi-, or other multi-cyclic ring systems. A heterocycle may be fused to one or more aryl, partially unsaturated, or saturated rings. Heterocyclyl groups include, for example, biotinyl, chromenyl, dihydrofuryl, dihydroindolyl, dihydropyranyl, dihydrothienyl, dithiazolyl, homopiperidinyl, imidazolidinyl, isoquinolyl, isothiazolidinyl, isoxazolidinyl, morpholinyl, oxolanyl, oxazolidinyl, phenoxanthenyl, piperazinyl, piperidinyl, pyranyl, pyrazolidinyl, pyrazolinyl, pyridyl, pyrimidinyl, pyrrolidinyl, pyrrolidin-2-onyl, pyrrolinyl, tetrahydrofuryl, tetrahydroisoquinolyl, tetrahydropyranyl, tetrahydroquinolyl, thiazolidinyl, thiolanyl, thiomorpholinyl, thiopyranyl, xanthenyl, lactones, lactams such as azetidinones and pyrrolidinones, sultams, sultones, and the like. Unless specified otherwise, the heterocyclic ring is optionally substituted at one or more positions with substituents such as alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl. In certain embodiments, the heterocycicyl group is not substituted, i.e., it is unsubstituted.

The term "heteroaryl" is art-recognized and refers to aromatic groups that include at least one ring heteroatom. In certain instances, a heteroaryl group contains 1, 2, 3, or 4 ring heteroatoms. Representative examples of heteroaryl groups include pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. Unless specified otherwise, the heteroaryl ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl, —CF$_3$, —CN, or the like. The term "heteroaryl" also includes polycyclic ring systems having two or more rings in which two or more carbons are common to two adjoining rings (the rings are "fused rings") wherein at least one of the rings is heteroaromatic, e.g., the other cyclic rings may be cycloalkyls, cycloalkenyls, cycloalkynyls, and/or aryls.

The term "heteroarylene" refers to a multi-valent (e.g., di-valent or trivalent) aromatic group that comprises at least one ring heteroatom. An exemplary "heteroarylene" is pyridinylene, which is a multi-valent radical of pyridine. For example, a divalent radical of pyridine is illustrated by the formula

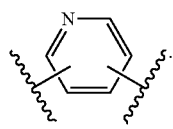

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "amine" and "amino" are art-recognized and refer to both unsubstituted and substituted amines, e.g., a moiety that may be represented by the general formula:

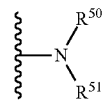

wherein $R^{50}$ and $R^{51}$ each independently represent hydrogen, alkyl, alkenyl, or —(CH$_2$)$_m$—$R^{61}$; or $R^{50}$ and $R^{51}$, taken together with the N atom to which they are attached complete a heterocycle having from 4 to 8 atoms in the ring structure; wherein $R^{61}$ is aryl, cycloalkyl, cycloalkenyl, a heterocycle or a polycycle; and m is zero or an integer in the range of 1 to 8. In certain embodiments, $R^{50}$ and $R^{51}$ each independently represent hydrogen or alkyl.

The term "amide" or "amido" as used herein refers to a radical of the form —R$_a$C(O)N(R$_b$)—, —R$_a$C(O)N(R$_b$)R$_c$—, —C(O)NR$_b$R$_c$, or —C(O)NH$_2$, wherein R$_a$, R$_b$ and R$_c$ are each independently selected from alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, and nitro. The amide can be attached to another group through the carbon, the nitrogen, R$_b$, R$_c$, or R$_a$. The amide also may be cyclic, for example R$_b$ and R$_c$, R$_a$ and R$_b$, or R$_a$ and R$_c$ may be joined to form a 3- to 12-membered ring, such as a 3- to 10-membered ring or a 5- to 6-membered ring. The term "carboxamido" refers to the structure —C(O)NR$_b$R$_c$.

The term "sulfonamide" or "sulfonamido" as used herein refers to a radical having the structure —N(R$_r$)—S(O)$_2$—R$_s$— or —S(O)$_2$—N(R$_r$)R$_s$, where R$_r$, and R$_s$ can be, for example, hydrogen, alkyl, aryl, cycloalkyl, and heterocyclyl. Exemplary sulfonamides include alkylsulfonamides (e.g., where R$_s$ is alkyl), arylsulfonamides (e.g., where R$_s$ is aryl), cycloalkyl sulfonamides (e.g., where R$_s$ is cycloalkyl), and heterocyclyl sulfonamides (e.g., where R$_s$ is heterocyclyl), etc.

The term "sulfonyl" as used herein refers to a radical having the structure R$_u$SO$_2$—, where R$_u$ can be alkyl, aryl, cycloalkyl, and heterocyclyl, e.g., alkylsulfonyl. The term "alkylsulfonyl" as used herein refers to an alkyl group attached to a sulfonyl group.

The symbol "〰" indicates a point of attachment.

Unless specified otherwise, the term "optionally substituted" as used herein means that the specified group may be substituted at one, two or more positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, heteroaryl, —CF$_3$, —CN, or the like.

As used herein, the term "therapeutically effective amount" is understood to mean the amount of an active ingredient, for example, a necrostatin (e.g., necrostatin-1 or necrostatin-4) and/or a pan-caspase inhibitor (e.g., ZVAD or IDN-6556) that is sufficient to promote axon regeneration, preserve neuron viability, and/or promote nerve function in a CNS neuron. The compounds of the invention are administered in amounts effective at, e.g., promoting axon regeneration, preserving neuron viability, promoting nerve function, increasing efficacy compared to monotherapy with either drug alone, preserving or improving cognitive functions, preserving or improving sensory functions, and/or preserving or improving motor functions. It is understood that preserving cognitive, sensory, or motor functions, includes stabilizing these functions and/or slowing the decline of these functions.

As used herein, "pharmaceutically acceptable" or "pharmacologically acceptable" mean molecular entities and compositions that do not produce an adverse, allergic or other untoward reaction when administered to an animal, or to a human, as appropriate. The term, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

Disclosed herein is a method for promoting axon regeneration in a CNS neuron by exposing the CNS neuron to an effective amount of a necrosis inhibitor and an effective amount of an apoptosis inhibitor thereby to promote the regeneration of the axon. The CNS neuron may be ex vivo. For example, the CNS neuron may be isolated from a subject and maintained in an in vitro culture. Alternatively, the CNS neuron may be present in vivo.

Also disclosed is a method for promoting nerve function following injury to a CNS neuron. The method comprises administering to a subject an effective amount of a necrosis inhibitor and an effective amount of an apoptosis inhibitor thereby to promote CNS neuron function. Further disclosed is a method for preserving the viability of a CNS neuron, wherein the method comprises administering to the subject an effective amount of a necrosis inhibitor and an effective amount of an apoptosis inhibitor thereby to preserve the viability of the CNS neuron. After administration of the necrosis inhibitor and the apoptosis inhibitor, the CNS neuron may be capable of supporting axonal regeneration.

In another aspect, the invention provides a method of treating a CNS disorder in a subject in need thereof, wherein a symptom of the CNS disorder is axon degeneration or injury within a CNS neuron. The method comprises administering to the subject an effective amount of a necrosis inhibitor and an effective amount of an apoptosis inhibitor thereby to promote regeneration of an axon in a CNS neuron affected by the CNS disorder. Following administration of the necrosis inhibitor and the apoptosis inhibitor, neuron function may be measured, for example, as an indication of axon regeneration. It is also contemplated that, following administration of the necrosis inhibitor and the apoptosis inhibitor, the neuron function of the CNS neuron is preserved or improved relative to the neuron function prior to administration of the necrosis inhibitor and the apoptosis inhibitor.

In each of the foregoing methods, the CNS disorder includes, but is not limited to, brain injury, spinal cord injury, Alzheimer's disease, amyotrophic lateral sclerosis (ALS/Lou Gehrig's Disease), Parkinson's disease, multiple sclerosis, diabetic neuropathy, polyglutamine (polyQ) diseases, stroke, Fahr disease, Menke's disease, Wilson's disease, cerebral ischemia, a prion disorder (e.g., Creutzfeldt-Jakob disease), dementia (e.g., frontotemporal dementia, dementia with lewy bodies), corticobasal degeneration, progressive supranuclear palsy, multiple system atrophy, hereditary spastic paraparesis, and spinocerebellar atrophies.

In certain embodiments, the CNS disorder affects a subject's cognitive ability, such as, brain injury to the cerebral cortex or a neurodegenerative CNS disorder, such as, Alzheimer's disease, frontotemporal dementia, dementia with Lewy bodies, corticobasal degeneration, progressive supranuclear palsy, and prion disorders.

In other embodiments, the CNS disorder affects a subject's movement and/or strength, such as injury to the brain or spinal cord, or a neurodegenerative CNS disorder such as Parkinson's disease, frontotemporal dementia, dementia with Lewy bodies, corticobasal degeneration, progress supranuclear palsy, Huntington's disease, multiple system atrophy, amyotropic lateral sclerosis, and hereditary spastic pararesis.

In yet another embodiment, the CNS disorder affects a subject's coordination, such as brain injury to the cerebellum or a neurodegenerative CNS disorder such as spinocerebellar atrophies, Friedreich's ataxia, and prion disorders.

In another aspect, the invention provides a method of promoting neuron function following injury to a CNS neuron. The method comprises reducing the production and/or activity of a RIP-1 kinase and/or RIP-3 kinase thereby promoting CNS neuron function. In certain embodiments, the reduction in the production or activity of the RIP-1 kinase and/or the RIP-3 kinase can achieved by administering an effective amount of RIP kinase (RIPK) inhibitor, e.g., a necrostatin. After treatment with the RIP kinase inhibitor, the CNS neuron may be capable of supporting axonal regeneration.

In yet another aspect, the invention provides a method of promoting axon regeneration in a CNS neuron, wherein the method comprises reducing the production and/or activity of a RIP-1 kinase and/or a RIP-3 kinase in the CNS neuron thereby promoting axon regeneration in a CNS neuron. In certain embodiments, the reduction in the production or activity of the RIP-1 kinase and/or the RIP-3 kinase can achieved by administering an effective amount of RIP kinase (RIPK) inhibitor, e.g., a necrostatin.

In each of the forgoing methods, CNS neurons include, but are not limited to, motor neurons, CNS sensory neurons, cortical neurons, cerebellar neurons, hippocampal neurons, and midbrain neurons. Exemplary motor neurons include, e.g., motor neurons of the spinal cord (e.g., somatic motor neurons and visceral/autonomic motor neurons), and motor neurons of the brain stem. Exemplary CNS sensory neurons include, e.g., secondary sensory neurons of the spinal cord and the brain stem and sensory neurons of the cortex. Exemplary cortical neurons include pyramidal cells (e.g., Betz cells), cells of Martinotti, fusiform cells, and horizontal cells of Cajal, and cortical interneurons (e.g., stellate (granule) cells, Basket cells, Chandelier cells). Exemplary hippocampal neurons include pyramidal cells, hippocampal interneurons (e.g., Basket cells) and granule cells. Exemplary cerebellar neurons include Purkinje cells, cerebellar interneurons (e.g., Basket cells, Golgi cells) and granule cells.

Unless specified, the necrostatin can be administered to give a final concentration of greater than about 10 µM, for example, in the range of about 10 µM to about 1000 µM. As described herein, the final concentration refers to final concentration in, for example, the blood, the cerebrospinal fluid, or localized region of treatment (e.g., site of injury). In certain embodiments, the necrostatin can be administered in an amount sufficient to give a final concentration of necrostatin in an amount of greater than about 10 µM. In another embodiment, the necrostatin can be administered in an amount sufficient to give a final concentration of necrostatin in an amount of greater than about 50 µM. In another embodiment, the necrostatin can be administered in an amount sufficient to give a final concentration of necrostatin in an amount of greater than about 100 µM. For example, the necrostatin may be administered in an amount sufficient to give a final concentration of necrostatin in an amount in the range from about 10 µM to about 1000 µM, 50 µM to about 1000 µM, 80 µM to about 1000 µM, about 100 µM to about 1000 µM, about 150 µM to about 1000 µM, from about 200 µM to about 800 µM, or from about 200 µM to about 600 µM. In certain embodiments, the necrostatin is administered in an amount sufficient to give a final concentration of necrostatin in an amount of about 400 µM.

The apoptosis inhibitor, for example, the pan-caspase inhibitor, can be administered in an amount sufficient to give a final concentration of the inhibitor in an amount of greater than about 3 µM, for example, in the range of about 3 µM to about 500 µM. In certain embodiments, the necrostatin can be administered in an amount sufficient to give a final concentration of necrostatin in an amount of greater than about 3 µM. In another embodiment, the necrostatin can be administered in an amount sufficient to give a final concentration of necrostatin in an amount of greater than about 30 µM. In a further embodiment, the necrostatin can be administered in an amount sufficient to give a final concentration of necrostatin in an amount of greater than about 50 µM. In yet a further embodiment, the necrostatin can be administered in an amount sufficient to give a final concentration of necrostatin in an amount of greater than about 100 µM. For example, the apoptosis inhibitor can be administered in an amount sufficient to give a final concentration of the inhibitor in an amount in the range from about 3 µM to about 500 µM, from about 80 µM to about 500 µM, 100 µM to about 500 µM, 125 µM to about 500 µM, 150 µM to about 500 µM or from about 200 µM to about 400 µM. In certain embodiments, apoptosis inhibitor (e.g., the pan-caspase inhibitor) is administered in an amount sufficient to give a final concentration of the inhibitor in an amount of about 300 µM.

In certain embodiments, from about 0.025 mg to about 4 mg, from about 0.035 mg to about 2 mg, from about 0.05 mg to about 2 mg, from about 0.1 mg to about 2 mg, from about 0.2 mg to about 1 mg, or from about 0.2 mg to about 0.8 mg of the necrosis inhibitor (e.g., a necrostatin) can be administered. In certain other embodiments, from about 0.05 mg to about 2 mg, from about 0.2 mg to about 2 mg, from about 0.05 mg to about 1.5 mg, from about 0.15 mg to about 1.5 mg, from about 0.4 mg to about 1 mg, or from about 0.5 mg to about 0.8 mg of an apoptosis inhibitor (e.g., a pan-caspase inhibitor, e.g., ZVAD) can be administered.

It is understood that one or more of a necrosis inhibitor, one or more of an apoptosis inhibitor, or one or more of a necrosis inhibitor and one or more of an apoptosis inhibitor can be administered in amounts sufficient to preserve the viability and/or promote axon regeneration and/or nerve function of an affected CNS neuron.

In certain embodiments, the necrosis inhibitor is a necrostatin, for example, necrostatin-1, a necrostatin-2, a necrostatin-4, a necrostatin-5, and a necrostatin-7. One or more of these necrosis inhibitors can be administered with one or more of the apoptosis inhibitors (e.g., IDN-6556) listed below. Furthermore, it is contemplated that one or more of the necrostatins shown by Formula I, I-A, I-B, I-C, I-D, I-E, I-F, I-G, II, II-A, III, IV, IV-A, IV-B, V, V-A, VII, VIII, VIII-A, IX, or IX-A can be administered with one or more of the apoptosis inhibitors (e.g., IDN-6556 or IDN-6734) listed below.

In certain embodiments, the necrosis inhibitor reduces the production and/or activity of a RIP-1 kinase and/or a RIP-3 kinase. RIP kinase inhibitors (e.g., RIP-1 kinase and/or RIP-3 kinase inhibitors) as disclosed herein may further include RNAs, including small inhibitory RNAs (siRNAs) and short hairpin RNAs (shRNAs). Methods for designing and synthesizing siRNAs and shRNAs are well known in the art. Exemplary RIP-1 kinase inhibitors include, for example, a pSIREN-RIP-1 shRNA construct which targets RIP-1 kinase as disclosed in Kaiser et al., (2008) JOURNAL OF IMMUNOLOGY 181:6427-6434. Exemplary RIP-3 kinase inhibitors include, for example, sc-61482-SH and sc-135170 available from Santa Cruz Biotechnology. In another example, RIP kinase inhibitors (e.g., RIP-1 kinase and/or RIP-3 kinase inhibitors) as disclosed herein may include inhibitor of apoptosis proteins (IAPs), active fragments thereof, and nucleic acids encoding the same. It is well established that IAPs inhibit RIP-1 kinase by functioning as a E3 ligase for RIP-1 kinase (see, for example, Vanlangenakker et al., (2010)).

In certain embodiments, the one or more apoptosis inhibitors may include a pan-caspase inhibitor. The pan-caspase inhibitor can be ZVAD (i.e., Z-Val-Ala-Asp(OMe)-CH$_2$F*), IDN-6556 available from Conatus Pharmaceuticals (i.e., (3-{2-[2-tert-butyl-phenylaminooxalyl)-amino]-propionylamino}-4-oxo-5-(2,3,5,6-tetrafluoro-phenoxy)-pentanoic acid) (3-{2-[(2-tert-butyl-phenylaminooxalyl)-amino]-propionylamino}-4-oxo-5-(2,3,5,6-tetrafluoro-phenoxy)-pentanoic acid), IDN-6734 available from Conatus Pharmaceuticals, VX-799 available from Vertex Pharmaceuticals, MX1013 and MX2060 derivatives available from Maxim Pharmaceuticals, M-920 available from Merck-Frosst, small-molecule compounds available from Gemin X Pharmaceuticals, RGD peptides from Merck-Frost and Maxim Pharmaceuticals, or any other known pan-caspase inhibitor.

Alternatively, the pan-caspase inhibitor can be a cocktail of caspase inhibitors including two or more specific caspase inhibitors (e.g., synthetic caspase inhibitors) such as a caspase 1 inhibitor, a caspase 2 inhibitor, a caspase 3 inhibitor, a caspase 4 inhibitor, a caspase 5 inhibitor, a caspase 6 inhibitor, a caspase 7 inhibitor, a caspase 8 inhibitor, and a caspase 9 inhibitor. It is contemplated that one or more of the pan-caspase inhibitors may be used in combination with one or more necrostatins (e.g., necrostain-1 and/or necrostatin-4).

Exemplary synthetic caspase 1 inhibitors, include, for example, Ac—N-Me-Tyr-Val-Ala-Asp-aldehyde (SEQ ID NO: 7), Ac-Trp-Glu-His-Asp-aldehyde (SEQ ID NO: 8), Ac-Tyr-N-Me-Val-Ala-N-Me-Asp-aldehyde (SEQ ID NO: 9), Ac-Tyr-Val-Ala-Asp-Aldehyde (SEQ ID NO: 10), Ac-Tyr-Val-Ala-Asp-chloromethylketone (SEQ ID NO: 11), Ac-Tyr-Val-Ala-Asp-2,6-dimethylbenzoyloxymethylketone (SEQ ID NO: 12), Ac-Tyr-Val-Ala-Asp(OtBu)-aldehyde-dimethyl acetol (SEQ ID NO: 13), Ac-Tyr-Val-Lys-Asp-aldehyde (SEQ ID NO: 14), Ac-Tyr-Val-Lys(biotinyl)-Asp-2,6-dimethylbenzoyloxymethylketone (SEQ ID NO: 15), biotinyl-Tyr-Val-Ala-Asp-chloromethylketone (SEQ ID NO: 16), Boc-Asp(OBzl)-chloromethylketone, ethoxycarbonyl-Ala-Tyr-Val-Ala-Asp-aldehyde (pseudo acid) (SEQ ID NO: 17), Z-Asp-2,6-dichlorobenzoyloxymethylketone, Z-Asp(OlBu)-bromomethylketone, Z-Tyr-Val-Ala-Asp-chloromethylketone (SEQ ID NO: 18), Z-Tyr-Val-Ala-DL-Asp-fluoromethylketone (SEQ ID NO: 19), Z-Val-Ala-DL-Asp-fluoromethylketone, and Z-Val-Ala-DL-Asp(OMe)-fluoromethylketone, all of which can be obtained from Bachem Bioscience Inc., PA. Other exemplary caspase 1 inhibitors include, for example, Z-Val-Ala-Asp-fluoromethylketone, biotin-X-Val-Ala-Asp-fluoromethylketone, Ac-Val-Ala-Asp-aldehyde, Boc-Asp-fluoromethylketone, Ac-Ala-Ala-Val-Ala-Leu-Leu-Pro-Ala-Val-Leu-Leu-Ala-Leu-Leu-Pro-Tyr-Val-Ala-Asp-aldehyde (SEQ ID NO: 1), biotin-Tyr-Val-Ala-Asp-fluoroacyloxymethylketone (SEQ ID NO: 20), Ac-Tyr-Val-Ala-Asp-acyloxymethylketone (SEQ ID NO: 21), Z-Asp-CH2-DCB, and Z-Tyr-Val-Ala-Asp-fluoromethylketone (SEQ ID NO: 22), all of which are available from Calbiochem, IDN-11104 available from Conatus Pharmaceuticals, and VX-740 and VX-756 available from Vertex Pharmaceuticals.

Exemplary synthetic caspase 2 inhibitors, include, for example, Ac-Val-Asp-Val-Ala-Asp-aldehyde (SEQ ID NO: 23), which can be obtained from Bachem Bioscience Inc., PA, and Z-Val-Asp-Val-Ala-Asp-fluoromethylketone (SEQ ID NO: 24), which can be obtained from Calbiochem, Calif.

Exemplary synthetic caspase 3 precursor protease inhibitors include, for example, Ac-Glu-Ser-Met-Asp-aldehyde (pseudo acid) (SEQ ID NO: 25) and Ac-Ile-Glu-Thr-Asp-aldehyde (pseudo acid) (SEQ ID NO: 26) which can be obtained from Bachem Bioscience Inc., PA. Exemplary synthetic caspase 3 inhibitors include, for example, Ac-Asp-Glu-Val-Asp-aldehyde (SEQ ID NO: 27), Ac-Asp-Met-Gln-Asp-aldehyde (SEQ ID NO: 28), biotinyl-Asp-Glu-Val-Asp-aldehyde (SEQ ID NO: 29), Z-Asp-Glu-Val-Asp-chloromethylketone (SEQ ID NO: 30), Z-Asp(OMe)-Glu(OMe)-Val-DL-Asp(OMe)-fluoromethylketone (SEQ ID NO: 31), and Z-Val-Ala-DL-Asp(OMe)-fluoromethylketone which can be obtained from Bachem Bioscience Inc., PA. Other exemplary caspase 3 inhibitors include, for example, Ac-Ala-Ala-Val-Ala-Leu-Leu-Pro-Ala-Val-Leu-Leu-Ala-Leu-Leu-Ala-Pro-Asp-Glu-Val-Asp-aldehyde (SEQ ID NO: 2), biotin-X-Asp-Glu-Val-Asp-fluoromethylketone (SEQ ID NO: 32), Ac-Asp-Glu-Val-Asp-chloromethylketone (SEQ ID NO: 33), all of which are available from Calbiochem. Another exemplary caspase 3 inhibitor includes, the caspase 3 inhibitor N-benzyloxycarbonal-Asp(OMe)-Glu(OMe)-Val-Asp(Ome)-fluoromethyketone (z-Asp-Glu-Val-Asp-fmk) (SEQ ID NO: 34), which is available from Enzyme Systems Products. Additional exemplary caspase 3 inhibitors include M-826 and M-791 available from Merck-Frosst, Immunocasp-3, Ad-G/iCasp3, and PEF-F8-CP3.

Exemplary synthetic caspase 4 inhibitors include, for example, Ac-Leu-Glu-Val-Asp-aldehyde (SEQ ID NO: 35) and Z-Tyr-Val-Ala-DL-Asp-fluoromethylketone (SEQ ID NO: 36), which can be obtained from Bachem Bioscience Inc., PA, and Ac-Ala-Ala-Val-Ala-Leu-Leu-Pro-Ala-Val-Leu-Leu-Ala-Leu-Leu-Ala-Pro-Leu-Glu-Val-Pro-aldehyde (SEQ ID NO: 3), which can be obtained from Calbiochem, Calif.

Exemplary synthetic caspase 5 inhibitors include, for example, Z-Trp-His-Glu-Asp-fluoromethylketone (SEQ ID NO: 37), which can be obtained from Calbiochem, Calif., and Ac-Trp-Glu-His-Asp-aldehyde (SEQ ID NO: 38) and Z-Trp-Glu(O-Me)-His-Asp(O-Me) fluoromethylketone (SEQ ID NO: 39), which can be obtained from Sigma Aldrich, Germany.

Exemplary synthetic caspase 6 inhibitors include, for example, Ac-Val-Glu-Ile-Asp-aldehyde (SEQ ID NO: 40), Z-Val-Glu-Ile-Asp-fluoromethylketone (SEQ ID NO: 41), and Ac-Ala-Ala-Val-Ala-Leu-Leu-Pro-Ala-Val-Leu-Leu-Ala-Leu-Leu-Ala-Pro-Val-Glu-Ile-Asp-aldehyde (SEQ ID NO: 4), which can be obtained from Calbiochem. Another exemplary caspase 6 inhibitor includes Immunocasp-6.

Exemplary synthetic caspase 7 inhibitors include, for example, Z-Asp(OMe)-Gln-Met-Asp(OMe) fluoromethylketone (SEQ ID NO: 42), Ac-Asp-Glu-Val-Asp-aldehyde (SEQ ID NO: 43), Biotin-Asp-Glu-Val-Asp-fluoromethylketone (SEQ ID NO: 44), Z-Asp-Glu-Val-Asp-fluoromethylketone (SEQ ID NO: 45), Ac-Ala-Ala-Val-Ala-Leu-Leu-Pro-Ala-Val-Leu-Leu-Ala-Leu-Leu-Ala-Pro-Asp-Glu-Val-Asp-aldehyde (SEQ ID NO: 2), which can be obtained from Sigma Aldrich, Germany.

Exemplary synthetic caspase 8 inhibitors include, for example, Ac-Asp-Glu-Val-Asp-aldehyde (SEQ ID NO: 46), Ac-Ile-Glu-Pro-Asp-aldehyde (SEQ ID NO: 47), Ac-Ile-Glu-Thr-Asp-aldehyde (SEQ ID NO: 48), Ac-Trp-Glu-His-Asp-aldehyde (SEQ ID NO: 49) and Boc-Ala-Glu-Val-Asp-aldehyde (SEQ ID NO: 50) which can be obtained from Bachem Bioscience Inc., PA. Other exemplary caspase 8 inhibitors include, for example, Ac-Ala-Ala-Val-Ala-Leu-Leu-Pro-Ala-Val-Leu-Leu-Ala-Leu-Leu-Ala-Pro-Ile-Glu-Thr-Asp-aldehyde (SEQ ID NO: 5) and Z-Ile-Glu-Thr-Asp-fluoromethylketone (SEQ ID NO: 51), which can be obtained from Calbiochem, Calif.

Exemplary synthetic caspase 9 inhibitors, include, for example, Ac-Asp-Glu-Val-Asp-aldehyde (SEQ ID NO: 52), Ac-Leu-Glu-His-Asp-aldehyde (SEQ ID NO: 53), and Ac-Leu-Glu-His-Asp-chloromethylketone (SEQ ID NO: 54) which can be obtained from Bachem Bioscience Inc., PA. Other exemplary caspase 9 inhibitors include, for example, Z-Leu-Glu-His-Asp-fluoromethylketone (SEQ ID NO: 55) and Ac-Ala-Ala-Val-Ala-Leu-Leu-Pro-Ala-Val-Leu-Leu-Ala-Leu-Leu-Ala-Pro-Leu-Glu-His-Asp-aldehyde (SEQ ID NO:6), which can be obtained from Calbiochem, Calif. Another exemplary caspase 9 inhibitor includes FKBP12/caspase-9 fusion protein.

The pan-caspase inhibitor may also be an endogenous caspase inhibitor or a combination of an endogenous caspase inhibitor with one or more synthetic caspase inhibitors. For example, one useful class of endogenous caspase inhibitor includes proteins known as inhibitors of apoptosis proteins (IAPs) (Deveraux et al., (1998) EMBO J. 17(8): 2215-2223) including bioactive fragments and analogs thereof. One exemplary IAP includes X-linked inhibitor of apoptosis protein (XIAP), which has been shown to be a direct and selective inhibitor of caspase-3, caspase-7 and caspase-9. Another exemplary IAP includes survivin (see, U.S. Pat. No. 6,245,523; Papapetropoulos et al., (2000) J. BIOL. CHEM. 275: 9102-9105), including bioactive fragments and analogs thereof. Survivin has been reported to inhibit caspase-3 and caspase-7 activity.

In certain embodiments, the one or more apoptosis inhibitors may target the inhibitor of apoptosis proteins (IAPs) and second mitochondria-derived activator of caspases (SMACs). Exemplary apoptosis inhibitors that target IAPs and SMACs, include, for example, BIR3 antagonists available from Idun Pharmaceuticals, capped tripeptide XIAP antagonists from Abbot Laboratories, TWX024, polyphenylurea derivatives, SMAC-mimetic compounds, embelin, XIAP antisense and RNAi constructs, AEG35156/GEM®640 available from Aegera Therapeutics, HIV-Tat- and polyarginine conjugated SMAC peptides, and nonpeptide small-molecule SMAC mimetics. It is contemplated that one or more of the apoptosis inhibitors which target IAPs and SMACs may be used in combination with one or more necrostatins (e.g., necrostain-1 and/or necrostatin-4).

In certain embodiments, the one or more apoptosis inhibitors may target the TNF-related apoptosis-inducing ligand (TRAIL) receptors. Exemplary apoptosis inhibitors that target the TRAIL receptors, include, for example, HGS-ETR1, HGS-ETR2, and HGS-TR2J available from Human Genome Sciences, and PRO1762 available from Amgen. It is contemplated that one or more of the apoptosis inhibitors which target the TRAIL receptors may be used in combination with one or more necrostatins (e.g., necrostain-1 and/or necrostatin-4).

In certain embodiments, the one or more apoptosis inhibitors may target CD95/Fas. Exemplary apoptosis inhibitors that target CD95/FAS, include, for example, CD95-Fc available from ApoGenix GmbH. It is contemplated that one or more of the apoptosis inhibitors which target CD95/Fas may be used in combination with one or more necrostatins (e.g., necrostain-1 and/or necrostatin-4).

In certain embodiments, the one or more apoptosis inhibitors may be an anti-FasL factors. Exemplary anti-FasL factors include, for example, anti-FasL neutralizing antibody (available, for example, from Pharmingen, San Diego, Calif.); peptides and nucleic acids (for example, anti-FasL aptamers) that bind FasL to prevent or reduce its binding to its cognate receptor; certain antibodies and antigen binding fragments thereof and peptides that bind preferentially to the Fas receptor; antisense nucleotides and double stranded RNA for RNAi that ultimately reduce or eliminate the production of either FasL or the Fas receptor; soluble Fas; soluble FasL; decoy receptor-3 (DcR3) and analogues thereof; matrix metalloproteinases (MMPs); vasoactive intestinal peptide (VIP); pituitary adenylate cyclase-activating polypeptide (PACAP); forskolin; combined use of benazepril and valsartan; nonpeptidic corticotropin-releasing hormone receptor type 1 (CRH-R1)-specific antagonists; mimosine; peptides that produce a defective Fas-FasL complex; platelet-activating factor (PAF); and endothelin-1 (ET-1). These anti-FasL factors can act as direct or indirect antagonists of FasL activity.

In certain embodiments, the one or more apoptosis inhibitors may target the tumor necrosis factor (TNF). Exemplary apoptosis inhibitors that target TNF, include, for example, recombinant TNF-α, adalimumab available from Abbott, infliximab available from Centocor Ortho Biotech Inc., etanercept from Amgen, CDP571 available from Celltech, and ISIS 104838 (a 2'-O-methoxyethyl antisense construct against TNF-alpha) available from ISIS Pharmaceuticals. It is contemplated that one or more of the apoptosis inhibitors which target TNF may be used in combination with one or more necrostatins (e.g., necrostain-1 and/or necrostatin-4).

In certain embodiments, the one or more apoptosis inhibitors may target survivin. Exemplary apoptosis inhibitors that target survivin, include, for example, LY2181308 available from ISIS Pharmaceuticals and Ad-survivin T34A. It is contemplated that one or more of the apoptosis inhibitors which target survivin may be used in combination with one or more necrostatins (e.g., necrostain-1 and/or necrostatin-4).

In certain embodiments, the one or more apoptosis inhibitors may target the Bcl-2 proteins. Exemplary apoptosis inhibitors that target the Bcl-2 proteins, include, for example, Bcl-2 blockers available from Idun Pharmaceuticals and Abbot Laboratories, Gx01 series of compounds available from Gemin X Pharmaceuticals, Bcl-2 small-molecule antagonist, Tetrocarcin-A derivatives available from Kyowa Hakko Kogyo Co., Chelerythrine, antimycin A derivatives, HA14-1, synthetic compound binding to the BH3 of Bcl-2, Genasense available from Sanofi-Aventis, ISIS 22783 available from ISIS Pharmaceuticals, bispecific Bcl-2/Bcl-XL antisense, BH3 peptides from Bax, Bak, Bid or Bad, SAHBs, and BH3Is. It is contemplated that one or more of the apoptosis inhibitors which target the Bcl-2 proteins may be used in combination with one or more necrostatins (e.g., necrostain-1 and/or necrostatin-4).

In certain embodiments, the one or more apoptosis inhibitors may target p53. Exemplary apoptosis inhibitors that target p53, include, for example, INGN201 available from Invitrogen Therapeutics, SCH58500 available from Schering-Plough, ONYX-015 available from Onyx Pharmaceuticals, C-terminal p53 peptides, CDB3, Amifostine, CP31398 available from Pfizer, Prima-1, HPF E6-binding peptide aptamers, Nutlins available from Roche, Chalcones, Small peptide compounds, and Pifithrin-α. It is contemplated that one or more of the apoptosis inhibitors which target p53 may be used in combination with one or more necrostatins (e.g., necrostain-1 and/or necrostatin-4).

In certain embodiments, it is contemplated that one or more necrostatins (e.g., necrostatin-1 and/or necrostatin-4) may be used in combination with a pan-caspase inhibitor. For example, in one embodiment, necrostain-1 and/or necrostatin-4 may be used in combination with ZVAD available from R&D Systems (Cat. No. FMK001) and Promega (Cat. No. G7231). In another embodiment, necrostain-1 and/or necrostatin-4 may be used in combination with IDN-6556 available from Conatus Pharmaceuticals. In yet another embodiment, necrostain-1 and/or necrostatin-4 may be used in combination with IDN-6734 available from Conatus Pharmaceuticals.

In certain embodiments, it is contemplated that one or more necrostatins (e.g., necrostatin-1 and/or necrostatin-4) may be used in combination with a TNF inhibitor. For example, in one embodiment, necrostain-1 and/or necrostatin-4 may be used in combination with adalimumab available from Abbot Laboratories. In another embodiment, necrostain-1 and/or necrostatin-4 may be used in combination with etanercept available from Amgen, Inc. In yet another embodiment, necrostain-1 and/or necrostatin-4 may be used in combination with infiximab available from Centocor Ortho Biotech, Inc.

In certain embodiments, it is contemplated that one or more necrostatins (e.g., necrostatin-1 and/or necrostatin-4) may be used in combination with a p53 agonist. For example, in one embodiment, necrostain-1 and/or necrostatin-4 may be used in combination with INGN 201 available from Invitrogen Therapeutics. In another embodiment, necrostain-1 and/or necrostatin-4 may be used in combination with nutlins, for example, nutlin-3 available from Cayman Chemical (Cat. No. 10004372). In another embodiment, necrostain-1 and/or necrostatin-4 may be used in combination with CP31398 available from Tocris Bioscience (Cat. No. 3023).

In certain embodiments, it is contemplated that one or more necrostatins (e.g., necrostatin-1 and/or necrostatin-4) may be used in combination with an anti-FasL factor. For example, in one embodiment, necrostain-1 and/or necrostatin-4 may be used in combination with anti-FasL neutralizing antibody available from Pharmingen (San Diego, Calif.).

Without wishing to be bound by theory, but as shown in FIG. 1, depending upon the specific apoptotic inhibitor chosen, it is possible that the apoptotic inhibitor can modulate both the apoptotic and necrotic pathways, and depending upon the specific necrosis inhibitor chosen, it is possible that the necrosis inhibitor can modulate both the necrotic and apoptotic pathways. For example, a RIP-1 inhibitor may inhibit both necrotic and apoptotic cell death thus preserving the viability of CNS neurons and promoting axon regeneration in a subject with a CNS disorder as disclosed herein.

As discussed herein, the disclosed methods promote axon regeneration of a CNS neuron. Further, the disclosed methods preserve neuron viability and/or promote nerve function following injury to a CNS neuron. Assessment of axonal regeneration and nerve function may be monitored by, functional tests which are well-established in the art, such as, for example, magnetic resonance imaging (MRI) and tests involving evaluations of a subject's cognitive, motor, and sensory functions.

For example, axon regeneration in a patient suffering from spinal cord injury may be measured by improvements according to the Frankel classification system, the American Spinal Injury Association (ASIA) classification system, the Yale classification system, the motor index scale, the modified Barthel index, the Basso, Beattie and Bresnahan (BBB) scale, and the like. Recovery from neuron injury can also be monitored by a neurological examination which assesses motor and sensory skills, the functioning of one or more cranial nerves, hearing and speech, vision, coordination and balance, mental status, and changes in mood or behavior, among other abilities. For example, items such as a tuning fork, flashlight, reflex hammer, ophthalmoscope, and needles may be used to evaluate motor and sensory functions. In another example, evoked potential (also called evoked response) may be employed to measure the electrical signals to the brain generated by hearing, touch, or sight, which serve as an assessment of sensory function. In a further example, neurological computed tomography, also known as a neurological CT scan, may be performed to monitor recovery from brain damage.

In another example, axonal regeneration in a stroke patient may be measured by the NIH Stroke Scale (NIHSS). The NIHSS is a standardized neurological examination that measures several aspects of brain function, including consciousness, vision, sensation, movement, speech, and language, and is intended describe the neurological deficits found in stroke patients. Other functional tests may be based on, for example, the Barthel Index (BI), which measures self-care and mobility. The BI assesses a subject's ability to perform tasks such as personal toileting, feeding, mobility from bed to chair, transfers, and bathing. Functional test may also include the Modified Rankin Scale (mRS), which is commonly used for measuring the degree of disability or dependence in the daily activities of stroke patients.

Any appropriate route of administration may be employed. For example, the necrosis inhibitor and the apoptosis inhibitor may be administered directly to the site of injury or systemically, e.g., by oral or parenteral routes. Parenteral routes include, for example, intravenous, intrarterial, intracranial, intraorbital, opthalmalic, intraventricular, intraspinal (e.g., into the cerebrospinal fluid), intracisternal, intramuscular, intradermal, subcutaneous, intranasal and intraperitoneal routes. It is contemplated that local modes of administration may reduce or eliminate the incidence of potential side effects (e.g., systemic toxicity) that may occur during systemic administration.

The necrosis inhibitor and the apoptosis inhibitor may be administered to a subject simultaneously or sequentially. It will be appreciated that when administered simultaneously, the necrosis inhibitor and the apoptosis inhibitor may be in the same pharmaceutically acceptable carrier or the two drugs may be dissolved or dispersed in separate pharmaceutical carriers, which are administered at the same time. Alternatively, the drugs may be provided in separate dosage forms and administered sequentially. For example, in some embodiments, the necrostatin may be administered before the pan-caspase inhibitor. In other examples, the pan-caspase inhibitor may be administered before the necrostatin. In addition, it is appreciated that, in some embodiments, a single active agent may inhibit both necrosis and apoptosis.

Administration may be provided as a periodic bolus (for example, intravenously) or as continuous infusion from an internal reservoir or from an external reservoir (for example, from an intravenous bag). The necrosis inhibitor and/or the apoptosis inhibitor may be administered locally, for example, by continuous release from a sustained release drug delivery device.

The necrosis inhibitor and/or the apoptosis inhibitor may be solubilized in a pharmaceutically acceptable carrier. One or both inhibitors also may be administered in a pharmaceutically acceptable carrier or vehicle so that administration does not otherwise adversely affect the recipient's electrolyte and/or volume balance. The carrier may comprise, for example, physiologic saline or other buffer system. In exemplary embodiments, the necrostatin, the pan-caspase inhibitor, or both the necrostatin and the pan-caspase inhibitor may be solubilized in PBS or another aqueous buffer by sonication. Alternatively, one or both drugs may be solubilized using conventional solvent or solubilization systems, for example, dimethyl sulfoxide (DMSO), dimethoxyethane (DME), dimethylformamide (DMF), cyclodextran, micelles, liposomes, liposomal agents, and other solvents known in the art to aid in the solubilization and administration of hydrophobic agents.

In other embodiments, the necrosis inhibitor and/or the apoptosis inhibitor may be solubilized in a liposome or microsphere. Methods for delivery of a drug or combination of drugs in liposomes and/or microspheres are well-known in the art.

In addition, it is contemplated that the necrosis inhibitor and/or the apoptosis inhibitor may be formulated so as to permit release of one or both inhibitors over a prolonged period of time. A release system can include a matrix of a biodegradable material or a material, which releases the incorporated active agents. The active agents can be homogeneously or heterogeneously distributed within a release system. A variety of release systems may be useful in the practice of the invention, however, the choice of the appropriate system will depend upon the rate of release required by a particular drug regime. Both non-degradable and degradable release systems can be used. Suitable release systems include polymers and polymeric matrices, non-polymeric matrices, or inorganic and organic excipients and diluents such as, but not limited to, calcium carbonate and sugar (for example, trehalose). Release systems may be natural or synthetic. However, under certain circumstances, synthetic release systems are preferred because generally they are more reliable, more reproducible and produce more defined release profiles. The release system material can be selected so that inhibitors having different molecular weights are released by diffusion through or degradation of the material.

Representative synthetic, biodegradable polymers include, for example: polyamides such as poly(amino acids) and poly(peptides); polyesters such as poly(lactic acid), poly(glycolic acid), poly(lactic-co-glycolic acid), and poly (caprolactone); poly(anhydrides); polyorthoesters; polycarbonates; and chemical derivatives thereof (substitutions, additions of chemical groups, for example, alkyl, alkylene, hydroxylations, oxidations, and other modifications routinely made by those skilled in the art), copolymers and mixtures thereof. Representative synthetic, non-degradable polymers include, for example: polyethers such as poly (ethylene oxide), poly(ethylene glycol), and poly(tetramethylene oxide); vinyl polymers-polyacrylates and polymethacrylates such as methyl, ethyl, other alkyl, hydroxyethyl methacrylate, acrylic and methacrylic acids, and others such as poly(vinyl alcohol), poly(vinyl pyrolidone), and poly(vinyl acetate); poly(urethanes); cellulose and its derivatives such as alkyl, hydroxyalkyl, ethers, esters, nitrocellulose, and various cellulose acetates; polysiloxanes; and any chemical derivatives thereof (substitutions, additions of chemical groups, for example, alkyl, alkylene, hydroxylations, oxidations, and other modifications routinely made by those skilled in the art), copolymers and mixtures thereof.

Treatment can be continued for as long or as short a period as desired. For example, treatments may be administered on a regimen of, for example, one to four or more times per day, one to four or more times per week, one to four or more times per month. A suitable treatment period may be, for example, at least one day, at least about one week, at least about two weeks, at least about one month, at least about six months, at least about 1 year, or indefinitely.

Throughout the description, where compositions are described as having, including, or comprising specific components, or where processes are described as having, including, or comprising specific process steps, it is contemplated that compositions of the present invention also consist essentially of, or consist of, the recited components, and that the processes of the present invention also consist essentially of, or consist of, the recited processing steps. Further, it should be understood that the order of steps or order for performing certain actions are immaterial so long as the invention remains operable. Moreover, two or more steps or actions may be conducted simultaneously.

EXAMPLES

The invention is further illustrated by the following examples, which are provided for illustrative purposes only, and should not be construed as limiting the scope or content of the invention in any way.

In the examples described herein, all animal experiments adhered to the Association for Research in Vision and Ophthalmology Statement for the Use of Animals in Ophthalmic and Vision Research, and protocols were approved by the Animal Care Committee of the Massachusetts Eye and Ear Infirmary. Wild-type C57BL/6 mice were purchased from Charles River Laboratories (Wilmington, Mass.). The mice were fed standard laboratory chow and allowed free access to water in an air-conditioned room with a 12 hour light/12 hour dark cycle. Except as noted otherwise, the animals were anesthetized with ketamine hydrochloride (30 mg/kg; Ketalar, Parke-Davis, Morris Plains, N.J.) and xylazine hydrochloride (5 mg/kg; Rompun, Harver-Lockhart, Morris Plains, N.J.) before all experimental manipulations.

The following reagents were utilized: ZVAD (Alexis, Plymouth Meeting Pa.), IDN-6556 (kindly provided by TetraLogics Pharmaceuticals), and a Nec-1 compound of Formula I-C (a kind gift from Dr. J. Yuan, Harvard Medical School, Boston, Mass.).

Intravitreal injections were performed as follows. Briefly, the tip of a 33 gauge needle (Hamilton, Reno, Nev.) was carefully inserted through the sclera into the intravitreal space to reduce intraocular pressure. Then, the needle was extracted, loaded with compounds and tangentially reinserted through the sclera into the intravitreal space, inducing a self-sealing wound tunnel After injection, the absence of choroidal bleeding was confirmed. At specified times after injury, mice were sacrificed with an overdose of sodium pentobarbital, and eyes were enucleated.

TUNEL and quantification of TUNEL (+) cells were performed as previously described (Nakazawa et al., 2007) by using the ApopTag Fluorescein In Situ Apoptosis Detection Kit (S7110; Chemicon International, Temecula, Calif.).

All values disclosed were expressed as the mean±SD. Statistical differences between two groups were analyzed by Mann-Whitney U test. Multiple group comparison was performed by ANOVA followed by Tukey-Kramer adjustments. Differences were considered significant at $P<0.05$.

Example 1: Efficacy of a Necrosis Inhibitor and a Pan-Caspase Inhibitor in Promoting RGC Survival and Axon Regeneration Like most pathways in the mature central nervous system, the optic nerve cannot regenerate if injured, leaving victims of traumatic nerve injury or degenerative diseases such as glaucoma with life-long visual losses. This situation can be, at least, partially reversed by enhancing the intrinsic growth state of retinal ganglion cells (RGCs). In this example, the efficacy of necrosis inhibitor and a pan-caspase inhibitor in promoting RGC survival and axon regeneration is investigated using a mouse optic nerve crush model.

A. A Necrosis Inhibitor in Combination with a Caspase Inhibitor Promotes RGC Survival in a Optic Nerve Crush Model Mice were subjected to optic nerve crush surgery. Specifically, animals were anesthetized with an intraperitoneal injection of ketamine (60-80 mg/kg: Phoenix Pharmaceutical, St. Joseph, Mo.) and xylazine (10-15 mg/kg: Bayer, Shawnee Mission, Kans.). Animals were positioned in a stereotaxic apparatus and a 1-1.5 cm incision was made in the skin above the right orbit. Under microscopic illumination, the lachrymal glands and extraocular muscles were resected to expose 3-4 mm of the optic nerve. The epineurium was slit open along the long axis, and the nerve was crushed 2 mm behind the eye with angled jeweler's forceps (Dumont #5) for 10 seconds, avoiding injury to the ophthalmic artery. Nerve injury was verified by the appearance of a clearing at the crush site, while the vascular integrity of the retina was evaluated by fundoscopic examination. Cases in which the vascular integrity of the retina was in question were excluded from the study.

Following surgery, mice were divided into four groups for treatment: vehicle group, ZVAD group (300 μM; given at day 0, day 3 and day 7 after injury), Nec-1 group (4 mM; given at day 0, day 3 and day 7 after injury), and ZVAD plus Nec-1 group (300 μM and 4 mM, respectively; given either once or at day 0, day 3 and day 7 after injury). Soon after injury, each group received an intravitreal injection (3 μl) with the respective compounds. As a control, one group of mice were injected with Zymosan (12.5 μg/μl), a yeast cell wall preparation, known to stimulate axonal regeneration.

Fourteen days following injection, the number of RGCs were measured by staining with an anti-Brn3a antibody. Specifically, eyes were enucleated and RGC loss was quantified from histological sections of mouse retina. Images of eight prespecified areas, 2 mm from the optic disc, were captured under fluorescent illumination (2 points/section×4 sections per eye, n=8) using a camera (Nikon E800). Brn3a-positive cells were counted using NIH ImageJ software.

Figure 2:
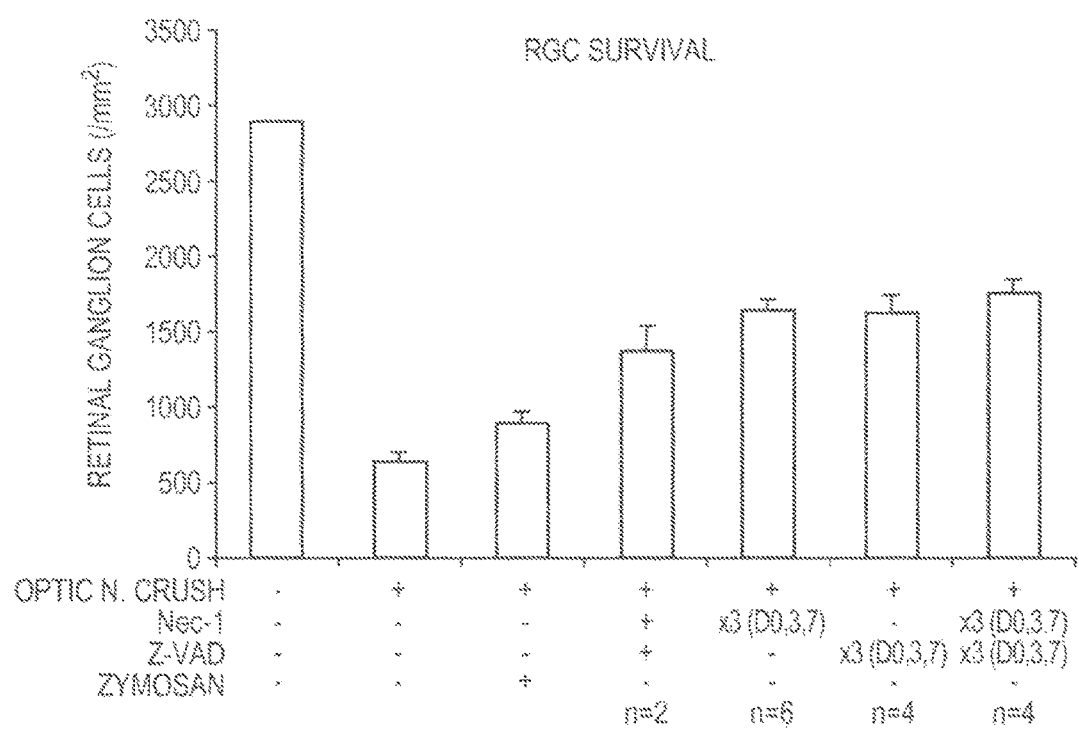
FIG. 2 provides a graph showing RGC survival in mice that were treated with ZVAD and/or Nec-1 following optic nerve crush injury.

As seen in FIG. 2, a combination of ZVAD and Nec-1 significantly prevented RGC death and promoted RGC survival following optic nerve crush injury when compared to treatment with Zymosan alone ($p<0.05$). The effect of the ZVAD and Nec-1 combination treatment on RGC survival was even more pronounced when the treatment was given at day 0, day 3 and day 7 after injury when compared to a single treatment at day 0 ($p<0.05$).

B. A Necrosis Inhibitor in Combination with a Caspase Inhibitor Promotes Axon Regeneration To investigate the efficacy of necrosis inhibitor and pan-caspase inhibitor in promoting axon regeneration, eight-weeks-old mice were subjected to optic nerve crush surgery as previously described. Subsequently, injured mice were divided into five groups of treatment: vehicle group, ZVAD group (300 µM; given at day 0, day 3 and day 7 after injury), Nec-1 group (4 mM; given at day 0, day 3 and day 7 after injury), ZVAD plus Nec-1 group (300 µM and 4 mM, respectively; given once at day 0), and ZVAD plus Nec-1 group (300 µM and 4 mM, respectively; given at day 0, day 3 and day 7 after injury).

Axon regeneration was assessed by obtaining longitudinal sections of the optic nerve and counting the number of axons at pre-specified distances from the injury site. Specifically, mice were sacrificed at 14 days after optic nerve injury and were perfused with saline and 4% paraformaldehyde (PFA). Optic nerves and eyes were dissected and postfixed in PFA. Nerves were impregnated with 10% and then 30% sucrose, embedded in OCT Tissue Tek Medium (Sakura Finetek), frozen, cut in the longitudinal plane at 14 µm, and mounted on coated slides. Regenerating axons were visualized by staining with a sheep antibody to βIII-tubulin, followed by staining with a fluorescently labeled secondary antibody. Axons were counted manually in at least eight longitudinal sections per case at pre-specified distances from the injury site. The number of regenerating axons at various distances are determined as described previously (Leon et al., (2000) J NEUROSCI 20:4615-4626). To determine the number of surviving cells, staining with an anti-Brn3a antibody was used.

Figure 3A:
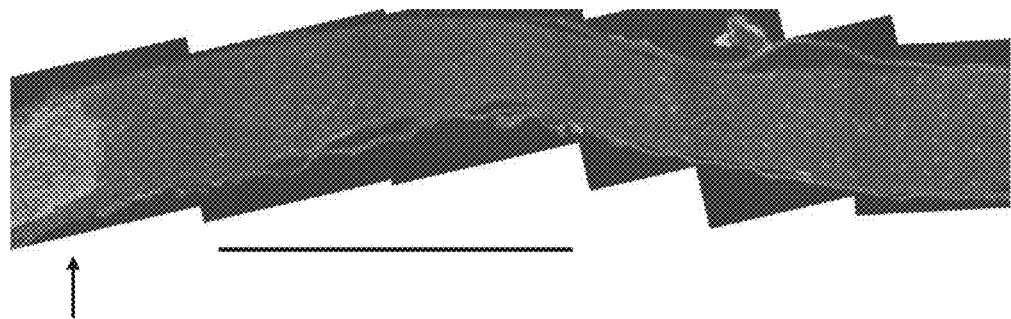
FIGS. 3A-E provide photographs showing axon regeneration in mice treated with ZVAD and/or Nec-1 following optic nerve crush injury.
Figure 3B:
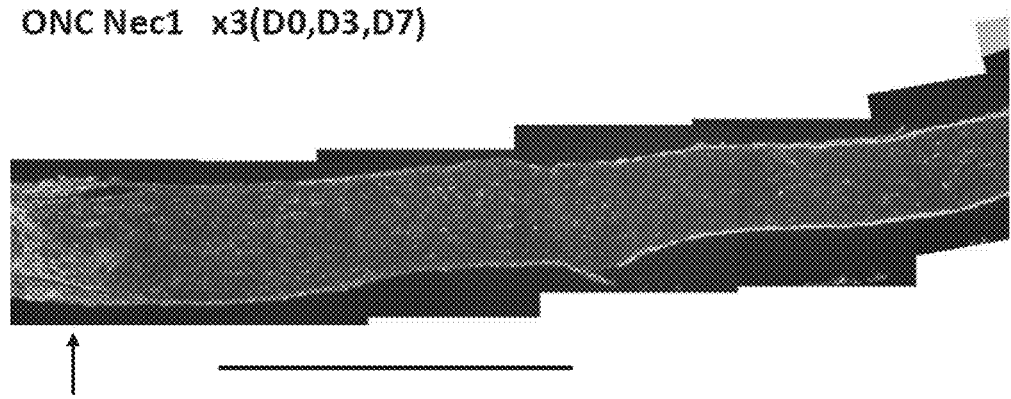
Figure 3C:
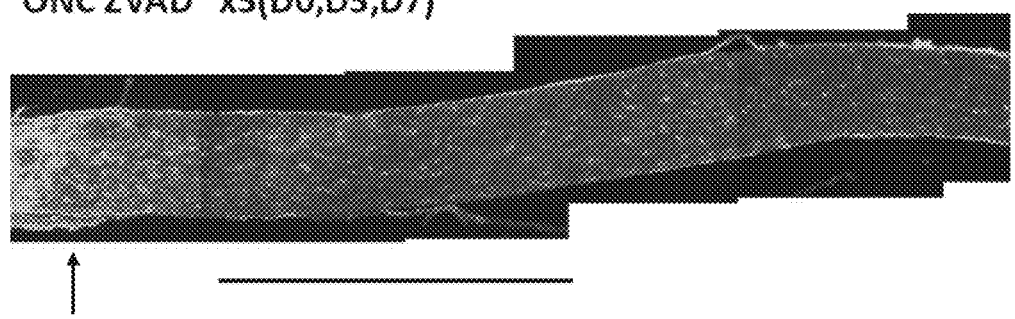
Figure 3D:
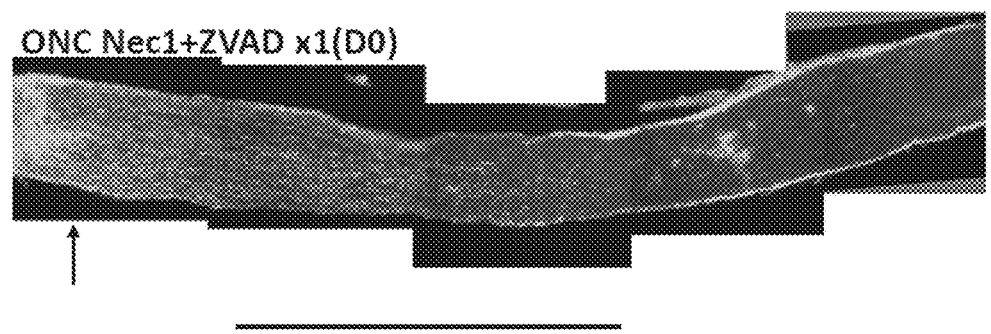
Figure 3E:
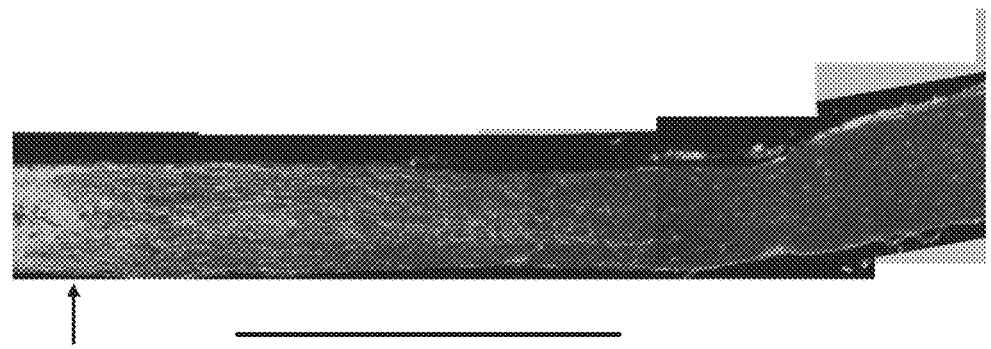

FIGS. 3A-3E show longitudinal sections of the optic nerve following optic nerve crush injury. The sections are stained with an antibody against βIII-tubulin, which marks axon fibers. In each photograph, an arrow indicates the sites of optic nerve injury, and staining beyond the injury site starting from left to right indicates axon regeneration (e.g., axons regenerate from the site of injury into the nerve). No significant axon regeneration was seen in mice treated with vehicle control, as demonstrated by the lack of axon staining (FIG. 3A). Treatment with Nec-1 or ZVAD alone had minimal effects on axon regeneration (FIGS. 3B and 3C). In contrast, ZVAD plus Nec-1 combination treatment significantly enhanced axon outgrowth as demonstrated by the increase in axon staining (FIGS. 3D and 3E; see the regions denoted by the horizontal reference lines under each figure). Further, as shown in FIGS. 3D and 3E, the effect of the ZVAD and Nec-1 combination treatment on axon regeneration was more pronounced when the treatment was given at day 0, day 3 and day 7 after injury when compared to a single treatment at day 0. These results indicate that ZVAD and Nec-1 combination treatment not only ameliorates the loss of RGC following optic nerve injury but also promotes axon regeneration following injury.

Example 2: Efficacy of a Necrosis Inhibitor and a Pan-Caspase Inhibitor in a Rat Model of Motor Neuron Regeneration The specificity of motor axon regeneration can be investigated in the rat femoral nerve. Proximally, at the site of nerve transection and suture, axons that contribute to both cutaneous and muscle branches intermingle throughout the nerve. As these axons regenerate, they have equal access to neighboring motor and sensory Schwann cell tubes in the distal nerve stump. This assures an element of "choice" at the axonal level. Distally, where the specificity of regeneration is assessed, axons are segregated into terminal cutaneous and muscle branches. Motor axons are normally found only in the muscle branch, so any motor reinnervation of the cutaneous branch represents a pathfinding failure. The specificity of axon regeneration is evaluated by simultaneous application of horseradish peroxidase (HRP) to one distal femoral branch and fluoro-gold (FG) to the other. Motor-axon regeneration is random at 3 weeks, but the number of correct projections to muscle increases dramatically at later times. Many neurons initially contain both tracers, and thus project collaterals to both cutaneous and muscle branches. The number of these double-labeled neurons decreases with time. Motor axon collaterals are thus pruned from the cutaneous branch, increasing the number of correct projections to muscle at the expense of double-labeled neurons. A specific interaction thus occurs between regenerating motor axons and muscle and/or muscle nerve.

To assess the efficacy of a necrosis inhibitor and a pan-caspase inhibitor in modifying motor axon regeneration, rats are divided into four treatment groups: vehicle group, ZVAD group, Nec-1 group, and ZVAD plus Nec-1 group. These agents are pumped onto the repair site, using an Alzet osmotic pump for at least 2 weeks. The outlet of the pump is sewn to muscle adjacent to the nerve repair, so that the nerve wound is continuously bathed with the necrosis inhibitor and the apoptosis inhibitor. Reinnervation of the distal femoral cutaneous and muscle branches can be quantified with tracers as described above.

After three weeks, motor regeneration is evaluated by assessing the number of motoneurons that projected correctly to muscle and those that projected incorrectly to the skin. It is contemplated that mice treated with ZVAD plus Nec-1 will show an increase in the mean number of correct projections and a reduction in the mean number of incorrect projections to skin relative to a controls.

Example 3: Efficacy of a Necrosis Inhibitor and a Pan-Caspase Inhibitor in a Rat Model of Damaged Vertebra Two-month old Sprague-Dawley rats (200-220 g) are used. Starting from 14 days before surgical operations, the animals undergo basic walking training for the Basso, Beattie and Bresnahan (BBB) test and the grid walk test, which measure locomotor functions. At 3 days before surgical operations, the animals are subjected to basic evaluations with respect to their behaviors and movement functions.

Rats are anesthetized with 2 kg/ml of a mixture of 25 mg/ml of ketamine and 1.3 mg/ml of Rompun and subjected to L2 Ventral Laminectomy. The animals are intramuscularly injected with the antibiotic Cefalexin (5 mg/100 g bodyweight/day) to prevent infections. Spinal cord injury is induced by opening the second lumbar vertebra of each rat and puncturing a small hole (1 mm$^2$) in the outside of the left arcus vertebra using a microrongeur. The blade of a blade holder is inserted into the hole and knifed via the dura mater to the outside of the right arcus vertebra, thus causing traumatic damage at the abdominal portion of the spine. The dorsal musculature of the damaged spinal nerve portion is sutured and ligated with surgical clips. After the surgical operation, the rats are placed on warm sawdust to maintain their body temperature, and the portion below the abdominal region is massaged 3-4 times every day for 7 days so as to discharge the content of the bladder, until the autonomic bladder control thereof is completely restored.

Following injury, the rats are divided into four treatment groups: vehicle group, ZVAD group (given at day 0, day 3 and day 7 after injury), Nec-1 group (given at day 0, day 3 and day 7 after injury), and ZVAD plus Nec-1 group (given at day 0, day 3 and day 7 after injury).

At thirty days post surgery, the rats are subjected to functional tests, such as the BBB test or the grid walk test, which measure their open-field walking ability and motor functions. The rats are further subjected to tests such as the footprint analysis, electrophysiological analysis, and histological analysis, which are known in the art, to further assess their recovery of locomotor functions. It is contemplated that rats which are treated with ZVAD plus Nec-1 will show greater improvements in locomotor functions when compared to rats treated with vehicle or with ZVAD or Nec-1 only.

INCORPORATION BY REFERENCE

The entire disclosure of each of the patent documents and scientific articles cited herein are incorporated by reference in their entirety for all purposes.

EQUIVALENTS

The invention can be embodied in other specific forms with departing from the essential characteristics thereof. The foregoing embodiments therefore are to be considered illustrative rather than limiting on the invention described herein. The scope of the invention is indicated by the appended claims rather than by the foregoing description, and all changes that come within the meaning and range of equivalency of the claims are intended to be embraced therein.

What is claimed is:

1. A method for treating a spinal cord injury in a subject by promoting axon regeneration in a Central Nervous System (CNS) neuron, the method comprising:

exposing the CNS neuron of the subject to an effective amount of a necrostatin and an effective amount of an apoptosis inhibitor thereby to promote the regeneration of the axon of the CNS neuron;

wherein the necrostatin is selected from the group consisting of:

(i) a Nec-1 related compound of Formula I:

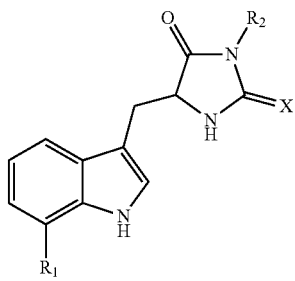

(I)

or a pharmaceutically acceptable salt, ester, or prodrug thereof, wherein

X is O or S;

$R_1$ is hydrogen, $C_1$-$C_6$alkyl, $C_1$-$C_6$ alkoxyl, or halogen; and $R_2$ is hydrogen or $C_1$-$C_6$alkyl;

(ii) a Nec-1 related compound of Formula I-A:

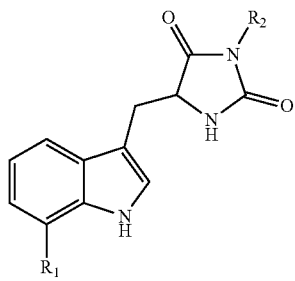

or a pharmaceutically acceptable salt, ester, or prodrug thereof, wherein $R_1$ is H, alkyl, alkoxyl, or a halogen and $R_2$ is H or an alkyl;

(iii) a Nec-1 related compound of Formula I-B:

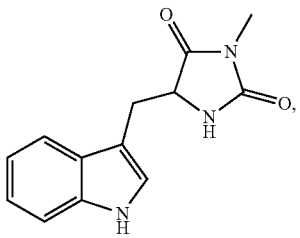 [SMILES: CN1C(=O)NC(Cc2c[nH]c3ccccc23)C1=O]

or a pharmaceutically acceptable salt, ester, or prodrug thereof;

(iv) a Nec-1 related compound of Formula I-C

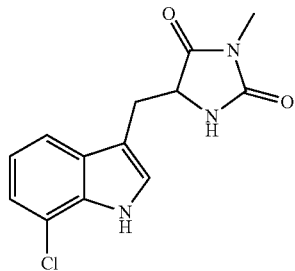 [SMILES: CN1C(=O)NC(Cc2c[nH]c3c(Cl)cccc23)C1=O]

or a pharmaceutically acceptable salt, ester, or prodrug thereof;

(v) a Nec-1 related compound of Formula I-D

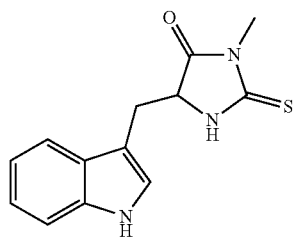 [SMILES: CN1C(=O)C(Cc2c[nH]c3ccccc23)NC1=S]

or a pharmaceutically acceptable salt thereof;

(vi) a Nec-1 related compound of Formula I-E:

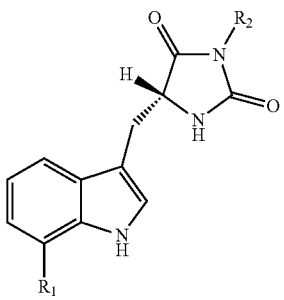

or a pharmaceutically acceptable salt, ester, or prodrug thereof,
wherein $R_1$ is H, alkyl, alkoxyl, or a halogen and $R_2$ is H or an alkyl;

(vii) a Nec-2 related compound of Formula II:

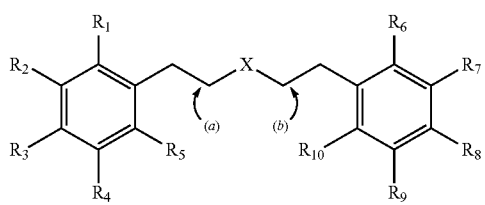

or a pharmaceutically acceptable salt, ester, or prodrug thereof, wherein:

X is —$CH_2$—, —$C(H)(R_{14})$—, —$C(=S)$—, —$C(=NH)$—, or —$C(O)$—;

$R_1$, $R_2$, $R_3$, $R_4$, $R_5$, $R_6$, $R_7$, $R_8$, $R_9$, and $R_{10}$ each represent independently hydrogen, acyl, acetyl, alkyl, halogen, amino, $C_1$-$C_6$alkoxyl, nitro, —$C(O)R_{12}$, —$C(S)R_{12}$, —$C(O)OR_{12}$, —$C(O)NR_{12}R_{13}$, —$C(S)NR_{12}R_{13}$, or —$S(O_2)R_{12}$;

$R_{11}$ is hydrogen, acyl, acetyl, alkyl, or acylamino;

$R_{12}$ and $R_{13}$ each represent independently hydrogen, an optionally substituted alkyl, an optionally substituted aryl, an optionally substituted heteroaryl, an optionally substituted aralkyl, or an optionally substituted heteroaralkyl;

$R_{14}$ is acyl, acetyl, alkyl, halogen, amino, acylamino, nitro, —$SR_{11}$, —$N(R_{11})_2$, or —$OR_{11}$;

the bond indicated by (a) can be a single or double bond; and
the bond indicated by (b) can be a single or double bond;

(viii) a Nec-2 related compound of Formula II-A:

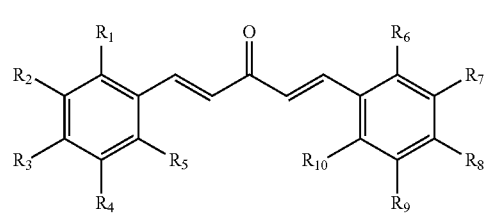

or a pharmaceutically acceptable salt thereof, wherein:
$R_1$, $R_2$, $R_5$, $R_6$, $R_7$, and $R_{10}$ each represent independently hydrogen, alkyl, halogen, amino, or methoxyl; and
$R_3$, $R_4$, $R_8$, and $R_9$ are $C_1$-$C_6$alkoxyl;

(ix) a Nec-3 related compound of Formula III:

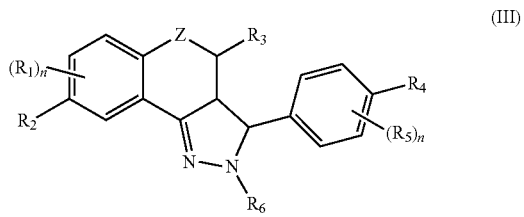

or a pharmaceutically acceptable salt, ester, or prodrug thereof, wherein:

Z is —$CH_2$—, —$CH_2CH_2$—, —O—, —S—, —S(O)—, —$S(O_2)$—, or —$N(R_7)$—;

$R_1$, $R_3$, and $R_5$ each represent independently for each occurrence hydrogen, halogen, hydroxyl, amino, $C_1$-$C_6$alkyl, $C_1$-$C_6$alkoxy, $C_1$-$C_6$alkoxy-$C_1$-$C_6$alkyl, $C_1$-$C_6$alkanoyl, $C_1$-$C_6$alkylsulfinyl, $C_1$-$C_6$alkylsulfinyl-$C_1$-$C_6$alkyl, $C_1$-$C_6$alkylsulfonyl, $C_1$-$C_6$alkylsulfonyl-$C_1$-$C_6$alkyl, aryl, aralkyl, heterocycloalkyl, heteroaryl, or heteroaralkyl;

$R_2$ and $R_4$ are $C_1$-$C_6$alkoxy;

$R_6$ is —$C(O)R_8$, —$C(S)R_8$, —$C(O)OR_8$, —$C(O)NR_8R_9$, —$C(S)NR_8R_9$, —$C(NH)R_8$, or —$S(O_2)R_8$;

$R_7$ is alkyl, aralkyl, or heteroaralkyl;

$R_8$ and $R_9$ each represent independently hydrogen, $C_1$-$C_6$alkyl, heteroalkyl, aryl, heteroaryl, aralkyl, or heteroaralkyl; and n represents independently for each occurrence 0, 1, or 2;

(x) a Nec-4 related compound of Formula IV:

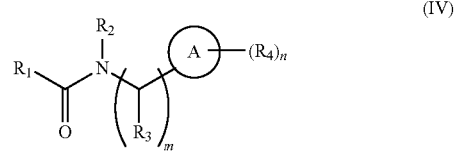

or a pharmaceutically acceptable salt, ester, or prodrug thereof, wherein:
$R_1$ is

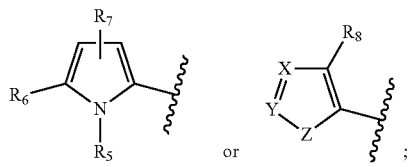

$R_2$ and $R_3$ each represent independently for each occurrence hydrogen or methyl;

$R_4$ represents independently for each occurrence halogen, hydrogen, $C_1$-$C_6$alkyl, $C_2$-$C_6$alkenyl, or $C_2$-$C_4$alkynyl;

$R_5$ is $C_1$-$C_4$alkyl;

$R_6$ is hydrogen, halogen, or —CN;

$R_7$ is hydrogen or $C_1$-$C_4$alkyl;

$R_8$ is $C_1$-$C_6$alkyl, or $R_8$ taken together with $R_9$, when present, forms a carbocyclic ring;

$R_9$ is hydrogen or $C_1$-$C_6$alkyl, or $R_9$ taken together with $R_8$ forms a carbocyclic ring;
$R_{10}$ is hydrogen or $C_1$-$C_6$alkyl;
A is phenylene or a 5-6 membered heteroarylene;
X is N or —C($R_9$)—;
Y is N or —C($R_{10}$)—;
Z is S or O; and
m and n each represent independently 1, 2, or 3;
(xi) a Nec-5 related compound of Formula V:

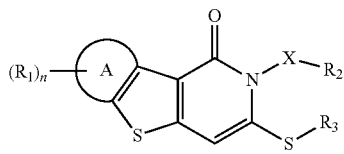
(V)

or a pharmaceutically acceptable salt, ester, or prodrug thereof, wherein:
A is a saturated or unsaturated 5-6 membered carbocyclic ring;
X is a bond or $C_1$-$C_4$alkylene;
$R_1$ is $C_1$-$C_6$ alkyl, halogen, hydroxyl, $C_1$-$C_6$alkoxyl, —N($R_4$)$_2$, —C(O)$R_4$, $CO_2R_4$, or C(O)N($R_4$)$_2$;
$R_2$ is

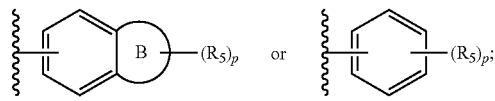

$R_3$ is —$C_1$-$C_6$alkylene-CN, —CN, $C_1$-$C_6$alkyl, or $C_2$-$C_6$alkenyl;
$R_4$ represents independently for each occurrence hydrogen, $C_1$-$C_6$alkyl, aryl, or aralkyl;
$R_5$ represents independently for each occurrence $C_1$-$C_6$alkyl, halogen, hydroxyl, $C_1$-$C_6$alkoxyl, —N($R_4$)$_2$, —C(O)$R_4$, $CO_2R_4$, or C(O)N($R_4$)$_2$;
B is a 5-6 membered heterocyclic or carbocylic ring; and
n and p each represent independently 0, 1, or 2;
(xii) a Nec-5 related compound of Formula V-A:

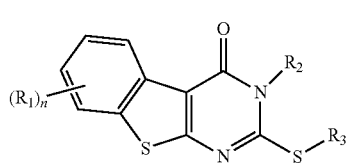
(V-A)

or a pharmaceutically acceptable salt, ester, or prodrug thereof, wherein:
$R_1$ is $C_1$-$C_6$alkyl, halogen, hydroxyl, $C_1$-$C_6$alkoxyl, or —N($R_4$)$_2$;
$R_2$ is

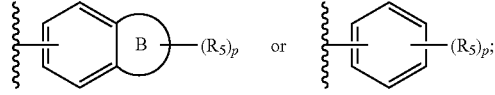

$R_3$ is —$C_1$-$C_6$alkylene-CN;
$R_4$ represents independently for each occurrence hydrogen, $C_1$-$C_6$alkyl, aryl, or aralkyl;
$R_5$ represents independently for each occurrence $C_1$-$C_6$alkyl, halogen, hydroxyl, $C_1$-$C_6$alkoxyl, —N($R_4$)$_2$, —C(O)$R_4$, $CO_2R_4$, or C(O)N($R_4$)$_2$;
B is a 5-6 membered heterocyclic or carbocylic ring; and
n and p each represent independently 0, 1, or 2;
(xiii) a Nec-7 related compound of Formula VII:

(VII)

or a pharmaceutically acceptable salt, ester, or prodrug thereof, wherein:
$R_1$, $R_2$, and $R_3$ each represent independently hydrogen or $C_1$-$C_4$alkyl;
$R_4$ is

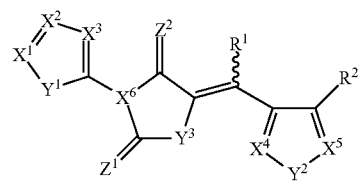

$R_5$ and $R_6$ each represent independently for each occurrence halogen, $C_1$-$C_6$alkyl, hydroxyl, $C_1$-$C_6$alkoxyl, —N($R_7$)$_2$, —NO$_2$, —S—$C_1$-$C_6$alkyl, —S-aryl, —SO$_2$—$C_1$-$C_6$alkyl, —SO$_2$-aryl, —C(O)$R_7$, —CO$_2R_7$, —C(O)N($R_7$)$_2$, heterocycloalkyl, aryl, or heteroaryl;
$R_7$ represents independently for each occurrence hydrogen, $C_1$-$C_6$alkyl, aryl, or aralkyl; or two occurrences of $R_7$ attached to the same nitrogen atom are taken together with the nitrogen atom to which they are attached to form a 3-7 membered heterocyclic ring;
A is a 5-6 membered heterocyclic ring; and
p is 0, 1, or 2;
(xiv) a Nec-7 related compound of Formula VIII:

(VIII)

or a pharmaceutically acceptable salt, ester, or prodrug thereof, wherein:
each $X^1$, $X^2$, $X^3$, $X^4$, $X^5$, and $X^6$ is selected, independently, from N or $CR^{X1}$;
each $Y^1$, $Y^2$, and $Y^3$ is selected, independently, from O, S, $NR^{Y1}$, or $CR^{Y2}R^{Y3}$;
each $Z^1$ and $Z^2$ is selected, independently, from O, S, or $NR^{Z1}$;

each $R^{Y1}$ and $R^{Z1}$ is selected, independently, from H, optionally substituted $C_{1-6}$alkyl, optionally substituted $C_{2-6}$alkenyl, optionally substituted $C_{2-6}$alkynyl, optionally substituted cycloalkyl, optionally substituted heterocyclyl, optionally substituted aryl, optionally substituted heteroaryl, —C(=O)$R^{5A}$, —C(=O)O$R^{5A}$, or —C(=O)N$R^{5A}R^{6A}$;

each $R^{X1}$, $R^{Y2}$, and $R^{Y3}$ is selected, independently, from H, halogen, CN, NC, $NO_2$, $N_3$, $OR^3$, $SR^3$, $NR^3R^4$, —C(=O)$R^{5A}$, —C(=O)O$R^{5A}$, —C(=O)N$R^{5A}R^{6A}$, —S(=O)$R^{5A}$, —S(=O)$_2R^{5A}$, —S(=O)$_2OR^{5A}$, —S(=O)$_2NR^{5A}R^{6A}$, optionally substituted $C_{1-6}$alkyl, optionally substituted $C_{2-6}$alkenyl, optionally substituted $C_{2-6}$alkynyl, optionally substituted cycloalkyl, optionally substituted heterocyclyl, optionally substituted aryl, or optionally substituted heteroaryl;

each $R^1$, $R^2$, $R^{5A}$, $R^{5B}$, $R^{6A}$, and $R^{6B}$ is selected from H, optionally substituted $C_{1-6}$ alkyl, optionally substituted $C_{2-6}$alkenyl, optionally substituted $C_{2-6}$alkynyl, optionally substituted cycloalkyl, optionally substituted heterocyclyl, optionally substituted aryl, or optionally substituted heteroaryl; or $R^{5A}$ and $R^{6A}$, or $R^{5B}$ and $R^{6B}$ combine to form a heterocyclyl; and each $R^3$ and $R^4$ is selected from H, optionally substituted $C_{1-6}$ alkyl, optionally substituted cycloalkyl, optionally substituted heterocyclyl, optionally substituted aryl, optionally substituted heteroaryl, —C(=O)$R^{5B}$, —C(=S)$R^{5B}$, —C(=N$R^{6B}$)$R^{5B}$, —C(=O)O$R^{5B}$, —C(=O)N$R^{5B}R^{6B}$, —S(=O)$R^{5B}$, —S(=O)$_2R^{5B}$, —S(=O)$_2OR^{5B}$, or —S(=O)$_2NR^{5B}R^{6B}$; and (xv) a Nec-4 related compound of Formula IX:

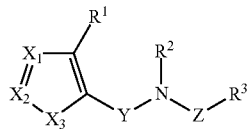

(IX)

or a pharmaceutically acceptable salt, ester, or prodrug thereof, wherein:

$X_1$ and $X_2$ are, independently, N or $CR^4$;

$X_3$ is selected from O, S, $NR^5$, or —$(CR^5)_2$;

Y is selected from C(O) or $CH_2$; and

Z is $(CR^6R^7)_n$;

$R^1$ is selected from H, halogen, optionally substituted $C_{1-6}$alkyl, or optionally substituted $C_{1-6}$cycloalkyl, or optionally substituted aryl;

$R^2$ is selected from H or optionally substituted $C_{1-6}$alkyl;

$R^3$ is optionally substituted aryl;

each $R^4$ is selected from H, halogen, carboxamido, nitro, cyano, optionally substituted $C_{1-6}$alkyl, or optionally substituted aryl;

$R^5$ is selected from H, halogen, optionally substituted $C_{1-6}$alkyl, or optionally substituted aryl;

each $R^6$ and $R^7$ is, independently, selected from H, optionally substituted $C_{1-6}$alkyl, or aryl; and n is 0, 1, 2, or 3; and wherein the apoptosis inhibitor is a pan-caspase inhibitor, a caspase-1 inhibitor, a caspase-2 inhibitor, a caspase-3 inhibitor, a caspase-4 inhibitor, a caspase-5 inhibitor, a caspase-6 inhibitor, a caspase-7 inhibitor, a caspase-8 inhibitor, a caspase-9 inhibitor, or a combination thereof.

2. The method of claim 1, wherein the neuron is ex vivo.

3. The method of claim 1, wherein the neuron is in vivo.

4. The method of claim 1, wherein the CNS neuron is selected from the group consisting of a sensory neuron, a motor neuron, a cortical neuron, a pyramidal neuron, a cerebellar neuron, a hippocampal neuron, and a midbrain neuron.

5. The method of claim 1, wherein the necrostatin is necrostatin-1, necrostatin-2, necrostatin-3, necrostatin-4, necreostatin-5, and necrostatin-7, or a combination thereof.

6. The method of claim 1, wherein from about 0.05 mg to about 2 mg of the necrostatin is administered.

7. The method of claim 1, wherein the apoptosis inhibitor is a pan-caspase inhibitor.

8. The method of claim 7, wherein the pan-caspase inhibitor is zVAD, IDN-6556 or a combination thereof.

9. The method of claim 1, wherein the necrostatin, the apoptosis inhibitor, or both the necrostatin and the apoptosis inhibitor are administered locally.

10. The method of claim 1, wherein the necrostatin, the apoptosis inhibitor, or both the necrostatin and the apoptosis inhibitor are administered systemically.

11. The method of claim 1, wherein the necrostatin, the apoptosis inhibitor, or both the necrostatin and the apoptosis inhibitor are administered sequentially or simultaneously.

12. The method of claim 1, wherein the spinal cord injury is selected from the group consisting of chronic spinal cord injury, acute spinal cord injury, and traumatic spinal cord injury.

* * * * *

UNITED STATES PATENT AND TRADEMARK OFFICE
CERTIFICATE OF CORRECTION

PATENT NO. : 10,022,419 B2
APPLICATION NO. : 14/930501
DATED : July 17, 2018
INVENTOR(S) : Demetrios Vavvas et al.

Page 1 of 1

It is certified that error appears in the above-identified patent and that said Letters Patent is hereby corrected as shown below:

In the Claims

Claim 1, Column 71, at Line 45, replace "$C_1$-$C_6$ alkoxyl" with --$C_1$-$C_6$alkoxyl--.

Claim 1, Column 72, at Line 28, insert --:-- directly after "Formula I-C"; and at Line 53, insert --:-- directly after "Formula I-D".

Claim 1, Column 75, at Line 13, replace " 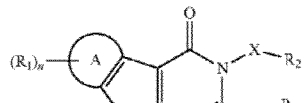 " with

-- [structure] --; and at Line 25, replace "$C_1$-$C_6$ alkyl" with --$C_1$-$C_6$alkyl--.

Claim 1, Column 76, at Line 7, replace "carbocylic" with --carbocyclic--.

Claim 1, Column 77, at Lines 18 and 25, replace each instance of "$C_{1-6}$ alkyl" with --$C_1$-$C_6$alkyl--.

Signed and Sealed this
Thirtieth Day of April, 2019

Andrei Iancu
*Director of the United States Patent and Trademark Office*

```
                         SEQUENCE LISTING

<160> NUMBER OF SEQ ID NOS: 55

<210> SEQ ID NO 1
<211> LENGTH: 19
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 1

Ala Ala Val Ala Leu Leu Pro Ala Val Leu Leu Ala Leu Leu Pro Tyr
1               5                   10                  15

Val Ala Asp

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 2

Ala Ala Val Ala Leu Leu Pro Ala Val Leu Leu Ala Leu Leu Ala Pro
1               5                   10                  15

Asp Glu Val Asp
            20

<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 3

Ala Ala Val Ala Leu Leu Pro Ala Val Leu Leu Ala Leu Leu Ala Pro
1               5                   10                  15

Leu Glu Val Pro
            20

<210> SEQ ID NO 4
<211> LENGTH: 20
<212> TYPE: PRT
<213> ORGANISM: Artificial Sequence
<220> FEATURE:
```

```
<223> OTHER INFORMATION: Description of Artificial Sequence: Chemically
      synthesized peptide

<400> SEQUENCE: 4

Ala Ala Val Ala Leu Leu Pro Ala Val Leu Leu Ala Leu Leu Ala Pro
1               5                   10                  15

Val Glu Ile Asp
            20

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 5

Ala Ala Val Ala Leu Leu Pro Ala Val Leu Leu Ala Leu Leu Ala Pro
1               5                   10                  15

Ile Glu Thr Asp
            20

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 6

Ala Ala Val Ala Leu Leu Pro Ala Val Leu Leu Ala Leu Leu Ala Pro
1               5                   10                  15

Leu Glu His Asp
            20

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide
<220> FEATURE:
<221> NAME/KEY: MOD_RES
<222> LOCATION: (1)..(1)
<223> OTHER INFORMATION: N-Me-Tyr

<400> SEQUENCE: 7

Tyr Val Ala Asp
1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 8

Trp Glu His Asp
1

<210> SEQ ID NO 9
```

-continued

```
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide
<220> FEATURE:
<221> NAME/KEY: MOD_RES
<222> LOCATION: (2)..(2)
<223> OTHER INFORMATION: N-Me-Val
<220> FEATURE:
<221> NAME/KEY: MOD_RES
<222> LOCATION: (4)..(4)
<223> OTHER INFORMATION: N-Me-Asp

<400> SEQUENCE: 9

Tyr Val Ala Asp
1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 10

Tyr Val Ala Asp
1

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 11

Tyr Val Ala Asp
1

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 12

Tyr Val Ala Asp
1

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide
<220> FEATURE:
<221> NAME/KEY: MOD_RES
<222> LOCATION: (4)..(4)
<223> OTHER INFORMATION: Asp(OtBu)

<400> SEQUENCE: 13

Tyr Val Ala Asp
1
```

```
<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 14

Tyr Val Lys Asp
1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide
<220> FEATURE:
<221> NAME/KEY: MOD_RES
<222> LOCATION: (3)..(3)
<223> OTHER INFORMATION: Lys(biotinyl)

<400> SEQUENCE: 15

Tyr Val Lys Asp
1

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 16

Tyr Val Ala Asp
1

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 17

Ala Tyr Val Ala Asp
1               5

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 18

Tyr Val Ala Asp
1

<210> SEQ ID NO 19
<211> LENGTH: 4
<212> TYPE: PRT
```

```
<213> ORGANISM: Artificial Sequence
<220> FEATURE:
<223> OTHER INFORMATION: Description of Artificial Sequence: Chemically
      synthesized peptide
<220> FEATURE:
<221> NAME/KEY: MOD_RES
<222> LOCATION: (4)..(4)
<223> OTHER INFORMATION: DL-Asp

<400> SEQUENCE: 19

Tyr Val Ala Asp
1

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 20

Tyr Val Ala Asp
1

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 21

Tyr Val Ala Asp
1

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 22

Tyr Val Ala Asp
1

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 23

Val Asp Val Ala Asp
1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Chemically
      synthesized peptide
```

```
<400> SEQUENCE: 24

Val Asp Val Ala Asp
1               5

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 25

Glu Ser Met Asp
1

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 26

Ile Glu Thr Asp
1

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 27

Asp Glu Val Asp
1

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 28

Asp Met Gln Asp
1

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 29

Asp Glu Val Asp
1

<210> SEQ ID NO 30
<211> LENGTH: 4
<212> TYPE: PRT
```

```
<213> ORGANISM: Artificial Sequence
<220> FEATURE:
<223> OTHER INFORMATION: Description of Artificial Sequence: Chemically
      synthesized peptide

<400> SEQUENCE: 30

Asp Glu Val Asp
1

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide
<220> FEATURE:
<221> NAME/KEY: MOD_RES
<222> LOCATION: (1)..(1)
<223> OTHER INFORMATION: Asp(OMe)
<220> FEATURE:
<221> NAME/KEY: MOD_RES
<222> LOCATION: (2)..(2)
<223> OTHER INFORMATION: Glu(OMe)
<220> FEATURE:
<221> NAME/KEY: MOD_RES
<222> LOCATION: (4)..(4)
<223> OTHER INFORMATION: DL-Asp(OMe)

<400> SEQUENCE: 31

Asp Glu Val Asp
1

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 32

Asp Glu Val Asp
1

<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 33

Asp Glu Val Asp
1

<210> SEQ ID NO 34
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide
<220> FEATURE:
<221> NAME/KEY: MOD_RES
<222> LOCATION: (1)..(1)
<223> OTHER INFORMATION: Asp(OMe)
<220> FEATURE:
<221> NAME/KEY: MOD_RES
<222> LOCATION: (2)..(2)
```

```
<223> OTHER INFORMATION: Glu(OMe)
<220> FEATURE:
<221> NAME/KEY: MOD_RES
<222> LOCATION: (4)..(4)
<223> OTHER INFORMATION: Asp(OMe)

<400> SEQUENCE: 34

Asp Glu Val Asp
1

<210> SEQ ID NO 35
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 35

Leu Glu Val Asp
1

<210> SEQ ID NO 36
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide
<220> FEATURE:
<221> NAME/KEY: MOD_RES
<222> LOCATION: (4)..(4)
<223> OTHER INFORMATION: DL-Asp

<400> SEQUENCE: 36

Tyr Val Ala Asp
1

<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 37

Trp His Glu Asp
1

<210> SEQ ID NO 38
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 38

Trp Glu His Asp
1

<210> SEQ ID NO 39
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide
```

```
<220> FEATURE:
<221> NAME/KEY: MOD_RES
<222> LOCATION: (2)..(2)
<223> OTHER INFORMATION: Glu(O-Me)
<220> FEATURE:
<221> NAME/KEY: MOD_RES
<222> LOCATION: (4)..(4)
<223> OTHER INFORMATION: Asp(O-Me)

<400> SEQUENCE: 39

Trp Glu His Asp
1

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 40

Val Glu Ile Asp
1

<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 41

Val Glu Ile Asp
1

<210> SEQ ID NO 42
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide
<220> FEATURE:
<221> NAME/KEY: MOD_RES
<222> LOCATION: (1)..(1)
<223> OTHER INFORMATION: Asp(OMe)
<220> FEATURE:
<221> NAME/KEY: MOD_RES
<222> LOCATION: (4)..(4)
<223> OTHER INFORMATION: Asp(OMe)

<400> SEQUENCE: 42

Asp Gln Met Asp
1

<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 43

Asp Glu Val Asp
1
```

```
<210> SEQ ID NO 44
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 44

Asp Glu Val Asp
1

<210> SEQ ID NO 45
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 45

Asp Glu Val Asp
1

<210> SEQ ID NO 46
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 46

Asp Glu Val Asp
1

<210> SEQ ID NO 47
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 47

Ile Glu Pro Asp
1

<210> SEQ ID NO 48
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 48

Ile Glu Thr Asp
1

<210> SEQ ID NO 49
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 49
```

-continued

Trp Glu His Asp
1

<210> SEQ ID NO 50
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 50

Ala Glu Val Asp
1

<210> SEQ ID NO 51
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 51

Ile Glu Thr Asp
1

<210> SEQ ID NO 52
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 52

Asp Glu Val Asp
1

<210> SEQ ID NO 53
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 53

Leu Glu His Asp
1

<210> SEQ ID NO 54
<211> LENGTH: 4
<212> TYPE: PRT
<213> ORGANISM: Artificial Sequence
<220> FEATURE:
<223> OTHER INFORMATION: Description of Artificial Sequence: Chemically
      synthesized peptide

<400> SEQUENCE: 54

Leu Glu His Asp
1

<210> SEQ ID NO 55
<211> LENGTH: 4
<212> TYPE: PRT
<213> ORGANISM: Artificial Sequence
<220> FEATURE:
<223> OTHER INFORMATION: Description of Artificial Sequence: Chemically synthesized peptide

<400> SEQUENCE: 55

Leu Glu His Asp
1